US008653109B2

(12) United States Patent
Nell et al.

(10) Patent No.: US 8,653,109 B2
(45) Date of Patent: Feb. 18, 2014

(54) SUBSTITUTED BIPYRIDINE DERIVATIVES AND THEIR USE AS ADENOSINE RECEPTOR LIGANDS

(75) Inventors: Peter Nell, Wuppertal (DE); Walter Hübsch, Wuppertal (DE); Barbara Albrecht-Küpper, Wulfrath (DE); Joerg Keldenich, Wuppertal (DE); Andreas Knorr, Erkrath (DE)

(73) Assignee: Bayer Intellectual Property GmbH, Monheim (DE)

( * ) Notice: Subject to any disclaimer, the term of this patent is extended or adjusted under 35 U.S.C. 154(b) by 730 days.

(21) Appl. No.: 12/440,423

(22) PCT Filed: Aug. 30, 2007

(86) PCT No.: PCT/EP2007/007572
§ 371 (c)(1),
(2), (4) Date: Dec. 23, 2009

(87) PCT Pub. No.: WO2008/028590
PCT Pub. Date: Mar. 13, 2008

(65) Prior Publication Data
US 2010/0093728 A1  Apr. 15, 2010

(30) Foreign Application Priority Data

Sep. 8, 2006 (DE) .......................... 10 2006 042 143

(51) Int. Cl.
*A61K 31/444* (2006.01)
*C07D 211/60* (2006.01)
(52) U.S. Cl.
USPC ............................ 514/334; 546/257; 546/258
(58) Field of Classification Search
USPC .................. 546/256, 257, 258; 514/333, 334
See application file for complete search history.

(56) References Cited

U.S. PATENT DOCUMENTS

| 4,052,510 A | 10/1977 | Simpson et al. |
| 5,670,525 A | 9/1997 | Urbahns et al. |
| 5,889,002 A | 3/1999 | Nielsen et al. |
| 6,191,280 B1 | 2/2001 | Hamprecht et al. |
| 6,632,823 B1 | 10/2003 | Vernier et al. |
| 6,693,102 B2 | 2/2004 | Stasch et al. |
| 6,706,717 B2 | 3/2004 | Barrish et al. |
| 6,743,798 B1 | 6/2004 | Straub et al. |
| 6,833,364 B1 | 12/2004 | Straub et al. |
| 6,864,287 B1 | 3/2005 | Alonso-Alija et al. |
| 7,045,631 B2 | 5/2006 | Rosentreter et al. |
| 7,078,417 B2 | 7/2006 | Rosentreter et al. |
| 7,129,255 B2 | 10/2006 | Rosentreter et al. |
| 7,173,036 B2 | 2/2007 | Sircar et al. |
| 7,173,037 B2 | 2/2007 | Alonso-Alija et al. |
| 7,186,716 B2 | 3/2007 | Wei et al. |
| 7,674,825 B2 | 3/2010 | Alonso-Alija et al. |
| 7,692,017 B2 | 4/2010 | Dinsmore et al. |
| 7,705,043 B2 | 4/2010 | Alonso-Alija et al. |
| 7,709,504 B2 | 5/2010 | Krahn et al. |
| 7,781,470 B2 | 8/2010 | Alonso-Alija et al. |
| 7,855,219 B2 | 12/2010 | Rosentreter et al. |
| 7,932,259 B2 | 4/2011 | Nakazato et al. |
| 7,951,811 B2 | 5/2011 | Nakazato et al. |
| 2004/0162427 A1 | 8/2004 | Rosentreter et al. |
| 2004/0176446 A1 | 9/2004 | Alonso-Alija et al. |
| 2005/0182105 A1 | 8/2005 | Nirschl et al. |
| 2005/0227972 A1 | 10/2005 | Rosentreter et al. |
| 2005/0250774 A1 | 11/2005 | Ono et al. |
| 2006/0154969 A1 | 7/2006 | Rosentreter et al. |
| 2006/0264432 A1 | 11/2006 | Rosentreter et al. |
| 2007/0066630 A1 | 3/2007 | Palani et al. |
| 2007/0213372 A1 | 9/2007 | Rosentreter et al. |
| 2007/0293670 A1 | 12/2007 | Nakazato et al. |
| 2008/0167321 A1 | 7/2008 | Kamboj et al. |
| 2008/0269300 A1 | 10/2008 | Erguden et al. |
| 2009/0221649 A1 | 9/2009 | Krahn et al. |
| 2010/0009973 A1 | 1/2010 | Rhodes et al. |
| 2010/0022544 A1 | 1/2010 | Nell et al. |
| 2010/0048641 A1 | 2/2010 | Nell et al. |
| 2010/0069363 A1 | 3/2010 | Nell et al. |
| 2010/0197609 A1 | 8/2010 | Vakalopoulos et al. |
| 2011/0130377 A1 | 6/2011 | Nell et al. |
| 2011/0207698 A1 | 8/2011 | Meibom et al. |
| 2011/0294718 A1 | 12/2011 | Lerchen et al. |
| 2011/0294719 A1 | 12/2011 | Lerchen et al. |

FOREIGN PATENT DOCUMENTS

| EP | 0608565 A1 | 12/1993 |
| EP | 1302463 | 4/2003 |
| JP | 09-132529 | 5/1997 |
| JP | 10-324687 | 12/1998 |
| JP | 2003-183254 | 7/2003 |

(Continued)

OTHER PUBLICATIONS

Guillory (in Brittain ed.), "Polymorphism, etc.," NY: Marcel Dekker, Inc., 1999, 1-2, 125-181, 183-226.*
Yu et al., "Physical characterization of, etc.," PSTT, vl. 1(3), 118-127 (1998).*
Vippagunta et al., "Crystalline Solids", Advanced Drug Delivery Reviews 48 (2001) 3-26.*
Olah et al., Cloning, Expression, and Characterization of the Unique Bovine $A_1$ Adenosine Receptor, The Jnl. of Biological Chemistry, vol. 267, No. 15, May 25, 1992, pp. 10764-10770, USA.
Klotz et al., Comparative Pharmacology of Human Adenosine Receptor Subtypes—Characterization of stably transfected receptors in CHO cells, Naunyn-Schmiedeberg's Arch Pharmacol, 1998, 357: 1-9.
Poulsen et al., Adenosine Receptors: New Opportunities for Future Drugs, Bioorganic & Medicinal Chemistry 6, 1998, 619-641.

(Continued)

*Primary Examiner* — Patricia L Morris
(74) *Attorney, Agent, or Firm* — Karen B. King

(57) ABSTRACT

The present invention relates to novel substituted 2,4'- and 3,4'-bipyridine derivatives, to processes for their preparation, to their use for the treatment and/or prophylaxis of diseases and to their use for preparing medicaments for the treatment and/or prophylaxis of diseases, preferably for the treatment and/or prevention of hypertension and other cardiovascular disorders.

5 Claims, No Drawings

(56) References Cited

FOREIGN PATENT DOCUMENTS

| WO | 95/34563 | 12/1995 |
| --- | --- | --- |
| WO | 97/27177 A2 | 7/1997 |
| WO | 99/03861 A1 | 1/1999 |
| WO | WO 01/25210 | 4/2001 |
| WO | WO 01/62233 | 8/2001 |
| WO | 02/48115 A2 | 6/2002 |
| WO | WO 02/50071 | 6/2002 |
| WO | WO 02/070485 | 9/2002 |
| WO | WO 03/053441 | 7/2003 |
| WO | 03/091246 | 11/2003 |
| WO | 2004/014372 A1 | 2/2004 |
| WO | WO 2004/054505 | 7/2004 |
| WO | 2005/007647 A1 | 1/2005 |
| WO | WO 2006/027142 | 3/2006 |
| WO | 2007/073855 | 7/2007 |

OTHER PUBLICATIONS

Anand, et al.:"Novel Dipeptide Prodrugs of Acyclovir for Ocular Herpes Infections: Bioreversion, Antiviral Activity and Transport Across Rabbit Cornea," Current Eye Research, Mar. 2003, 26 (3-4):151-163.

Avila, et al.: A1-, A2A- and A3-subtype adenosine receptors modulate intraocular pressure in the mouse, British Journal of Pharmacology, 2001, 134:241-245.

Barton et al.,:"Homologation of Acids via Carbon Radicals Generated from the Acyl Derivatives of N-Hydroxy-2- Thiopyrodine. (The Two-Carbon Problem)," Tetrahedron Letters, 1991, 32(28): 3309-3312.

Bauman:"Updating the Evidence that Physical Activity is Good for Health: An Epidemiological Review 2000-2003," J. Sci. Med. Sport, Apr. 2004, 7(1): Suppl:6-19.

Beaumont, et al.:"Design of Ester Prodrugs to Enhance Oral Absorption of Poorly Permeable Compounds: Challenges to the Discovery Scientist," Current Drug Metabolism, 2003, 4(6):461-485.

Beukers, et al.:"New, Non-Adenosine, High-Potency Agonists for the Human Adenosine A2B Receptor with an Improved Selectivity Profile Compared to the Reference Agonist N-Ethylcarboxamidoadenosine," Journal of Medicinal Chemistry, Jul. 15, 2004, 47(15): 3707-3709.

Bundgaard:"Design of Prodrugs: Bioreversible derivatives for various functional groups and chemical entities," Elsevier Science Publishers B.V., 1985, pp. 1-92.

Castedo, et al.:"Synthesis and Pharmacological Activity of Some Nitrofuraldehyde Cyanopyridine Derivatives," Eur. J. Med. Chem., 1984, 19(6):555-557, abstract retrieved from CAPLUS Accession No. 1985:437337, EPO Document XP002202946.

Cesar, et al.:"Trimethylsilyldiazomethane in the Preparation of Diazoketonesvia Mixed Anhydride and Coupling Reagent Methods: A New Approach to the Arndt-Eistert Synthesis," Tetrahedron Letters, 2001, 42: 7099-7102.

Crosson: "Intraocular Pressure Responses to the AdenosineAgonist Cyclohexyladenosine: Evidence for a DualMechanism of Action," IOVS, Jul. 2001, 42(8): 1837-1840.

Dhalla, et al.:"Pharmacology and Theraputic Applications of A1 Adenosine Receptor Ligands," Current Topics in Medicinal Chemisty, 2003, 3:369-385.

Dyachenko, et al.:"Single Stage Synthesis of 2-Alkylthio(seleno)-4-Hetaryl-3-cyano-5,6,7,8-Tetrahydroquinolines," Chemistry of Heterocyclic Compounds, 1997, 33(10): 1203-1208.

Dyachenko, et al.:"New Route to 6-Amino-4-aryl-3,5-dicyano-pyridine-2(1H)-thiones," Russian Journal of Organic Chemistry,1997, 33(7):1014-1017.

Dyachenko, et al.:"Michael Reaction in SyntheSis of 6-Amino-4-(4-Butoxyphenyl)-3,5-Dicyanopyridine-2(1H)-thionene," Chemistry of Heterocyclic Compounds, 1998, 34(2):188-194.

Dyachenko:"Cyclohexanecarbaldehyde in Multicomponent Syntheses of Functionalized Cyclohexyl-Substituted Acrylonitriles, 4H-Chalcogenopyrans, 1,4-Dihydropyridines, and Pyridines," Russian Journal of General Chemistry, 2006, 76(2):282-291.

Dyachenko, et al.,:"Synthesis and Recyclization of 4-Aryl-2,6-diamino-3,5-dicyano-4H-thiopyrans," Russian Journal of Organic Chemistry, 1998, 34(4): 557-563.

Eissa, et al.:"Synthesis and Biological Evaluation of Pyrido[2,3-d]pyrimidine as Antitumor Effect," Egypt. J. Chem., 2006, 49(6):761-774.

Elnagdi, et al.:"Studies with Polyfunctionally Substituted Heterocycles: Synthesis of New Pyridines, Naphtho[1,2-b] pyrans, Pyrazolo[3,4]pyridines and Pyrazolo[1,5-a]pyrimidines," Z. Naturforsch, 1992, 47b:572-578.

El-Torgoman, et al.:"Nitriles in Heterocyclic Synthesis: The reaction of 2-Thiocarbamoyl Cinnamonitriles with Active Methylene Reagents," Z. Naturforsch., 1987, 42b:107-111.

Ettmayer, et al.:"Lessons Learned from Marketed and Investigational Prodrugs," J. Med. Chem., May 6, 2004, 47(10) 2393-2404.

Fuentes, et al.:"Heterocycle Synthesis. XVI. Reaction of Malononitrile with Benzylidenemalononitriles in Presence of Amines." An. Quim., Ser. C., 1980, 76(1): 68-69, English language abstract retrieved from CAPLUS Accession No. 1981:139574, EPO Document No. XP002202947.

Goto, et al.:"Studies on Azole Compounds.III.1 Reactions of Oxazole N-Oxides with Phosphoryl Chloride and Acetic Anhydride 2", Chem. Pharm. Bull. 1971, 19: 2050-2057.

Ibrahim, et al.:"Synthesis and Biological Activity of Some New Heterocyclic Quinoline Derivatives," Phosphorus, Sulfer, and Silicon, 1991, 57: 293-301.

Jacobson, et al.:"Adenosine Receptor Ligands: Differences with Acute Versus Chronic Treatment," Trends in Pharmacological Sciences, Mar. 1996, 17(3):108-113.

Jacobson, et al,:"Adenosine Receptors as Theraputic Targets," Nat. Rev. Drug Discover.,2005, 5:247-264.

Kambe, et al.:"Synthetic Studies Using α,β-Unsaturated Nitriles: Facile Synthesis of Pyridine Derivatives," Synthesis Communications, Jul. 1981, pp. 531-533.

Müller, et al.:"Adenosine Receptor Antagonists: Structures and Potential Therapeutic Applications," Current Pharmaceutical Design, 1996, 2:501-530.

Müller:"Adenosine Receptor Ligands-Recent Developments Part I. Agonists," Current Medicinal Chemistry, 2000, 7:1269-1288.

Müller:"Review. Cardiovascular & Renal. A1-Adenosine Receptor Antagonists," Exp. Opin. Ther. Patents, 1997, 7 (5):419-440.

Inotek Pharmaceuticals Press Release, "Inotek Pharmaceuticals Initiates Multiple-Dose Phase 2 Clinical Trial of INO-8875 in Patients with Glaucoma," Jun. 17, 2010.

Patani, et al.: "Bioisosterism: A Rational Approach in Drug Design," Chem. Rev., 1996, 96:3147-3176.

Pflueger, et al.:"Role of Adenosine in Contrast Media-Induced Acute Renal Failure in Diabetes Mellitus," Mayo Clin Proc., Dec. 2000, 75(12):1275-1283.

Quintela, et al.:"Reactivity of Heterocyclic Compounds. V. Behavior of 6-alkoxy-2-amino-(or chloro)-4-aryl-3,5-dicyanopyridines in the Presence of Nucleophiles," Anales de Quimica, Serie C: Quimica Organica y Bioquimica, 1984, 80(3):268-72, English language abstract retrieved from CAPLUS Accession No. 1985:437345, CAPLUS Document No. 103:37345, EPO Document No. XP002202945.

Quintela, et al.:"Synthesis, Antihistaminic and Cytotoxic Activity of Pyridothieno- and Pyridodithienotriazines", Eur. J. Med. Chem, 1998, 33:887-897.

Rodinovskaya, et al.:"Substituted 4-(3-Cyanopyridin-2-ylthio)acetoacetates: New Convenient Reagents for the Synthesis of Heterocycles," Synthesis, 2006, (14): 2357-2370.

Rosenman:"Do Environmental Effects on Human Emotions Cause Cardiovascular Disorders?," Acta Physiologica Scandinavica, Supplement,1997, 161/640 (133-136), abstract retrieved from EMBASE Accession No. 97358868.

Ruhe, et al.:"Use of Antioxidant Nutrients in the Prevention and Treatment of Type 2 Diabetes," Journal of the American College of Nutrition, 2001, 20(5): 363S-369S.

Shams, et al.:"Nitriles in Organic Synthesis. New Routes for Synthesis of Pyridines and Azinothiopyrans," Journal fuer Praktische Chemie (Leipzig), 1988, 330(5):817-13, abstract retrieved from CAPLUS Accession No. 1989:497050.

(56) References Cited

OTHER PUBLICATIONS

Sheridan:"The Most Common Chemical Replacements in Drug-Like Compounds," J Chem. Inf. Comput. Sci., 2002, 42:103-108.
Suttner, et al.:"The Heart in the Elderly Critically ill Patient," Curr. Opin. Crit. Care, Oct. 2002, 8(5):389-94, abstract retrieved from MEDLINE Accession No. 2002495386, PubMed ID: 12357105.
Szydlowski, et al.:"Biological Role of Chromium," Diabetologia Polska, 2003, 10(3):365-370, English language abstract retrieved from EMBASE Accession No. 2004016455.
Vasudevan A. et al., "Aminopiperidine indazoles as orally efficacious melanin concentrating hormone receptoer-1 antagonists," Bioorg. Med. Chem. Lett. 2005, 15 (23), 5293-5297.
Vippagunta, et al.:"Crystalline Solids," Advanced Drug Delivery Reviews, May 16, 2001, 48(1):3-26.
West:"Solid State Chemistry and its Applications," Wiley, New York, 1988, pp. 358 & 365.
Ye, et al.:Organic Synthesis with $\alpha$-Diazocarbonyl Compounds, Chem. Rev. 1994, 94:1091-1160.
Yu, et al:"Physical Characterization of Polymorphic Drugs: An Integrated Characterization Strategy," Pharmaceutical Science & Technology Today, Jun. 1998, 1(3):118-127.
Zhu, G. et al., "Design and synthesis of pyridine-pyrazolopyridine-based inhibitors of protein kinase B/Akt," Bioorg. Med. Chem. 2007, 15 (6), 2441-2452.
Klotz:"Adenosine Receptors and their Ligands," Naunyn-Schmiedeberg's Arch. Pharmacol., 2000, 362: 382-391.
U.S. Appl. No. 13/210,889, filed Aug. 16, 2011.

\* cited by examiner

SUBSTITUTED BIPYRIDINE DERIVATIVES AND THEIR USE AS ADENOSINE RECEPTOR LIGANDS

The present invention relates to novel substituted 2,4'- and 3,4'-bipyridine derivatives, to processes for their preparation, to their use for the treatment and/or prophylaxis of diseases and to their use for preparing medicaments for the treatment and/or prophylaxis of diseases, preferably for the treatment and/or prevention of hypertension and other cardiovascular disorders.

Adenosine, a purine nucleoside, is present in all cells and is released by a large number of physiological and pathophysiological stimuli. Adenosine is formed intracellularly as an intermediate during the degradation of adenosine-5'-monophosphate (AMP) and S-adenosylhomocysteine, but it can be released from the cell, in which case it acts as a hormone-like substance or neurotransmitter for binding to specific receptors.

Under normoxic conditions, the concentration of free adenosine in the extracellular space is very low. However, under ischaemic or hypoxic conditions, the extracellular concentration of adenosine in the affected organs is increased dramatically. Thus, it is known, for example, that adenosine inhibits platelet aggregation and increases the blood supply to the coronary arteries. Furthermore, it acts on blood pressure, on the heart rate, on the release of neurotransmitters and on lymphocyte differentiation. In adipocytes, adenosine can inhibit lipolysis and thus increase the concentration of free fatty acids and triglycerides in the blood.

The aim of these actions of adenosine is to increase the oxygen supply of the affected organs and/or to reduce the metabolism of these organs in order to adjust the metabolism of the organ to the blood supply of the organ under ischaemic or hypoxic conditions.

The action of adenosine is mediated via specific receptors. To date, subtypes, A1, A2a, A2b and A3 are known. According to the invention, "adenosine receptor-selective ligands" are substances which bind selectively to one or more subtypes of the adenosine receptors, thus either mimicking the action of adenosine (adenosine agonists) or blocking its action (adenosine antagonists).

The actions of these adenosine receptors are mediated intracellularly by the messenger cAMP. In the case of the binding of adenosine to the A2a or A2b receptors, the intracellular cAMP is increased via activation of the membrane-bound adenylate cyclase, whereas binding of adenosine to the A1 or A3 receptors results in a decrease of the intracellular cAMP concentration via inhibition of adenylate cyclase.

In the cardiovascular system, the main consequences of the activation of adenosine receptors are: bradycardia, negative inotropism and protection of the heart against ischaemia ("preconditioning") via A1 receptors, dilation of the blood vessels via A2a and A2b receptors and inhibition of the fibroblasts and smooth-muscle-cell proliferation via A2b receptors.

In the case of A1 agonists (coupling preferably via G, proteins), a decrease of the intracellular cAMP concentration is observed (preferably after direct prestimulation of adenylate cyclase by forskolin). Correspondingly, A2a and A2b agonists (coupling preferably via $G_s$ proteins) leads to an increase and A2a and A2b antagonists to a decrease of the cAMP concentration in the cells. In the case of A2 receptors, a direct prestimulation of adenylate cyclase by forskolin is of no benefit.

The activation of A2b receptors by adenosine or specific A2b agonists leads, via dilation of blood vessels, to a lowering of the blood pressure. The lowering of the blood pressure is accompanied by a reflectory increase in heart rate. The increased heart rate can be reduced by activation of A1 receptors using specific A1 agonists.

The combined action of selective A1/A2b agonists on the vascular system and heart rate thus results in a systemic lowering of the blood pressure without relevant heart-rate increase. Dual A1/A2b agonists having such a pharmacological profile can be employed, for example, for treating hypertension in humans.

In adipocytes, activation of A1 and A2b receptors leads to an inhibition of lipolysis. Thus, the combined effect of A1/A2b agonists on lipid metabolism is a lowering of free fatty acids and triglycerides. Lowering of lipids, in turn, leads to a reduced insulin resistance and to alleviated symptoms in patients suffering from metabolic syndrome and in diabetics.

The abovementioned receptor selectivity can be determined by the effect of the substances on cell lines which, after stable transfection with the corresponding cDNA, express the receptor subtypes in question (see the publication M. E. Olah, H. Ren, J. Ostrowski, K. A. Jacobson, G. L. Stiles, "Cloning, expression, and characterization of the unique bovine A1 adenosine receptor. Studies on the ligand binding site by site-directed mutagenesis", *J. Biol. Chem.* 267 (1992), pages 10 764-10 770, the disclosure of which is hereby fully incorporated by way of reference).

The effect of the substances on such cell lines can be monitored by biochemical measurement of the intracellular messenger cAMP (see the publication K. N. Klotz, J. Hessling, J. Hegler, C. Owman, B. Kull, B. B. Fredholm, M. J. Lohse, "Comparative pharmacology of human adenosine receptor subtypes—characterization of stably transfected receptors in CHO cells", *Naunyn Schmiedebergs Arch. Pharmacol.* 357 (1998), pages 1-9, the disclosure of which is hereby fully incorporated by way of reference).

The "adenosine receptor-specific" ligands known from the prior art are mainly derivatives based on natural adenosine [S.-A. Poulsen and R. J. Quinn, "Adenosine receptors: New opportunities for future drugs", *Bioorganic and Medicinal Chemistry* 6 (1998), pages 619-641]. However, most of these adenosine ligands known from the prior art have the disadvantage that their action is not really receptor-specific, that their activity is less than that of natural adenosine or that they have only very weak activity after oral administration. Thus, they are mainly used only for experimental purposes.

WO 01/25210 and WO 02/070485 disclose substituted 2-thio-3,5-dicyano-4-aryl-6-aminopyridines as adenosine receptor ligands for treating disorders. WO 03/053441 discloses specifically substituted 2-thio-3,5-dicyano-4-phenyl-6-aminopyridines as selective ligands of the adenosine A1 receptor, and WO 2006/027142 claims substituted phenylaminothiazole derivatives as dual adenosine A1/A2b agonists for treating hypertension and other cardiovascular disorders. However, it was found that the solubility of these compounds in water and other physiological media is in some cases only very limited, which, for example, renders their formulation or else their parenteral administration difficult.

WO 01/62233 discloses various pyridine and pyrimidine derivatives and their use as adenosine receptor modulators. Substituted 3,5-dicyanopyridines as calcium-dependent potassium channel openers for the treatment of urological disorders are claimed in EP 1 302 463-A1. WO 2004/054505 claims the use of aminocyanopyridine derivatives as MK 2 inhibitors for the treatment of TNFα-mediated disorders. The use of 4-aryl- or 4-heteroaryl-substituted aminocyanopyridines as androgen receptor modulators is described in US 2005/0182105. WO 02/50071 discloses aminothiazole derivatives as tyrosine kinase inhibitors for the treatment of cancer and immunological and allergic disorders.

It is an object of the present invention to provide novel compounds which act as selective agonists of the adenosine A1 receptor, as selective agonists of the adenosine A2b receptor or as selective dual agonists of the adenosine A1 and A2b receptors and which, as such, are suitable for the treatment and/or prevention in particular of hypertension and other cardiovascular disorders, of the metabolic syndrome, of diabetes and dyslipidaemias and also for protecting organs during transplantations and surgical interventions, and which additionally have improved solubility in water and physiological media.

The present invention provides compounds of the formula (I)

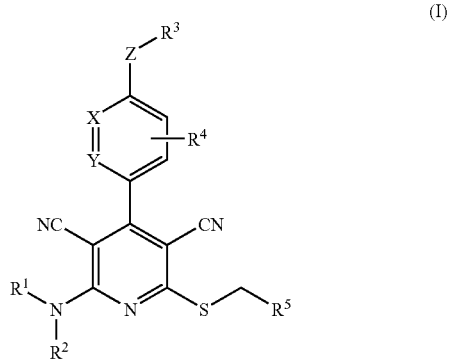

in which
one of the two ring members X and Y represents N and the other represents C—$R^6$, where
$R^6$ represents hydrogen or $(C_1-C_4)$-alkyl,
Z represents N—$R^7$ or O, where
$R^7$ represents hydrogen or $(C_1-C_4)$-alkyl which may be substituted by hydroxyl or $(C_1-C_4)$-alkoxy,
$R^1$ and $R^2$ are identical or different and independently of one another represent hydrogen or $(C_1-C_6)$-alkyl which may be mono- or disubstituted by identical or different substituents from a group consisting of hydroxyl, $(C_1-C_4)$-alkoxy, amino, mono-$(C_1-C_4)$-alkylamino, di-$(C_1-C_4)$-alkylamino, carboxyl, $(C_1-C_4)$-alkoxycarbonyl and a 4- to 7-membered heterocycle,
where the heterocycle mentioned contains one or two ring heteroatoms from the group consisting of N, O and S and for its part may be mono- or disubstituted by identical or different substituents from the group consisting of $(C_1-C_4)$-alkyl, hydroxyl, oxo and $(C_1-C_4)$-alkoxy,
or
$R^1$ and $R^2$ together with the nitrogen atom to which they are attached form a 4- to 7-membered heterocycle which may contain a further ring heteroatom from the group consisting of N, O and S and which may be mono- or disubstituted by identical or different substituents from the group consisting of $(C_1-C_4)$-alkyl, hydroxyl, oxo and $(C_1-C_4)$-alkoxy,
$R^3$ represents hydrogen or $(C_1-C_6)$-alkyl which may be mono- or disubstituted by identical or different substituents from the group consisting of $(C_3-C_6)$-cycloalkyl, oxo, hydroxyl, $(C_1-C_4)$-alkoxy, carboxyl, amino, mono-$(C_1-C_4)$-alkylamino and di-$(C_1-C_4)$-alkylamino, or represents $(C_4-C_6)$-cycloalkyl,
where the cycloalkyl radicals mentioned for their part may be substituted up to two times by identical or different substituents from the group consisting of $(C_1-C_4)$-alkyl, hydroxyl, oxo and $(C_1-C_4)$-alkoxy and where in these cycloalkyl radicals a ring $CH_2$-group may be replaced by an oxygen atom,
$R^4$ represents hydrogen, halogen, $(C_1-C_4)$-alkyl or $(C_1-C_4)$-alkoxy, where alkyl and alkoxy may each be substituted up to three times by fluorine,
and
$R^5$ represents $(C_6-C_{10})$-aryl or 5- to 10-membered heteroaryl having up to three ring heteroatoms from the group consisting of N, O and S, which may in each case
(i) be mono- or disubstituted by identical or different substituents from the group consisting of halogen, nitro, cyano, $(C_1-C_6)$-alkyl, phenyl, hydroxyl, $(C_1-C_6)$-alkoxy, amino, mono-$(C_1-C_6)$-alkylamino, mono-$(C_2-C_6)$-alkenylamino and di-$(C_1-C_6)$-alkylamino
and/or
(ii) be substituted by pyrrolidino, piperidino, morpholino, piperazino, N'—$(C_1-C_4)$-alkylpiperazino or a group of the formula -L-$R^8$, where
L represents a bond, NH or O
and
$R^8$ represents phenyl or 5- or 6-membered heteroaryl having up to three ring heteroatoms from the group consisting of N, O and S, each of which may be mono- to trisubstituted by identical or different substituents from the group consisting of halogen, nitro, cyano, $(C_1-C_6)$-alkyl, trifluoromethyl, hydroxyl, $(C_1-C_6)$-alkoxy, difluoromethoxy, trifluoromethoxy, amino, mono-$(C_1-C_6)$-alkylamino, di-$(C_1-C_6)$-alkylamino, $(C_1-C_6)$-alkoxycarbonyl and carboxyl,
and their salts, solvates and solvates of the salts.

Compounds according to the invention are the compounds of the formula (I) and the salts, solvates and solvates of the salts thereof, the compounds which are encompassed by the formula (I) and are mentioned in the formulae below, and the salts, solvates and solvates of the salts thereof, and the compounds which are encompassed by formula (I) and are mentioned below as exemplary embodiments, and the salts, solvates and solvates of the salts thereof, where the compounds which are encompassed by the formula (I) and are mentioned below are not already salts, solvates and solvates of the salts.

The compounds according to the invention may, depending on their structure, exist in stereoisomeric forms (enantiomers, diastereomers). The invention therefore encompasses the enantiomers or diastereomers and respective mixtures thereof. The stereoisomerically pure constituents can be isolated from such mixtures of enantiomers and/or diastereomers in a known manner.

Where the compounds according to the invention can exist in tautomeric forms, the present invention encompasses all tautomeric forms.

Salts preferred for the purposes of the present invention are physiologically acceptable salts of the compounds according to the invention. Also included are salts which are not themselves suitable for pharmaceutical applications but can be used, for example, for the isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases such as, by way of example and preferably, alkali metal salts (for example sodium and potassium salts), alkaline earth metal salts (for example calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refer for the purposes of the invention to those forms of the compounds according to the invention which form a complex in the solid or liquid state through coordination with solvent molecules. Hydrates are a specific form of solvates in which the coordination takes place with water. For the purposes of the present invention, preferred solvates are hydrates.

In addition, the present invention also encompasses prodrugs of the compounds according to the invention. The term "prodrugs" encompasses compounds which for their part may be biologically active or inactive but are converted (for example metabolically or hydrolytically) into compounds according to the invention during their residence time in the body.

For the purposes of the present invention, the substituents have the following meaning, unless specified otherwise:

For the purposes of the invention, $(C_1-C_6)$-alkyl, $(C_1-C_4)$-alkyl and $(C_1-C_3)$-alkyl represent a straight-chain or branched alkyl radical having 1 to 6, 1 to 4 and 1 to 3 carbon atoms, respectively. Preference is given to a straight-chain or branched alkyl radical having 1 to 4, particularly preferably 1 to 3, carbon atoms. The following radicals may be mentioned by way of example and by way of preference: methyl, ethyl, n-propyl, isopropyl, n-butyl, isobutyl, sec-butyl, tert-butyl, 1-ethylpropyl, n-pentyl and n-hexyl.

For the purposes of the invention, $(C_2-C_6)$-alkenyl represents a straight-chain or branched alkenyl radical having 2 to 6 carbon atoms and one or two double bonds. Preference is given to a straight-chain or branched alkenyl radical having 2 to 4 carbon atoms and one double bond. The following radicals may be mentioned by way of example and by way of preference: vinyl, allyl, isopropenyl, 2-methylprop-2-en-1-yl, n-but-2-en-1-yl and n-but-3-en-1-yl.

For the purposes of the invention, $(C_3-C_6)$-cycloalkyl, $(C_4-C_6)$-cycloalkyl and $(C_3-C_5)$-cycloalkyl represent a monocyclic saturated carbocycle having 3 to 6, 4 to 6 and 3 to 5 ring carbon atoms, respectively. The following radicals may be mentioned by way of example and by way of preference: cyclopropyl, cyclobutyl, cyclopentyl and cyclohexyl.

For the purposes of the invention, $(C_1-C_6)$-alkoxy, $(C_1-C_4)$-alkoxy and $(C_1-C_3)$-alkoxy represent a straight-chain or branched alkoxy radical having 1 to 6, 1 to 4 and 1 to 3 carbon atoms, respectively. Preference is given to a straight-chain or branched alkoxy radical having 1 to 4, particularly preferably 1 to 3, carbon atoms. The following radicals may be mentioned by way of example and by way of preference: methoxy, ethoxy, n-propoxy, isopropoxy, n-butoxy, tert-butoxy, n-pentoxy and n-hexoxy.

For the purposes of the invention, $(C_1-C_6)$-alkoxycarbonyl and $(C_1-C_4)$-alkoxycarbonyl represent a straight-chain or branched alkoxy radical having 1 to 6 and 1 to 4 carbon atoms, respectively, which is attached via a carbonyl group. Preference is given to a straight-chain or branched alkoxycarbonyl radical having 1 to 4 carbon atoms in the alkoxy group. The following radicals may be mentioned by way of example and by way of preference: methoxycarbonyl, ethoxycarbonyl, n-propoxycarbonyl, isopropoxycarbonyl and tert-butoxycarbonyl.

For the purposes of the invention, mono-$(C_1-C_6)$-alkylamino, mono-$(C_1-C_4)$-alkylamino and mono-$(C_1-C_3)$-alkylamino represent an amino group having a straight-chain or branched alkyl substituent having 1 to 6, 1 to 4 and 1 to 3 carbon atoms, respectively. Preference is given to a straight-chain or branched monoalkylamino radical having 1 to 4, particularly preferably 1 to 3, carbon atoms. The following radicals may be mentioned by way of example and by way of preference: methylamino, ethylamino, n-propylamino, isopropylamino, n-butylamino, tert-butylamino, n-pentylamino and n-hexylamino.

For the purposes of the invention, mono-$(C_2-C_6)$-alkenylamino represents an amino group having a straight-chain or branched alkenyl substituent having 2 to 6 carbon atoms. Preference is given to a straight-chain or branched monoalkenylamino radical having 1 to 4 carbon atoms. The following radicals may be mentioned by way of example and by way of preference: allylamino, 1-methylprop-2-en-1-ylamino, 2-methylprop-2-en-1-ylamino, but-2-en-1-ylamino and but-3-en-1-ylamino.

For the purposes of the invention, di-$(C_1-C_6)$-alkylamino, di-$(C_1-C_4)$-alkylamino and di-$(C_1-C_3)$-alkylamino represent an amino group having two identical or different straight-chain or branched alkyl substituents having in each case 1 to 6, 1 to 4 and 1 to 3 carbon atoms, respectively. Preference is given to straight-chain or branched dialkylamino radicals having in each case 1 to 4, particularly preferably in each case 1 to 3, carbon atoms. The following radicals may be mentioned by way of example and by way of preference: N,N-dimethylamino, N,N-diethylamino, N-ethyl-N-methylamino, N-methyl-N-n-propylamino, N-isopropyl-N-n-propylamino, N,N-diisopropylamino, N-n-butyl-N-methylamino, N-tert-butyl-N-methylamino, N-ethyl-N-n-pentylamino and N-n-hexyl-N-methylamino.

For the purposes of the invention, $(C_6-C_{10})$-aryl represents an aromatic carbocycle having 6 or 10 ring carbon atoms. Preferred aryl radicals are phenyl and naphthyl.

For the purposes of the invention, a 4- to 7-membered heterocycle represents a saturated heterocycle having a total of 4 to 7 ring atoms which contains one or two ring heteroatoms from the group consisting of N, O and S and which is attached via a ring carbon atom or, if appropriate, a ring nitrogen atom. Preference is given to a 5- or 6-membered heterocycle having one or two ring heteroatoms from the group consisting of N and O. The following radicals may be mentioned by way of example: azetidinyl, oxetanyl, pyrrolidinyl, pyrazolidinyl, tetrahydrofuranyl, piperidinyl, piperazinyl, tetrahydropyranyl, morpholinyl, thiomorpholinyl, hexahydroazepinyl and hexahydro-1,4-diazepinyl. Preference is given to pyrrolidinyl, tetrahydrofuranyl, piperidinyl, piperazinyl, tetrahydropyranyl and morpholinyl.

For the purposes of the invention, 5- to 10-membered heteroaryl represents a mono- or, if appropriate, bicyclic aromatic heterocycle (heteroaromatic) having a total of 5 to 10 ring atoms which contains up to three identical or different ring heteroatoms from the group consisting of N, O and S and which is attached via a ring carbon atom or, if appropriate, via a ring nitrogen atom. The following radicals may be mentioned by way of example: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl, triazinyl, benzofuranyl, benzothienyl, benzimidazolyl, benzoxazolyl, benzothiazolyl, benzotriazolyl, indolyl, indazolyl, quinolinyl, isoquinolinyl, naphthyridinyl, quinazolinyl, quinoxalinyl, phthalazinyl, pyrazolo[3,4-b]pyridinyl. Preference is given to monocyclic 5- or 6-membered heteroaryl radicals having up to three ring heteroatoms from the group consisting of N, O and S, such as, for example, furyl, thienyl, thiazolyl, oxazolyl, isothiazolyl, isoxazolyl, pyrazolyl, imidazolyl, triazolyl, oxadiazolyl, thiadiazolyl, pyridyl, pyrimidinyl, pyridazinyl, pyrazinyl, triazinyl.

For the purpose of the invention, halogen includes fluorine, chlorine, bromine and iodine. Preference is given to chlorine or fluorine.

When radicals in the compounds according to the invention are substituted, the radicals may be mono- or polysubstituted, unless specified otherwise. For the purposes of the present invention, the meanings of all radicals which occur more than once are independent of one another. Preference is given to substitution by one, two or three identical or different substituents. Very particularly preferred is substitution by one or two identical or different substituents.

For the purposes of the present invention, preference is given to compounds of the formula (I) in which
one of the two ring members X and Y represents N and the other represents CH,
Z represents N—$R^7$ or O, where
$R^7$ represents hydrogen or methyl,
$R^1$ represents hydrogen or $(C_1-C_4)$-alkyl which may be substituted by hydroxyl, $(C_1-C_4)$-alkoxy, amino, mono-$(C_1-C_4)$-alkylamino, di-$(C_1-C_4)$-alkylamino, carboxyl, $(C_1-C_4)$-alkoxycarbonyl or a 5- or 6-membered heterocycle,
where the heterocycle mentioned contains one or two ring heteroatoms from the group consisting of N and O and for its part may be mono- or disubstituted by identical or different substituents from the group consisting of methyl, ethyl, hydroxyl, methoxy and ethoxy,
$R^2$ represents hydrogen or methyl
or
$R^1$ and $R^2$ together with the nitrogen atom to which they are attached form a 5- or 6-membered heterocycle which may contain a further ring heteroatom from the group consisting of N and O and which may be mono- or disubstituted by identical or different substituents from the group consisting of methyl, ethyl, hydroxyl, methoxy and ethoxy,
$R^3$ represents $(C_1-C_4)$-alkyl which may be mono- or disubstituted by identical or different substituents from the group consisting of $(C_3-C_5)$-cycloalkyl, oxo, hydroxyl, $(C_1-C_3)$-alkoxy, amino, mono-$(C_1-C_3)$-alkylamino and di-$(C_1-C_3)$-alkylamino, or represents cyclopentyl or cyclohexyl,
where the $(C_3-C_5)$-cycloalkyl, cyclopentyl and cyclohexyl radicals mentioned for their part may be substituted up to two times by identical or different substituents from the group consisting of hydroxyl and methoxy and in cyclopentyl and cyclohexyl a ring $CH_2$-group may be replaced by an oxygen atom,
$R^4$ represents hydrogen, fluorine or chlorine,
and
$R^5$ represents phenyl or 5- or 6-membered heteroaryl having up to three ring heteroatoms from the group consisting of N, O and S, which may in each case
(i) be mono- or disubstituted by identical or different substituents from the group consisting of fluorine, chlorine, cyano, $(C_1-C_4)$-alkyl, amino, mono-$(C_1-C_4)$-alkylamino and di-$(C_1-C_4)$-alkylamino
and/or
(ii) be substituted by morpholino, N'—$(C_1-C_4)$-alkylpiperazino or a group of the formula -L-$R^8$, where
L represents a bond or NH
and
$R^8$ represents phenyl or 5- or 6-membered heteroaryl having up to three ring heteroatoms from the group consisting of N, O and S, each of which may be mono- to trisubstituted by identical or different substituents from the group consisting of fluorine, chlorine, cyano, $(C_1-C_4)$-alkyl, trifluoromethyl, $(C_1-C_4)$-alkoxy, trifluoromethoxy and carboxyl,
and their salts, solvates and solvates of the salts.

For the purposes of the present invention, particular preference is given to compounds of the formula (I) in which
one of the two ring members X and Y represents N and the other represents CH,
Z represents NH or O,
$R^1$ represents hydrogen or $(C_1-C_4)$-alkyl which may be substituted by hydroxyl, $(C_1-C_4)$-alkoxy, amino, mono-$(C_1-C_4)$-alkylamino or di-$(C_1-C_4)$-alkylamino,
$R^2$ represents hydrogen or methyl
or
$R^1$ and $R^2$ together with the nitrogen atom to which they are attached form a pyrrolidino, piperidino, morpholino or piperazino ring, each of which may be mono- or disubstituted by identical or different substituents from the group consisting of methyl, ethyl, hydroxyl, methoxy and ethoxy,
$R^3$ represents $(C_1-C_4)$-alkyl which may be mono- or disubstituted by identical or different substituents from the group consisting of oxo, hydroxyl, methoxy, ethoxy and amino,
$R^4$ represents hydrogen,
and
$R^5$ represents phenyl or 5- or 6-membered heteroaryl having up to two ring heteroatoms from the group consisting of N, O and S which may in each case
(i) be mono- or disubstituted by identical or different substituents from the group consisting of fluorine, chlorine, cyano, $(C_1-C_4)$-alkyl and amino
and/or
(ii) be substituted by a group of the formula -L-$R^8$, where
L represents a bond or NH
and
$R^8$ represents phenyl or pyridyl, each of which may be mono- or disubstituted by identical or different substituents from the group consisting of fluorine, chlorine, cyano, methyl, trifluoromethyl and methoxy,
and their salts, solvates and solvates of the salts.

For the purposes of the present invention, very particular preference is given to compounds of the formula (I) in which
X represents N,
Y represents CH,
Z represents O,
$R^1$ represents hydrogen or $(C_1-C_4)$-alkyl which may be substituted by hydroxyl, $(C_1-C_4)$-alkoxy, amino, mono-$(C_1-C_4)$-alkylamino or di-$(C_1-C_4)$-alkylamino, R² represents hydrogen or methyl or R¹ and R² together with the nitrogen atom to which they are attached form a pyrrolidino, piperidino, morpholino, piperazino or N'-methylpiperazino ring, R³ represents 2-hydroxyethyl, 2-hydroxy-1-methylethyl, 2-hydroxypropyl, 2-hydroxy-2-methylpropyl, 3-hydroxypropyl or 2,3-dihydroxypropyl, R⁴ represents hydrogen, and R⁵ represents pyrazolyl, oxazolyl, thiazolyl, pyridyl or pyrimidinyl which may in each case (i) be substituted by methyl, ethyl or amino and (ii) be substituted by a group of the formula -L-R⁸, where L represents a bond or NH and R⁸ represents phenyl or pyridyl, each of which may be mono- or disubstituted by identical or different substituents from the group consisting of fluorine, chlorine, cyano, methyl and methoxy, and their salts, solvates and solvates of the salts.

For the purposes of the present invention, very particular preference is also given to compounds of the formula (I) in which one of the two ring members X and Y represents N and the other represents CH, Z represents NH or O, R¹ and R² each represent hydrogen, R³ represents 2-hydroxyethyl, 2-hydroxy-1-methylethyl, 2-hydroxypropyl, 2-hydroxy-2-methylpropyl, 3-hydroxypropyl, 2,3-dihydroxypropyl or acetyl, R⁴ represents hydrogen, and R⁵ represents oxazolyl, thiazolyl or pyridyl, each of which may be substituted by methyl, ethyl, amino or a group of the formula -L-R⁸, where L represents a bond or NH and R⁸ represents phenyl or pyridyl, each of which may be mono- or disubstituted by identical or different substituents from the group consisting of fluorine, chlorine, cyano, methyl and methoxy, and their salts, solvates and solvates of the salts.

Of particular importance here are compounds of the formula (I) in which

X represents N and

Y represents CH, and their salts, solvates and solvates of the salts.

The present invention furthermore provides a process for preparing the compounds of the formula (I) according to the invention, characterized in that a compound of the formula (II)

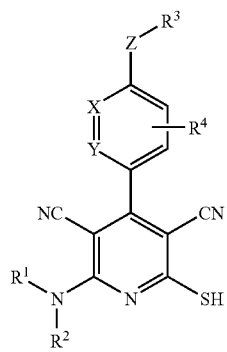

in which R¹, R², R³, R⁴, X, Y and Z are each as defined above is reacted in an inert solvent in the presence of a base with a compound of the formula (III)

in which R⁵ is as defined above and

Q represents a suitable leaving group, such as halogen, in particular chlorine, bromine or iodine, or represents mesylate, tosylate or triflate, and the resulting compounds of the formula (I) are, if appropriate, converted using the appropriate (i) solvents and/or (ii) bases or acids into their solvates, salts and/or solvates of the salts.

The process described above can be illustrated in an exemplary manner by the reaction scheme below:

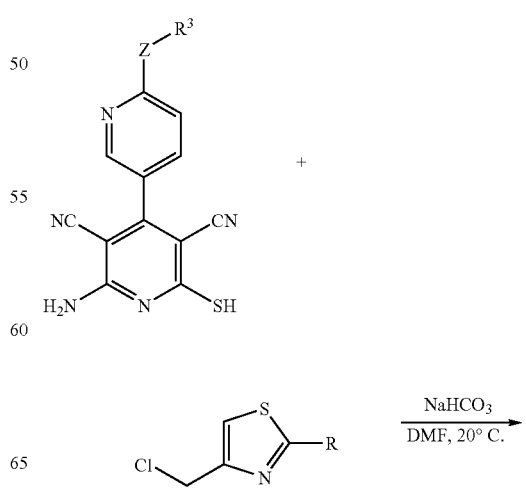

Scheme 1

-continued

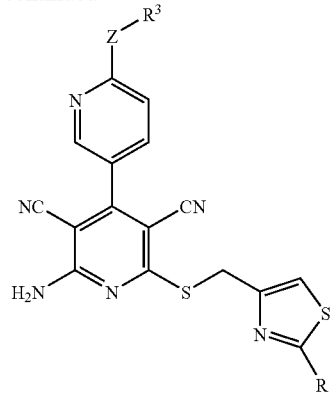

Suitable solvents for the process according to the invention are all organic solvents which are inert under the reaction conditions. These include alcohols, such as methanol, ethanol, n-propanol, isopropanol, n-butanol and tert-butanol, ketones, such as acetone and methyl ethyl ketone, acyclic and cyclic ethers, such as diethyl ether, methyl tert-butyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane, trichloromethane and chlorobenzene, or other solvents, such as dimethylformamide (DMF), dimethyl sulphoxide (DMSO), N-methylpyrrolidinone (NMP), acetonitrile or pyridine. Water is also suitable for use as solvent. It is also possible to use mixtures of the solvents mentioned above. The preferred solvent is dimethylformamide.

Suitable bases are the customary inorganic or organic bases. These preferably include alkali metal hydroxides, such as, for example, lithium hydroxide, sodium hydroxide or potassium hydroxide, alkali metal carbonates, such as lithium carbonate, sodium carbonate, potassium carbonate or caesium carbonate, alkali metal bicarbonates, such as sodium bicarbonate or potassium bicarbonate, alkali metal alkoxides, such as sodium methoxide or potassium methoxide, sodium ethoxide or potassium ethoxide or potassium tert-butoxide, amides, such as sodium amide, lithium bis(trimethylsilyl)amide, sodium bis(trimethylsilyl)amide or potassium bis(trimethylsilyl)amide or lithium diisopropylamide, organometallic compounds, such as butyllithium or phenyllithium, or organic amines, such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to alkali metal carbonates and alkali metal bicarbonates.

Here, the base can be employed in an amount of from 1 to 10 mol, preferably from 1 to 5 mol, in particular from 1 to 4 mol, based on 1 mol of the compound of the formula (II).

The reaction is generally carried out in a temperature range of from −78° C. to +140° C., preferably in the range from −20° C. to +60° C., in particular at from 0° C. to +40° C. The reaction can be carried out under atmospheric, elevated or reduced pressure (for example in the range from 0.5 to 5 bar). In general, the reaction is carried out under atmospheric pressure.

Compounds of the formula (II) in which $R^1$ and $R^2$ represent hydrogen can be prepared analogously to methods known from the literature, for example by reacting aldehydes of the formula (IV)

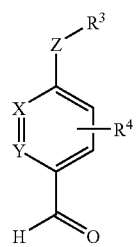

in which $R^3$, $R^4$, X, Y and Z are each as defined above in the presence of a base with two equivalents of cyanothioacetamide [see Scheme 2; cf., for example, Dyachenko et al., Russ. J. Chem. 33 (7), 1014-1017 (1997), 34 (4), 557-563 (1998); Dyachenko et al., Chemistry of Heterocyclic Compounds 34 (2), 188-194 (1998); Qintela et al., Eur. J. Med. Chem. 33, 887-897 (1998); Kandeel et al., Z. Naturforsch. 42b, 107-111 (1987); Reddy et al., J. Med. Chem. 49, 607-615 (2006); Evdokimov et al., Org. Lett. 8, 899-902 (2006)].

Scheme 2

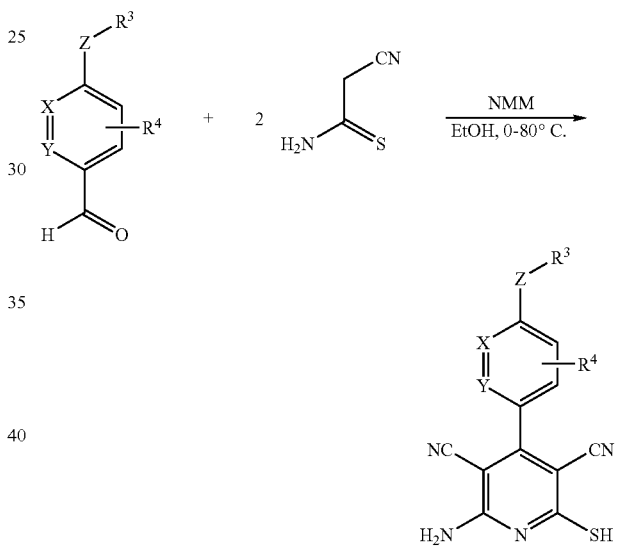

[EtOH = ethanol, NMM = N-methylmorpholine].

Compounds of the formula (II) in which $R^1$ and $R^2$ represent hydrogen can also be prepared starting with compounds of the formula (V)

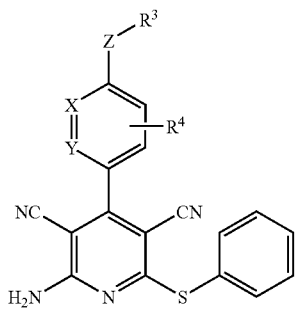

in which $R^3$, $R^4$, X, Y and Z are each as defined above by reaction with an alkali metal sulphide. This preparation method can be illustrated in an exemplary manner by the formula scheme below:

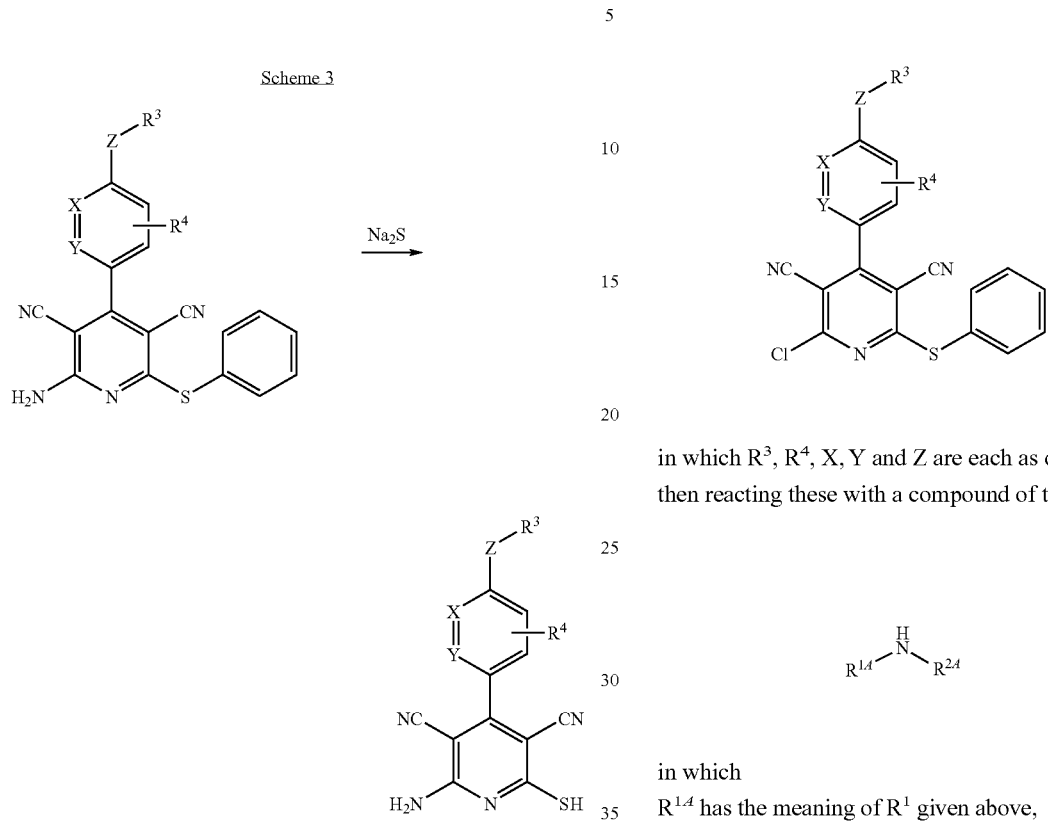

Preferred for use as alkali metal sulphide is sodium sulphide in an amount of from 1 to 10 mol, preferably from 1 to 5 mol, in particular from 1 to 4 mol, based on 1 mol of the compound of the formula (V).

Suitable solvents are all organic solvents which are inert under the reaction conditions. These preferably include dimethylformamide, N-methylpyrrolidinone, pyridine and acetonitrile. It is also possible to use mixtures of the abovementioned solvents. Particular preference is given to dimethylformamide.

The reaction is generally carried out in a temperature range of from +20° C. to +140° C., particularly preferably in the range of from +20° C. to +120° C., in particular at from +60° C. to +100° C. The reaction can be carried out under atmospheric, elevated or reduced pressure (for example in the range from 0.5 to 5 bar). In general, the reaction is carried out under atmospheric pressure.

The compounds of the formula (V) can be prepared analogously to processes described in the literature [cf., for example, Kambe et al., *Synthesis*, 531-533 (1981); Elnagdi et al., *Z. Naturforsch.* 47b, 572-578 (1991); Reddy et al., *J. Med. Chem.* 49, 607-615 (2006); Evdokimov et al., *Org. Lett.* 8, 899-902 (2006)].

Compounds of the formula (II) in which at least one of the two radicals $R^1$ and $R^2$ does not represent hydrogen can be prepared by initially converting compounds of the formula (V) with copper(II) chloride and isoamyl nitrite in a suitable solvent into compounds of the formula (VI)

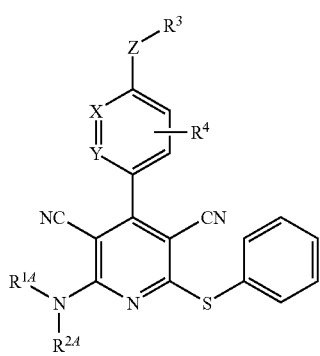

in which $R^3$, $R^4$, X, Y and Z are each as defined above, then reacting these with a compound of the formula (VII)

$$R^{1A}\overset{\overset{H}{|}}{N}R^{2A}$$ (VII)

in which $R^{1A}$ has the meaning of $R^1$ given above, $R^{2A}$ has the meaning of $R^2$ given above, but at least one of the two radicals does not represent hydrogen, to give compounds of the formula (VIII)

(VIII)

in which $R^{1A}$, $R^{2A}$, $R^3$, $R^4$, X, Y and Z are each as defined above, which are finally converted using an alkali metal sulphide into the compounds of the formula (II).

The process described above can be illustrated in an exemplary manner by the reaction scheme below:

Scheme 4

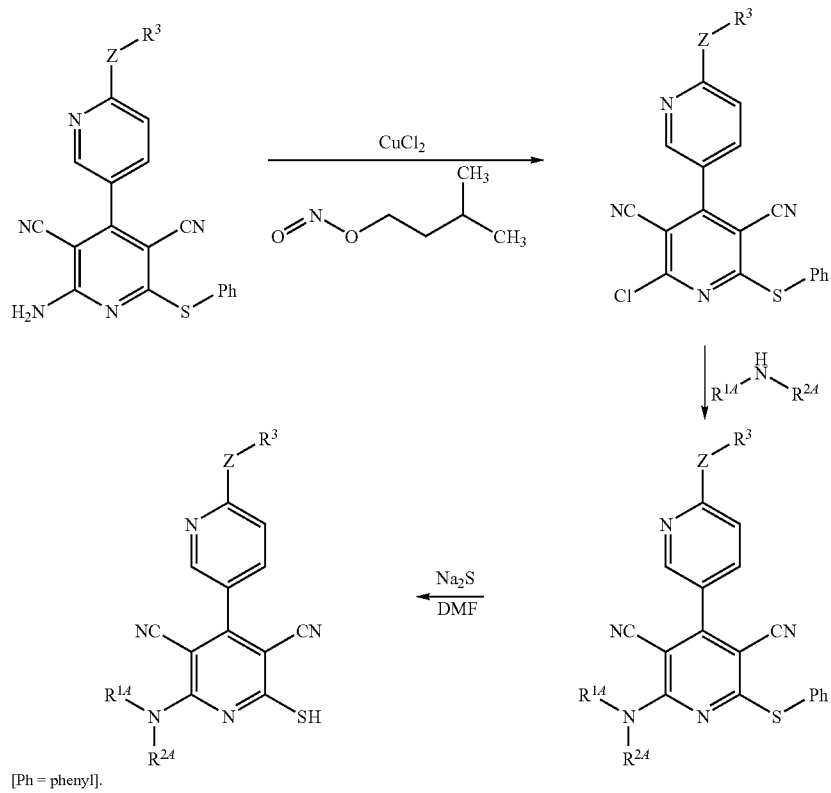

[Ph = phenyl].

The process step (V)→(VI) is generally carried out using a molar ratio of from 2 to 12 mol of copper(II) chloride and from 2 to 12 mol of isoamyl nitrite per mole of the compound of the formula (V).

Suitable solvents for this process step are all organic solvents which are inert under the reaction conditions. These include acyclic and cyclic ethers, such as diethyl ether and tetrahydrofuran, esters, such as ethyl acetate or butyl acetate, hydrocarbons, such as benzene, toluene, xylene, hexane and cyclohexane, chlorinated hydrocarbons, such as dichloromethane, 1,2-dichloroethane and chlorobenzene, or other solvents, such as dimethylformamide, acetonitrile or pyridine. It is also possible to use mixtures of the abovementioned solvents. Preferred solvents are acetonitrile and dimethylformamide.

The reaction is generally carried out in a temperature range of from −78° C. to +180° C., preferably in the range of from +20° C. to +100° C., in particular at from +20° C. to +60° C. The reaction can be carried out under atmospheric, elevated or reduced pressure (for example in the range from 0.5 to 5 bar). In general, the reaction is carried out under atmospheric pressure.

The process step (VI)+(VII)→(VIII) is generally carried out using a molar ratio of from 1 to 8 mol of the compound of the formula (VII) per mole of the compound of the formula (VI).

Suitable solvents for this process step are all organic solvents which are inert under the reaction conditions. These include alcohols, such as methanol, ethanol, n-propanol, isopropanol, n-butanol and tert-butanol, ketones, such as acetone and methyl ethyl ketone, acyclic and cyclic ethers, such as diethyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane, 1,2-dichloroethane and chlorobenzene, or other solvents, such as dimethylformamide, acetonitrile, pyridine or dimethyl sulphoxide. Another suitable solvent is water. It is also possible to use mixtures of the solvents mentioned above. The preferred solvent is dimethylformamide.

The reaction is generally carried out in a temperature range of from 0° C. to +180° C., preferably in the range of from +20° C. to +120° C., in particular at from +20° C. to +100° C. The reaction can be carried out under atmospheric, elevated or reduced pressure (for example in the range from 0.5 to 5 bar). In general, the reaction is carried out under atmospheric pressure.

The process step (VIII)→(II) is generally carried out using a molar ratio of from 1 to 8 mol of sodium sulphide per mole of the compound of the formula (VIII).

Solvents suitable for this process step are all inorganic solvents which are inert under the reaction conditions. These include alcohols, such as methanol, ethanol, n-propanol, isopropanol, n-butanol and tert-butanol, ketones, such as acetone and methyl ethyl ketone, acyclic and cyclic ethers, such as diethyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane, 1,2-dichloroethane and chlorobenzene, or other solvents, such as dimethylformamide, acetonitrile, pyridine, dimethyl sulphoxide or N-methylpyrrolidinone. Another suitable solvent is water. It is also possible to use mixtures of the solvents mentioned above. The preferred solvent is dimethylformamide.

The reaction is generally carried out in a temperature range of from 0° C. to +180° C., preferably in the range of from +20° C. to +120° C., in particular at from +40° C. to +100° C. The reaction can be carried out under atmospheric, elevated or reduced pressure (for example in the range from 0.5 to 5 bar). In general, the reaction is carried out under atmospheric pressure.

The compounds of the formula (VII) are either commercially available, known to the person skilled in the art or preparable by customary methods.

Analogously to the reaction sequence (V)→(VI)→(VIII), it is also possible to convert compounds of the formula (I) in which both $R^1$ and $R^2$ represent hydrogen into compounds of the formula (I) in which at least one of the two radicals $R^1$ and $R^2$ does not represent hydrogen. This is illustrated in the reaction scheme below:

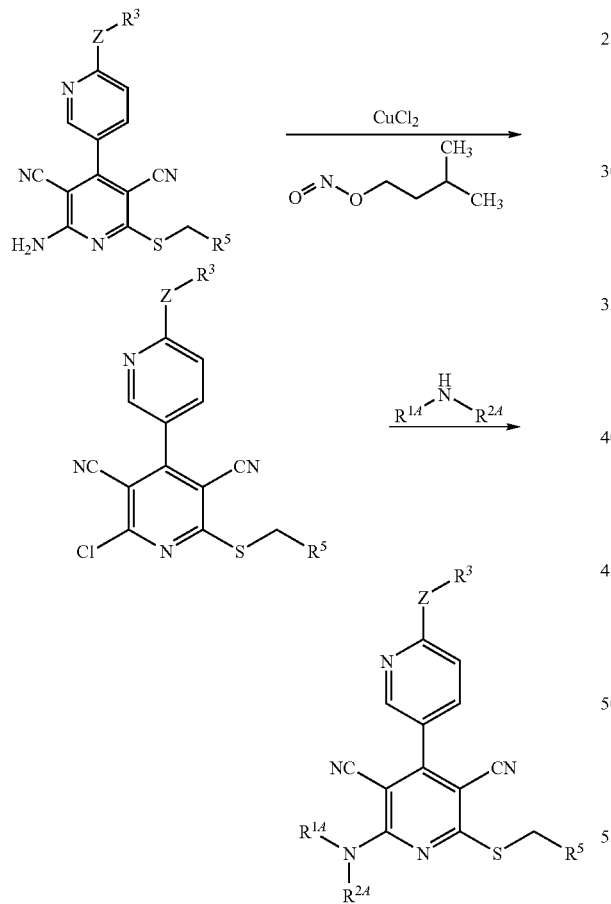

In this process variant, the reaction parameters described above for the sequence (V)→(VI)→(VIII), such as solvents, reaction temperatures and molar ratios, are used in an analogous manner.

The compounds of the formula (III) are likewise commercially available, known from the literature or preparable by methods known from the literature. Thus, for example, reaction of amides, thioamides or thiourea derivatives with a 1,3-dihaloacetone gives 2-substituted oxazole and thiazole derivatives of the formulae (III-A), (III-B) and (III-C), respectively (see Scheme 6):

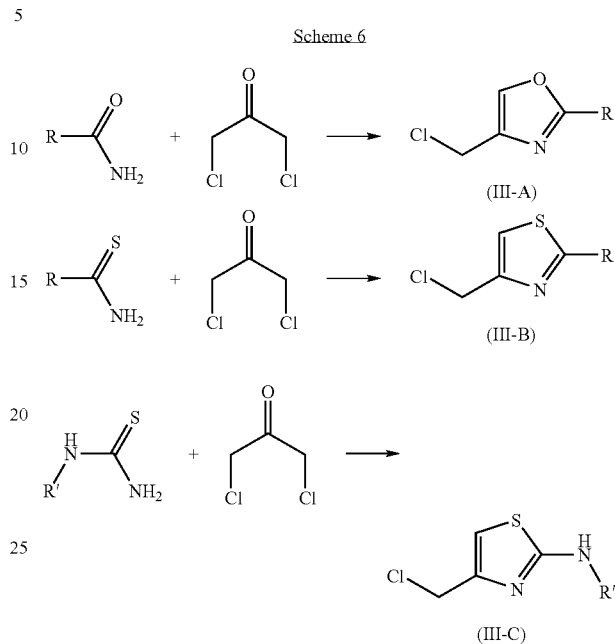

In the case of the compounds (III-C), these can either be prepared and isolated analogously to the literature (cf., for example, I. Simiti et al., Chem. Ber. 95, 2672-2679 (1962)], or they can be generated in situ and directly reacted further with a compound of the formula (II). Preference is given to the in situ-generation using 1,3-dichloroacetone in dimethylformamide or ethanol as solvent. The preparation is generally carried out in a temperature range of from 0° C. to +140° C., preferably in the range of from +20° C. to +120° C., in particular at from +60° C. to +100° C.

2,5-Disubstituted oxazole and thiazole derivatives according to formula (III) can be prepared analogously to processes known from the literature, for example as described in reaction schemes 7 and 8 below:

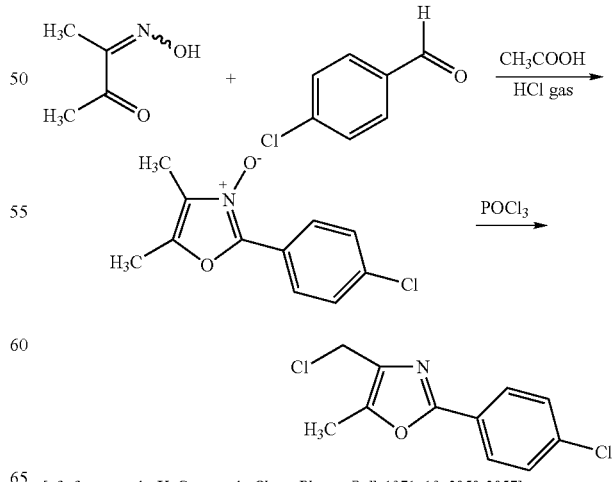

[cf., for example, Y. Goto et al., Chem. Pharm. Bull. 1971, 19, 2050-2057].

Scheme 8

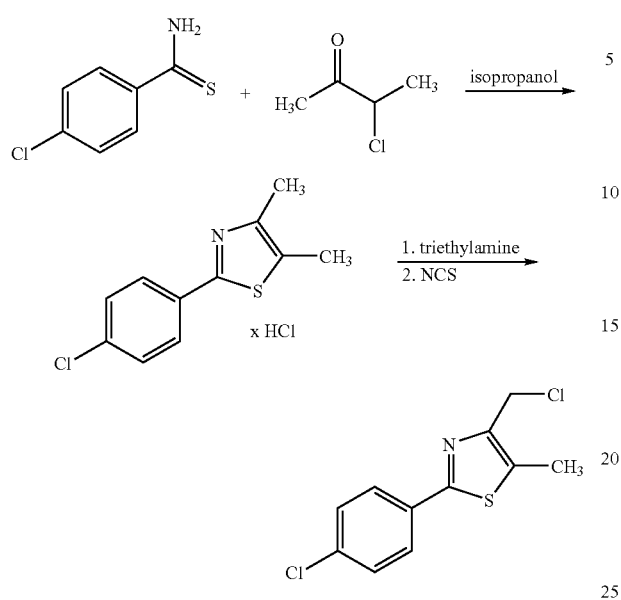

[NCS = N-chlorosuccinimide; cf., for example, T. Yamane et al., *Tetrahedron Lett.* 2004, 45, 69-73].

Oxazole derivatives according to formula (III), substituted in the 5-position, can be obtained, for example, by reduction and subsequent halogenation of corresponding oxazole-4-carboxylates which for their part are accessible by acylation of α-isocyanatoacetates (see Scheme 9):

Scheme 9

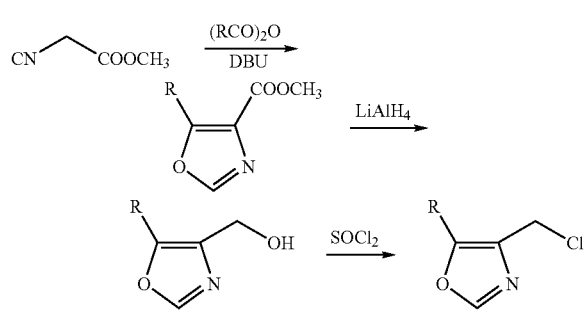

[DBU = 1,8-diazabicyclo[5.4.0]undec-7-ene; cf., for example, M. Suzuki et al., *J. Org. Chem.* 1973, 38, 3571-3575].

The compounds of the formula (IV) are known from the literature or can be prepared analogously to processes known from the literature, as shown in an exemplary manner in reaction schemes 10-13 below:

Scheme 10

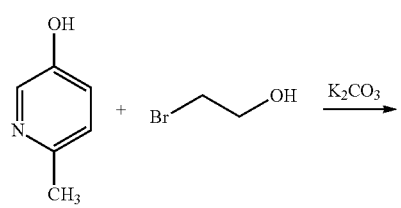

[Ac = acetyl, Ac$_2$O = acetic anhydride, mCPBA = meta-chloroperbenzoic acid; cf., for example, P. C.-M. Mao et al., *Chem. Pharm. Bull.* 2002, 50, 1634-1637; W. Hass et al., *Liebigs Ann. Chem.* 1982, 1615-1622; J. W. Ellingboe et al., *J. Med. Chem.* 1994, 37, 542-550].

Scheme 11

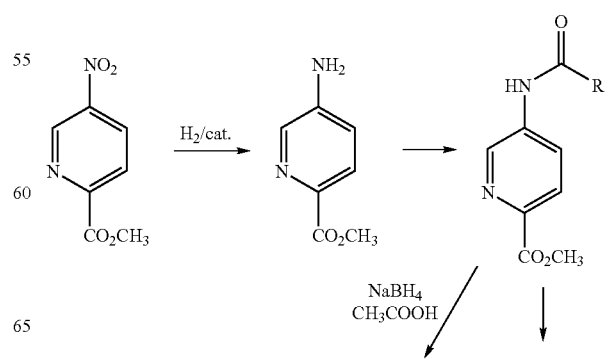

-continued

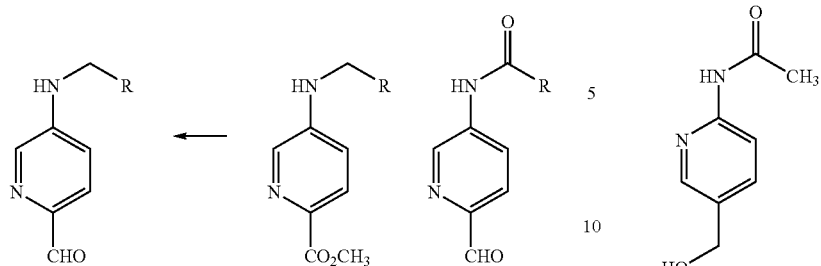

[Cat. = catalyst; cf., for example, N. Finch et al., *J. Med. Chem.* 1980, 23, 1405-1410; ibid. 1978, 21, 1269-1274].

Scheme 12

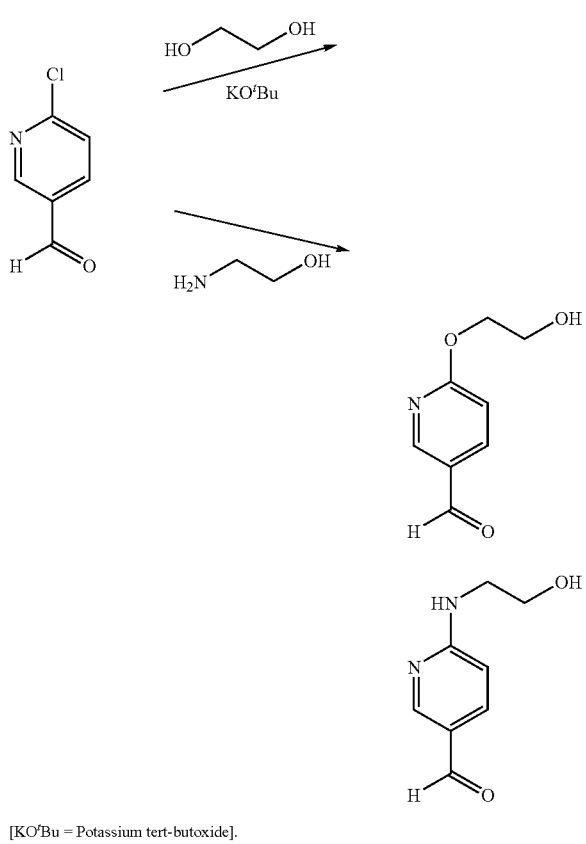

[KO$^t$Bu = Potassium tert-butoxide].

Scheme 13

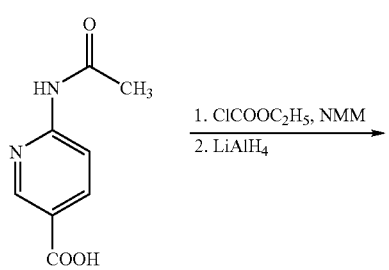

-continued

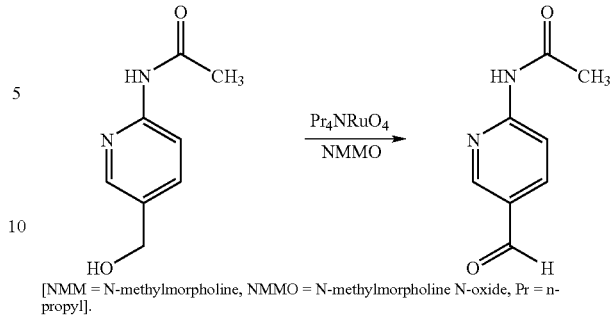

[NMM = N-methylmorpholine, NMMO = N-methylmorpholine N-oxide, Pr = n-propyl].

Surprisingly, the compounds according to the invention have an unforeseeable useful pharmacological activity spectrum and are therefore suitable in particular for the prophylaxis and/or treatment of disorders. In addition, the substances according to the invention have, compared to the compounds of the prior art, improved solubility in water and other physiological media, which is advantageous, for example, for ease of formulation and/or parenteral administration.

The pharmaceutical activity of the compounds according to the invention can be explained by their action as potent selective ligands on adenosine A1 and/or A2b receptors. Here, they act as selective A1, selective A2b or as selective dual A1/A2b agonists.

For the purpose of the present invention, "selective ligands on adenosine A1 and/or A2b receptors" are adenosine receptor ligands where on the one hand a clear activity can be observed on A1 and/or A2b adenosine receptor subtypes and on the other hand no or a considerably weaker activity (by a factor of 10 or higher) can be observed on A2a and A3 adenosine receptor subtypes, where, for the test methods for the selectivity of action, reference is made to the tests described in Section B-1.

The compounds of the formula (I), alone or in combination with one or more other active compounds, are suitable for the prophylaxis and/or treatment of various disorders, i.e. in particular, for example, hypertension and other disorders of the cardiovascular system (cardiovascular disorders), and also for cardio protection.

In the context of the present invention, disorders of the cardiovascular system or cardiovascular disorders are to be understood as meaning, in addition to hypertension, for example in particular the following disorders: peripheral and cardiovascular disorders, coronary heart disease, coronary restenosis, such as, for example, restenosis after balloon dilation of peripheral blood vessels, acute coronary syndrome, stable and unstable angina pectoris, heart failure, tachycardias, arrhythmias, atrial and ventricular fibrillation and also peripheral perfusion disorders.

The compounds according to the invention are furthermore also particularly suitable for reducing the size of the myocardial area affected by an infarct and for the prophylaxis of secondary infarcts.

Furthermore, the compounds according to the invention are particularly suitable, for example, for the prophylaxis and/or treatment of thromboembolic disorders and ischaemias, such as myocardial infarction, stroke and transitory ischaemic attacks, and also for protecting organs during transplantations and surgical interventions, for example at the heart.

Further areas of indication for which the compounds according to the invention are particularly suitable are, for example, the prophylaxis and/or treatment of disorders of the urogenital region, such as, for example, irritable bladder, erectile dysfunction and female sexual dysfunction, and additionally also the prophylaxis and/or treatment of inflammatory disorders, such as, for example, asthma and inflammable dermatoses, of neuroinflammatory disorders of the central nervous system, such as, for example, after cerebral infarction, Alzheimer's disease, furthermore also of neurodegenerative disorders, as well as of pain, cancer and nausea and vomiting associated with cancer therapies.

A further particular area of indication is, for example, the prophylaxis and/or treatment of disorders of the respiratory tract, such as, for example, asthma, chronic bronchitis, pulmonary emphysema, bronchiectases, cystic fibrosis (mucoviszidosis) and pulmonary hypertension.

Finally, the compounds according to the invention are in particular also suitable, for example, for the prophylaxis and/or treatment of diabetes, in particular diabetes mellitus, of diabetic sequelae, such as, for example, nephropathy and neuropathy, of the metabolic syndrome and also of dyslipidaemias.

The present invention also relates to the use of the compounds according to the invention for the treatment and/or prophylaxis of disorders, in particular the disorders mentioned above.

The present invention also relates to the use of the compounds according to the invention for preparing a medicament for the treatment and/or prophylaxis of disorders, in particular the disorders mentioned above.

The present invention furthermore relates to a method for the treatment and/or prophylaxis of disorders, in particular the disorders mentioned above, using an effective amount of at least one of the compounds according to the invention.

The compounds according to the invention can be used on their own or, if required, in combination with other active compounds. The present invention also relates to medicaments comprising at least one of the compounds according to the invention and one or more further active compounds, in particular for the treatment and/or prophylaxis of the disorders mentioned above.

Suitable active compounds for combinations are, by way of example and by way of preference: substances which modulate lipid metabolism, antidiabetics, hypotensive agents, perfusion-enhancing and/or antithrombotic agents, antioxidants, chemokine receptor antagonists, p38-kinase inhibitors, NPY agonists, orexin agonists, anorectics, PAF-AH inhibitors, antiphlogistics (COX inhibitors, LTB$_4$-receptor antagonists) and also analgesics such as, for example, aspirin.

The present invention provides in particular combinations comprising at least one of the compounds according to the invention and at least one lipid metabolism-modulating active compound, an antidiabetic, a hypotensive compound and/or antithrombotic agent.

Preferably, the compounds according to the invention can be combined with one or more
  lipid metabolism-modulating active compounds, by way of example and by way of preference from the group of the HMG-CoA reductase inhibitors, inhibitors of HMG-CoA reductase expression, squalene synthesis inhibitors, ACAT inhibitors, LDL receptor inductors, cholesterol absorption inhibitors, polymeric bile acid adsorbers, bile acid reabsorption inhibitors, MTP inhibitors, lipase inhibitors, LpL activators, fibrates, niacin, CETP inhibitors, PPAR-α, PPAR-γ and/or PPAR-δ agonists, RXR modulators, FXR modulators, LXR modulators, thyroid hormones and/or thyroid mimetics, ATP citrate lyase inhibitors, Lp(a) antagonists, cannabinoid receptor 1 antagonists, leptin receptor agonists, bombesin receptor agonists, histamine receptor agonists and the antioxidants/radical scavengers,
  antidiabetics mentioned in the Rote Liste 2004/II, chapter 12, and also, by way of example and by way of preference, those from the group of the sulphonylureas, biguanides, meglitinide derivatives, glucosidase inhibitors, oxadiazolidinones, thiazolidinediones, GLP 1 receptor agonists, glucagon antagonists, insulin sensitizers, CCK 1 receptor agonists, leptin receptor agonists, inhibitors of liver enzymes involved in the stimulation of gluconeogenesis and/or glycogenolysis, modulators of glucose uptake and also potassium channel openers, such as, for example, those disclosed in WO 97/26265 and WO 99/03861,
  hypotensives, by way of example and by way of preference from the group of the calcium antagonists, angiotensin AII antagonists, ACE inhibitors, beta-receptor blockers, alpha-receptor blockers, diuretics, phosphodiesterase inhibitors, sGC stimulators, cGMP level elevating substances, aldosterone antagonists, mineralocorticoid receptor antagonists, ECE inhibitors and the vasopeptidase inhibitors, and/or
  antithrombotic agents, by way of example and by way of preference from the group of the platelet aggregation inhibitors or the anticoagulants.

Lipid metabolism-modifying active compounds are to be understood as meaning, preferably, compounds from the group of the HMG-CoA reductase inhibitors, squalene synthesis inhibitors, ACAT inhibitors, cholesterol absorption inhibitors, MTP inhibitors, lipase inhibitors, thyroid hormones and/or thyroid mimetics, niacin receptor agonists, CETP inhibitors, PPAR-α agonists, PPAR-γ agonists, PPAR-δ agonists, polymeric bile acid adsorbers, bile acid reabsorption inhibitors, antioxidants/radical scavengers and also the cannabinoid receptor 1 antagonists.

In a preferred embodiment of the invention, the compounds according to the invention are administered in combination with an HMG-CoA reductase inhibitor from the class of the statins, such as, by way of example and by way of preference, lovastatin, simvastatin, pravastatin, fluvastatin, atorvastatin, rosuvastatin, cerivastatin or pitavastatin.

In a preferred embodiment of the invention, the compounds according to the invention are administered in combination with a squalene synthesis inhibitor, such as, by way of example and by way of preference, BMS-188494 or TAK-475.

In a preferred embodiment of the invention, the compounds according to the invention are administered in combination with an ACAT inhibitor, such as, by way of example and by way of preference, avasimibe, melinamide, pactimibe, eflucimibe or SMP-797.

In a preferred embodiment of the invention, the compounds according to the invention are administered in combination with a cholesterol absorption inhibitor, such as, by way of example and by way of preference, ezetimibe, tiqueside or pamaqueside.

In a preferred embodiment of the invention, the compounds according to the invention are administered in combination with an MTP inhibitor, such as, by way of example and by way of preference, implitapide, BMS-201038, R-103757 or JTT-130.

In a preferred embodiment of the invention, the compounds according to the invention are administered in combination with a lipase inhibitor, such as by way of example and by way of preference, orlistat.

In a preferred embodiment of the invention, the compounds according to the invention are administered in combination with a thyroid hormone and/or thyroid mimetic, such as, by way of example and by way of preference, D-thyroxine or 3,5,3'-triiodothyronine (T3).

In a preferred embodiment of the invention, the compounds according to the invention are administered in combination with an agonist of the niacin receptor, such as, by way of example and by way of preference, niacin, acipimox, acifran or radecol.

In a preferred embodiment of the invention, the compounds according to the invention are administered in combination with a CETP inhibitor, such as, by way of example and by way of preference, torcetrapib, JTT-705, BAY 60-5521, BAY 78-7499 or CETP vaccine (Avant).

In a preferred embodiment of the invention, the compounds according to the invention are administered in combination with a PPAR-γ agonist, such as, by way of example and by way of preference, pioglitazone or rosiglitazone.

In a preferred embodiment of the invention, the compounds according to the invention are administered in combination with a PPAR-δ agonist, such as, by way of example and by way of preference, GW-501516 or BAY 68-5042.

In a preferred embodiment of the invention, the compounds according to the invention are administered in combination with a polymeric bile acid adsorber, such as, by way of example and by way of preference, cholestyramine, colestipol, colesolvam, CholestaGel or colestimide.

In a preferred embodiment of the invention, the compounds according to the invention are administered in combination with a bile acid reabsorption inhibitor, such as, by way of example and by way of preference, ASBT (=IBAT) inhibitors, such as, for example, AZD-7806, S-8921, AK-105, BARI-1741, SC-435 or SC-635.

In a preferred embodiment of the invention, the compounds according to the invention are administered in combination with an antioxidant/radical scavenger, such as, by way of example and by way of preference, probucol, AGI-1067, BO-653 or AEOL-10150.

In a preferred embodiment of the invention, the compounds according to the invention are administered in combination with a cannabinoid receptor 1 antagonist, such as, by way of example and by way of preference, rimonabant or SR-147778.

Antidiabetics are to be understood as meaning, preferably, insulin and insulin derivatives, and also orally effective hypoglycaemic acid compounds. Here, insulin and insulin derivatives include both insulins of animal, human or biotechnological origin and also mixtures thereof. The orally effective hypoglycaemic active compounds preferably include sulphonylureas, biguanides, meglitinide derivatives, glucosidase inhibitors and PPAR-γ agonists.

In a preferred embodiment of the invention, the compounds according to the invention are administered in combination with insulin.

In a preferred embodiment of the invention, the compounds according to the invention are administered in combination with a sulphonylurea, such as, by way of example and by way of preference, tolbutamide, glibenclamide, glimepiride, glipizide or gliclazide.

In a preferred embodiment of the invention, the compounds according to the invention are administered in combination with a biguanide, such as, by way of example and by way of preference, metformin.

In a preferred embodiment of the invention, the compounds according to the invention are administered in combination with a meglitinide derivative, such as, by way of example and by way of preference, repaglinide or nateglinide.

In a preferred embodiment of the invention, the compounds according to the invention are administered in combination with a glucosidase inhibitor, such as, by way of example and by way of preference, miglitol or acarbose.

In a preferred embodiment of the invention, the compounds according to the invention are administered in combination with a PPAR-γ agonist, for example from the class of the thiazolidinediones, such as, by way of example and by way of preference, pioglitazone or rosiglitazone.

The hypotensive agents are preferably understood as meaning compounds from the group of the calcium antagonists, angiotensin AII antagonists, ACE inhibitors, beta-receptor blockers, alpha-receptor blockers and diuretics.

In a preferred embodiment of the invention, the compounds according to the invention are administered in combination with a calcium antagonist, such as, by way of example and by way of preference, nifedipine, amlodipine, verapamil or diltiazem.

In a preferred embodiment of the invention, the compounds according to the invention are administered in combination with an angiotensin AII antagonist, such as, by way of example and by way of preference, losartan, valsartan, candesartan, embusartan, olmesartan or telmisartan.

In a preferred embodiment of the invention, the compounds according to the invention are administered in combination with an ACE inhibitor, such as, by way of example and by way of preference, enalapril, captopril, lisinopril, ramipril, delapril, fosinopril, quinopril, perindopril or trandopril.

In a preferred embodiment of the invention, the compounds according to the invention are administered in combination with a beta-receptor blocker, such as, by way of example and by way of preference, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an alpha-receptor blocker, such as, by way of example and by way of preference, prazosin.

In a preferred embodiment of the invention, the compounds according to the invention are administered in combination with a diuretic, such as, by way of example and by way of preference, furosemide, bumetanide, torsemide, bendroflumethiazide, chlorothiazide, hydrochlorothiazide, hydroflumethiazide, methyclothiazide, polythiazide, trichloromethiazide, chlorothalidone, indapimide, metolazone, quinethazone, acetazolamide, dichlorophenamide, methazolamide, glycerol, isosorbide, mannitol, amiloride or triamterene.

In a preferred embodiment of the invention, the compounds according to the invention are administered in combination with antisympathotonics, such as reserpine, clonidine or alpha-methyldopa, with potassium channel-agonists, such as minoxidil, diazoxide, dihydralazine or hydralazine, or with nitrous oxide-releasing compounds, such as glycerol nitrate or sodium nitroprusside.

Antithrombotics are to be understood as meaning, preferably, compounds from the group of the platelet aggregation inhibitors or the anticoagulants.

In a preferred embodiment of the invention, the compounds according to the invention are administered in combination with a platelet aggregation inhibitor, such as, by way of example and by way of preference, aspirin, clopidogrel, ticlopidine or dipyridamol.

In a preferred embodiment of the invention, the compounds according to the invention are administered in combination with a thrombin inhibitor, such as, by way of example and by way of preference, ximelagatran, melagatran, bivalirudin or clexane.

In a preferred embodiment of the invention, the compounds according to the invention are administered in combination with a GPIIb/IIIa antagonist, such as, by way of example and by way of preference, tirofiban or abciximab.

In a preferred embodiment of the invention, the compounds according to the invention are administered in combination with a factor Xa inhibitor, such as, by way of example and by way of preference, rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX-9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, such as, by way of example and by way of preference, coumarin.

The present invention furthermore provides medicaments comprising at least one compound according to the invention, usually together with one or more inert non-toxic pharmaceutically suitable auxiliaries, and their use for the purposes mentioned above.

The compounds according to the invention can act systemically and/or locally. For this purpose, they can be administered in a suitable manner, such as, for example, orally, parenterally, pulmonally, nasally, sublingually, lingually, buccally, rectally, dermally, transdermally, conjunctivally, otically or as an implant or stent.

For these administration routes, the compounds according to the invention can be administered in suitable administration forms.

Suitable for oral administration are administration forms which work in accordance with the prior art and release the compounds according to the invention rapidly and/or in modified form and which comprise the compounds according to the invention in crystalline and/or amorphicized and/or dissolved form, such as, for example, tablets (uncoated or coated tablets, for example with enteric coats or coats which dissolve in a delayed manner or are insoluble and which control the release of the compounds according to the invention), films/wafers or tablets which dissolve rapidly in the oral cavity, films/lyophilizates, capsules (for example hard or soft gelatin capsules), sugar-coated tablets, granules, pellets, powders, emulsions, suspensions, aerosols or solutions.

Parenteral administration may take place by circumventing a bioabsorption step (for example intravenously, intraarterially, intracardially, intraspinally or intralumbarly), or with bioabsorption (for example intramuscularly, subcutaneously, intracutaneously, percutaneously or intraperitoneally). Administration forms suitable for parenteral administration are inter alia preparations for injection or infusion in the form of solutions, suspensions, emulsions, lyophilizates or sterile powders.

Suitable for other administration routes are, for example, medicaments suitable for inhalation (inter alia powder inhalers, nebulizers), nose drops, solutions or sprays, tablets to be administered lingually, sublingually or buccally, films/wafers or capsules, suppositories, preparations to be administered to ears or eyes, vaginal capsules, aqueous suspensions (lotions, shaking mixtures), lipophilic suspensions, ointments, creams, transdermal therapeutic systems (for example plasters), milk, pastes, foams, powders for pouring, implants or stents.

Preference is given to oral or parenteral administration, in particular to oral and intravenous administration.

The compounds according to the invention can be converted into the administration forms mentioned. This can be carried out in a manner known per se by mixing with inert non-toxic pharmaceutically suitable auxiliaries. These auxiliaries include inter alia carriers (for example microcrystalline cellulose, lactose, mannitol), solvents (for example liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides), and flavour and/or odour corrigents.

In general, it has been found to be advantageous in the case of parenteral administration to administer amounts of about 0.001 to 1 mg/kg, preferably about 0.01 to 0.5 mg/kg, of body weight to obtain effective results. In the case of oral administration, the dosage is from about 0.01 to 100 mg/kg, preferably from about 0.01 to 20 mg/kg and very particularly preferably from 0.1 to 10 mg/kg of body weight.

In spite of this, it may be necessary to deviate from the amounts mentioned, namely depending on body weight, administration route, individual response to the active compound, the type of preparation and the time or the interval at which administration takes place. Thus, in some cases it may be sufficient to administer less than the abovementioned minimum amount, whereas in other cases the upper limit mentioned has to be exceeded. In the case of the administration of relatively large amounts, it may be expedient to divide these into a plurality of individual doses which are administered over the course of the day.

The working examples below illustrate the invention. The invention is not limited to the examples.

The percentages in the tests and examples below are, unless indicated otherwise, percentages by weight; parts are parts by weight. Solvent ratios, dilution ratios and concentrations of liquid/liquid solutions are in each case based on volume.

A. EXAMPLES

| Abbreviations used: | |
|---|---|
| Ex. | example |
| TLC | thin-layer chromatography |
| DCI | direct chemical ionization (in MS) |
| DMF | N,N-dimethylformamide |
| DMSO | dimethyl sulphoxide |
| EA | ethyl acetate |
| EI | electron impact ionization (in MS) |
| ESI | electrospray ionization (in MS) |
| m.p. | melting point |
| sat. | saturated |
| h | hour(s) |
| HPLC | high-pressure, high-performance liquid chromatography |
| conc. | concentrated |
| LC-MS | liquid chromatography-coupled |

-continued

| | Abbreviations used: |
|---|---|
| | mass spectrometry |
| LDA | lithium diisopropylamide |
| Lit. | literature (reference) |
| sol. | solution |
| min | minute(s) |
| MS | mass spectrometry |
| NMR | nuclear magnetic resonance spectrometry |
| RP-HPLC | reverse phase HPLC |
| RT | room temperature |
| $R_t$ | retention time (in HPLC) |
| THF | tetrahydrofuran |
| dil. | diluted |
| aq. | aqueous |

HPLC and LC-MS Methods:

Method 1 (HPLC):
Instrument: Hewlett Packard Series 1050; column: Symmetry TM C18 3.9×150 mm; flow rate: 1.5 ml/min; mobile phase A: water, mobile phase B: acetonitrile; gradient: →0.6 min 10% B→3.8 min 100% B→5.0 min 100% B→5.5 min 10% B; Stop time: 6.0 min; Injection volume: 10 μl; diode array detector signal: 214 and 254 nm.

Method 2 (LC-MS):
Instrument: Micromass Quattro LCZ with HPLC Agilent Series 1100; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate 0.0 min 1 ml/min→2.5 min/3.0 min/4.5 min 2 ml/min; oven: 50° C.; UV detection: 208-400 nm.

Method 3 (LC-MS):
MS instrument type: Micromass ZQ; HPLC instrument type: Waters Alliance 2795; column: Phenomenex Synergi 2μ Hydro-RP Mercury 20 mm×4 mm; mobile phase A: 1 l of water+0.5 ml of 50% strength formic acid; mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 4 (LC-MS):
MS instrument type: Micromass ZQ; HPLC instrument type: HP 1100 Series; UV DAD; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 5 (LC-MS):
MS instrument type: Micromass ZQ; HPLC instrument type: Waters Alliance 2795; column: Merck Chromolith SpeedROD RP-18e 100 mm×4.6 mm; mobile phase A: water+500 μl of 50% strength formic acid/l, mobile phase B: acetonitrile+500 μl of 50% strength formic acid/l; gradient: 0.0 min 10% B→7.0 min 95% B→9.0 min 95% B; oven: 35° C.; flow rate: 0.0 min 1.0 ml/min→7.0 min 2.0 ml/min→9.0 min 2.0 ml/min; UV detection: 210 nm.

Method 6 (HPLC):
Instrument: HP 1100 with DAD detection; column: Kromasil RP-18, 60 mm×2 mm, 3.5 μm; mobile phase A: 5 ml of $HClO_4$/l of water, mobile phase B: acetonitrile; gradient: 0 min 2% B→0.5 min 2% B→4.5 min 90% B→9 min 90% B; flow rate: 0.75 ml/min; oven: 30° C.; UV detection: 210 nm.

Method 7 (HPLC):
Instrument: HP 1100 with DAD detection; column: Kromasil RP-18, 60 mm×2 mm, 3.5 μm; mobile phase A: 5 ml of $HClO_4$/l of water, mobile phase B: acetonitrile; gradient: 0 min 2% B→0.5 min 2% B→4.5 min 90% B→6.5 min 90% B; flow rate: 0.75 ml/min; oven: 30° C.; UV detection: 210 nm.

Method 8 (LC-MS):
MS instrument type: Micromass ZQ; HPLC instrument type: HP 1100 Series; UV DAD; column: Phenomenex Gemini 3μ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate 0.0 min 1 ml/min→2.5 min/3.0 min/4.5 min 2 ml/min; oven: 50° C.; UV detection: 210 nm.

Method 9 (LC-MS):
Instrument: Micromass Platform LCZ with HPLC Agilent Series 1100; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→0.2 min 100% A→2.9 min 30% A→3.1 min 10% A→5.5 min 10% A; flow rate: 0.8 ml/min; oven: 50° C.; UV detection: 210 nm.

Method 10 (LC-MS):
Instrument: Micromass Quattro LCZ with HPLC Agilent Series 1100; column: Phenomenex Onyx Monolithic C18, 100 mm×3 mm; mobile phase A: 1 l of water+0.5 ml of 50% strength formic acid, mobile phase B: 1 l acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 208-400 nm.

Method 11 (LC-MS):
Instrument: Micromass Quattro LCZ with HPLC Agilent Series 1100; column: Phenomenex Gemini 3μ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm.

Method 12 (LC-MS):
MS instrument type: Waters ZQ; HPLC instrument type: Waters Alliance 2795; column: Merck Chromolith RP18e, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 210 nm.

Method 13 (LC-MS):
Instrument: Micromass QuattroPremier with Waters UPLC Acquity; column: Thermo Hypersil GOLD 1.9μ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; oven: 50° C.; flow rate: 0.33 ml/min; UV detection: 210 nm.

Method 14 (LC-MS):
MS instrument type: Micromass ZQ; HPLC instrument type: Waters Alliance 2795; column: Phenomenex Synergi 2.5μ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 15 (LC-MS):

Instrument: Micromass Quattro LCZ with HPLC Agilent Series 1100; column: Phenomenex Synergi 2.5μ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.1 min 90% A; flow rate: 2 ml/min; oven: 50° C.; UV detection: 208-400 nm.

Method 16 (LC-MS):

Instrument: Micromass Quattro Micro MS with HPLC Agilent Series 1100; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Starting Materials and Intermediates:

Example 1A 6-(2-Hydroxyethoxy)nicotinaldehyde

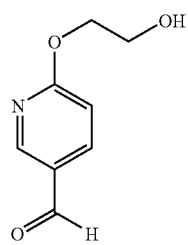 [SMILES: O=Cc1ccc(OCCO)nc1]

3.49 g (31.08 mmol) of potassium tert-butoxide are added to a solution of 3.51 g (56.51 mmol) of 1,2-ethanediol in 80 ml of dry DMF, and the mixture is stirred at RT for 15 min 4.0 g (28.26 mmol) of 6-chloronicotinaldehyde are then added. The reaction solution is stirred at RT for 20 h. The mixture is then poured into 200 ml of a 1:1 mixture of ethyl acetate and saturated sodium bicarbonate solution. The phases are separated, and the aqueous phase is then extracted with ethyl acetate (two times 100 ml each). The combined organic phases are washed with water (two times 100 ml each). The organic phase is dried over magnesium sulphate. After removal of the solvent on a rotary evaporator, the crude product is purified chromatographically on silica gel 60 (mobile phase: cyclohexane/ethyl acetate 2:1).

Yield: 2.83 g (46% of theory, 77% pure)

$^1$H-NMR (300 MHz, DMSO-$d_6$): δ=9.97 (s, 1H), 8.76 (d, 1H), 8.11 (d, 1H), 6.99 (d, 1H), 4.90 (t, 1H), 4.40 (t, 2H), 3.73 (dt, 2H).

LC-MS (Method 4): $R_t$=1.09 min; MS (ESIpos): m/z=168 [M+H]$^+$.

Example 2A

2'-Amino-6-(2-hydroxyethoxy)-6'-mercapto-3,4'-bipyridine-3',5'-dicarbonitrile

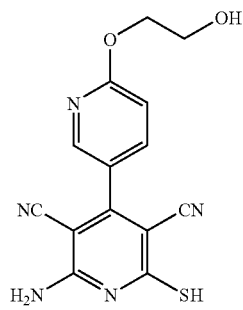

2.83 g (16.93 mmol) of the compound from example 1A, 3.39 g (33.86 mmol) of cyanothioacetamide and 3.42 g (33.86 mmol) of 4-methylmorpholine are dissolved in 65 ml of ethanol, and the mixture is stirred under reflux for 3 h and then at RT for 20 h. The reaction solution is concentrated on a rotary evaporator and the residue is purified chromatographically on silica gel 60 (mobile phase: gradient dichloromethane/ethanol 20:1→5:1).

Yield: 1.66 g (30% of theory)

$^1$H-NMR (300 MHz, DMSO-$d_6$): δ=8.29 (d, 1H), 7.88-7.81 (m, 1H), 7.60-7.41 (br. s, 2H), 6.98 (d, 1H), 4.89 (t, 1H), 4.40-4.32 (m, 2H), 3.79-3.65 (m, 2H).

LC-MS (Method 4): $R_t$=1.39 min; MS (ESIpos): m/z=314 [M+H]$^+$.

Example 3A

6-[(2-Hydroxyethyl)amino]nicotinaldehyde

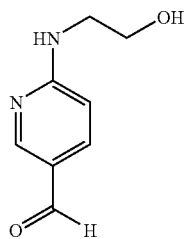 [SMILES: O=Cc1ccc(NCCO)nc1]

10.12 g (165.68 mmol) of 2-aminoethanol are added to 1.00 g (7.06 mmol) of 6-chloronicotinaldehyde, and the reaction mixture is then stirred at 135° C. for 14 h. This gives a yellow solution which is fractionated by distillation in a kugelrohr apparatus (2.2 mbar, 100° C.). The fraction comprising the desired product is then directly reacted further.

LC-MS (Method 9): $R_t$=1.51 min; MS (ESIpos): m/z=167 [M+H]$^+$.

Example 4A

2'-Amino-6-[(2-hydroxyethyl)amino]-6'-mercapto-3,4'-bipyridine-3',5'-dicarbonitrile

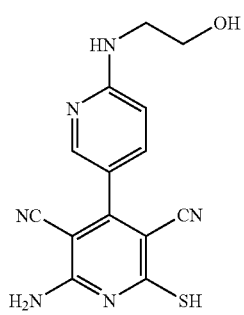

3.0 g of the crude product from example 3A, 3.62 g (36.11 mmol) of cyanothioacetamide and 3.65 g (36.11 mmol) of 4-methylmorpholine are dissolved in 50 ml of ethanol, and the mixture is stirred under reflux for 3 h and then at RT for 20 h. The reaction solution is concentrated on a rotary evaporator and the residue is chromatographed on silica gel 60 (mobile phase: gradient dichloromethane/ethanol 100:1→5:1). Several fractions comprising the desired product are obtained and directly reacted further.

LC-MS (Method 9): $R_t$=2.28 min; MS (ESIpos): m/z=313 [M+H]$^+$.

Example 5A (2-Chloro-6-methylpyrimidin-4-yl)methanol

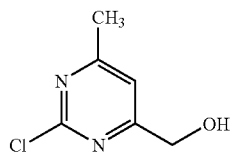

5.00 g (28.97 mmol) of 2-chloro-6-methylpyrimidine-4-carboxylic acid and 5.17 g (118.97 mmol) of thionyl chloride are initially charged in 60 ml of dry toluene and stirred at 60° C. for 3 h. The reaction solution is concentrated on a rotary evaporator, 20 ml of toluene are added to the residue and the mixture is again concentrated to dryness on a rotary evaporator. The residue is dissolved in 40 ml of methyl tert-butyl ether and cooled to 5° C. At this temperature, a solution of 2.41 g (63.74 mmol) of sodium borohydride in 40 ml of water is added. After warming to RT, the reaction mixture is kept at 4° C. for 24 h. 40 ml of ethyl acetate and 10 ml of sat. sodium bicarbonate solution are then added to the mixture. The organic phase is washed twice with in each case 10 ml of water. After drying of the organic phase over magnesium sulphate, the solvent is removed on a rotary evaporator.

Yield: 3.10 g (67% of theory)

LC-MS (Method 3): $R_t$=0.63 min; MS (ESIpos): m/z=159 [M+H]$^+$.

Example 6A

{2-[(4-Fluorophenyl)amino]-6-methylpyrimidin-4-yl}methanol

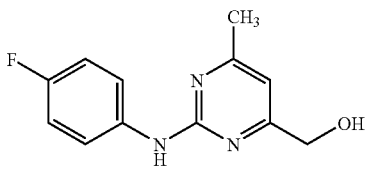 [SMILES: Cc1cc(CO)nc(Nc2ccc(F)cc2)n1]

50 mg (0.32 mmol) of the compound from example 5A and 350 mg (3.15 mmol) of 4-fluoroaniline are stirred together at 160° C. for 2 h. The reaction mixture is then poured into 10 ml of diethyl ether. The precipitate is filtered off and discarded and the filtrate is then purified chromatographically on silica gel 60 (mobile phase: gradient dichloromethane→dichloromethane/ethanol 50:1).

Yield: 37 mg (49% of theory)

LC-MS (Method 3): $R_t$=1.55 min; MS (ESIpos): m/z=234 [M+H]$^+$.

Example 7A 4-(Chloromethyl)-N-(4-fluorophenyl)-6-methylpyrimidine-2-amine

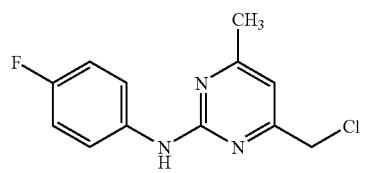 [SMILES: Cc1cc(CCl)nc(Nc2ccc(F)cc2)n1]

At 0° C., 225 mg (0.96 mmol) of the compound from example 6A and 137 mg (1.16 mmol) of thionyl chloride are initially charged in 10 ml of dichloromethane and, after warming to RT, stirred at this temperature for 24 h. The solvent is removed on a rotary evaporator and the product that remains is directly reacted further.

Yield: 242 mg (99% of theory)

LC-MS (Method 3): $R_t$=2.30 min; MS (ESIpos): m/z=252 [M+H]$^+$.

Example 8A

[6-(Pyridin-4-ylamino)pyridin-2-yl]methanol

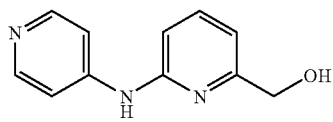 [SMILES: OCc1cccc(Nc2ccncc2)n1]

1.35 g (14.3 mmol) of 4-aminopyridine and 1.34 g (7.1 mmol) of (6-bromopyridin-2-yl)methanol are stirred at 150° C. for 4 h. After cooling to RT, 50 ml of acetonitrile are added to the reaction mixture, and the mixture is stirred for 20 min.

Example 9A 6-(Chloromethyl)-N-pyridin-4-yl-pyridine-2-amine

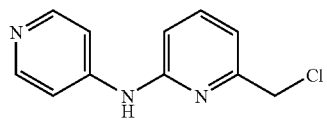 [SMILES: ClCc1cccc(Nc2ccncc2)n1]

At 0° C., 50 mg (0.22 mmol) of the compound from example 8A and 53 mg (0.44 mmol) of thionyl chloride are initially charged in 1.5 ml of dichloromethane and, after warming to RT, stirred at this temperature for 12 h. The solvent is removed on a rotary evaporator and the product that remains is directly reacted further.

Yield: 65 mg (99% of theory, 74% pure)

LC-MS (Method 9): $R_t$=2.26 min; MS (ESIpos): m/z=220 [M+H]$^+$.

Example 10A (6-Chloropyridazin-3-yl)methanol

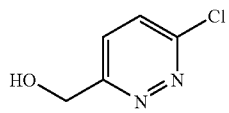

4.3 g (21.4 mmol) of 6-chloropyridazine-3-carboxylic acid are dissolved in 60 ml of dry toluene and heated to 60° C. At this temperature, 3.8 g (32.2 mmol) of thionyl chloride are added, and the mixture is stirred at this temperature for 3 h. The mixture is then heated at reflux for 4 h. After cooling to RT, the solvent is removed on a rotary evaporator. 20 ml of toluene are added, and the mixture is again evaporated to dryness. The residue is dissolved in 40 ml of methyl tert-butyl ether and cooled to 5° C. At this temperature, a solution of 1.7 g (47.2 mmol) of sodium borohydride in 37 ml of water is added dropwise. The mixture is stirred at RT for 20 h. 50 ml of ethyl acetate are then added, and the aqueous phase is extracted three times with in each case 10 ml of ethyl acetate. The combined organic phases are washed in each case twice with in each case 10 ml of sat. sodium bicarbonate solution and water. The solvent is removed on a rotary evaporator and the residue is purified chromatographically on silica gel 60 (mobile phase: gradient dichloromethane/ethanol 100:1→20:1).

Yield: 1.3 g (41% of theory)

LC-MS (Method 9): $R_t$=1.86 min; MS (ESIpos): m/z=144 [M+H]$^+$.

Example 11A

3-Chloro-6-(chloromethyl)pyridazine

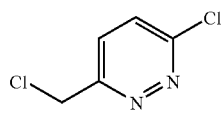

At 0° C., 200 mg (1.38 mmol) of the compound from example 10A and 198 mg (1.66 mmol) of thionyl chloride are initially charged in 1.5 ml of dichloromethane and, after warming to RT, stirred at this temperature for 24 h. The solvent is removed on a rotary evaporator and the product that remains is directly reacted further.

Yield: 225 mg (99% of theory)

Example 12A 1,1-Dimethoxy-4,4-bis(methylthio)but-3-en-2-one

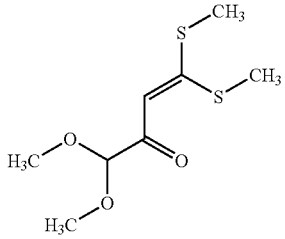

The title compound is prepared analogously to P. K. Mahata et al., *Tetrahedron* 59, 2631-2639 (2003):

Under argon, 8.0 g (200 mmol) of sodium hydride are initially charged in 250 ml of dry THF. At 0° C., a solution of 7.6 g (100 mmol) of carbon disulphide in 100 ml of THF is added dropwise. The mixture is stirred at this temperature for 30 minutes. Over a period of 30 min, 11.8 g (100 mmol) of methylglyoxal dimethyl acetal, dissolved in 100 ml of THF, is then added dropwise. The mixture is stirred at RT for 7 h. The mixture is then cooled to 0° C., and a solution of 35.5 g (250 mmol) of iodomethane in 50 ml of THF is added dropwise. After warming to RT, 50 ml of sat. ammonium chloride solution and 150 ml of ethyl acetate are added to the reaction mixture. The aqueous phase is extracted three times with in each case 20 ml of ethyl acetate and the combined organic phases are washed twice with in each case 25 ml of sat. sodium chloride solution. The solvent is removed on a rotary evaporator.

Yield: 11.2 g (50% of theory)

LC-MS (Method 4): $R_t$=1.77 min; MS (ESIpos): m/z=223 [M+H]$^+$.

---

The precipitate formed is filtered off with suction at 0° C. and washed with 10 ml of acetonitrile.

Yield: 1.25 g (39% of theory, 89% pure)

LC-MS (Method 9): $R_t$=1.76 min; MS (ESIpos): m/z=202 [M+H]$^+$.

Example 13A (3E)-4-[(4-Fluorophenyl)amino]-1,1-dimethoxy-4-(methylthio)but-3-en-2-one

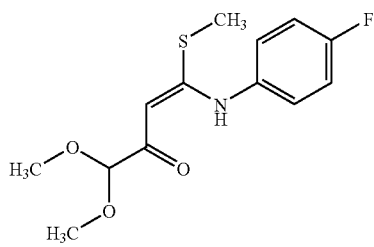 [SMILES: COC(OC)C(=O)/C=C(\Nc1ccc(F)cc1)SC]

The title compound is prepared analogously to P. K. Mahata et al., *Tetrahedron* 59, 2631-2639 (2003):

1.5 g (13.5 mmol) of 4-fluoroaniline are initially charged in 50 ml of THF. The solution is cooled to −78° C., and 12.7 ml (20.2 mmol) of a solution of n-butyllithium in hexane (1.6 M) are added carefully. The mixture is stirred at −78° C. for 30 min. Over a period of 20 min, a solution of 3.0 g (13.5 mmol) of the compound from example 12A in 25 ml of THF is then added dropwise. The mixture is allowed to warm to RT and is subsequently heated at reflux for 10 minutes. After cooling to RT, 30 ml of ethyl acetate and 20 ml of sat. sodium bicarbonate solution are added. The aqueous phase is extracted three times with in each case 20 ml of ethyl acetate. The organic phases are combined and the solvent is then removed under reduced pressure and the residue is purified chromatographically on silica gel 60 (mobile phase: gradient cyclohexane/ethyl acetate 10:1→2:1).

Yield: 3.3 g (77% of theory, 90% pure)

LC-MS (Method 2): $R_t$=2.17 min; MS (ESIpos): m/z=286 [M+H]$^+$.

Example 14A 3-(Dimethoxymethyl)-N-(4-fluorophenyl)-1H-pyrazole-5-amine

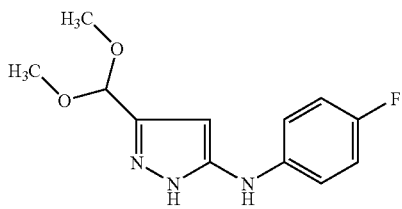 [SMILES: COC(OC)c1cc(Nc2ccc(F)cc2)[nH]n1]

The title compound is prepared analogously to P. K. Mahata et al., *Tetrahedron* 59, 2631-2639 (2003):

1.5 g (5.3 mmol) of the compound from example 13A and 263 mg (5.26 mmol) of hydrazine hydrate are dissolved in 40 ml of ethanol and heated at reflux for 2 h. The solvent is removed on a rotary evaporator and the residue is purified chromatographically on silica gel 60 (mobile phase: gradient cyclohexane/ethyl acetate 5:1→2:1).

Yield: 869 mg (64% of theory)

LC-MS (Method 3): $R_t$=1.67 min; MS (ESIpos): m/z=252 [M+H]$^+$.

Example 15A

5-[(4-Fluorophenyl)amino]-1H-pyrazole-3-carbaldehyde

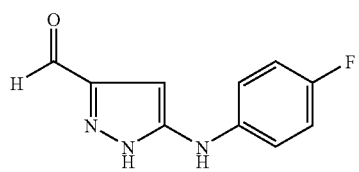 [SMILES: O=Cc1cc(Nc2ccc(F)cc2)[nH]n1]

The title compound is prepared analogously to P. K. Mahata et al., *Tetrahedron* 59, 2631-2639 (2003):

869 mg (3.35 mmol) of the compound from example 14A are dissolved in 10 ml of dichloromethane, and 16.8 ml of 2 N hydrochloric acid are added. The reaction mixture is stirred at RT for 1 h and in each case 10 ml of sat. sodium bicarbonate solution and ethyl acetate are then added. The mixture is adjusted to pH 8 using 1 N aqueous sodium hydroxide solution. The organic phase is separated off and dried over sodium sulphate. The solvent is removed on a rotary evaporator and the product that remains is directly reacted further.

Yield: 840 mg

LC-MS (Method 2): $R_t$=1.78 min; MS (ESIpos): m/z=206 [M+H]$^+$.

Example 16A

{5-[(4-Fluorophenyl)amino]-1H-pyrazol-3-yl}methanol

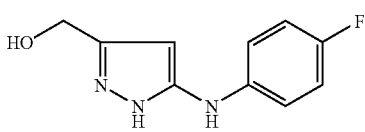 [SMILES: OCc1cc(Nc2ccc(F)cc2)[nH]n1]

The title compound is prepared analogously to P. K. Mahata et al., *Tetrahedron* 59, 2631-2639 (2003):

688 mg (3.36 mmol) of the compound from example 15A are dissolved in 20 ml of methanol, and 190 mg (5.03 mmol) of sodium borohydride are added. The reaction mixture is stirred at RT for 30 min. After addition of 10 ml of ethyl acetate and 5 ml of sat. sodium bicarbonate solution, the phases are separated and the aqueous phase is extracted three more times with in each case 5 ml of ethyl acetate. The combined organic phases are dried over sodium sulphate. The solvent is removed on a rotary evaporator and the residue is purified chromatographically on silica gel 60 (mobile phase: gradient dichloromethane/ethanol 20:1→5:1).

Yield: 148 mg (21% of theory)

$^1$H-NMR (400 MHz, DMSO-d$_6$): δ=11.78 (s, 1H), 8.30 (s, 1H), 7.38-7.26 (m, 2H), 6.98 (t, 2H), 5.69 (s, 1H), 5.24-5.13 (m, 1H), 4.45-4.38 (m, 2H).

LC-MS (Method 2): $R_t$=1.37 min; MS (ESIpos): m/z=208 [M+H]$^+$.

Example 17A 3-(Chloromethyl)-N-(4-fluorophenyl)-1H-pyrazole-5-amine

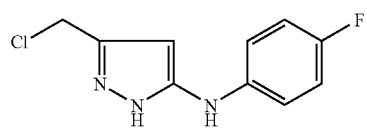 [SMILES: Fc1ccc(Nc2cc(CCl)n[nH]2)cc1]

138 mg (0.67 mmol) of the compound from example 16A are dissolved in 10 ml of dichloromethane, and 95 mg (0.80 mmol) of thionyl chloride are added. The reaction mixture is stirred at RT for 24 h. The solvent is removed on a rotary evaporator and the product that remains is directly reacted further.

Yield: 150 mg (93% of theory, 93% pure)

LC-MS (Method 3): $R_t$=1.79 min; MS (ESIpos): m/z=226 [M+H]$^+$.

Example 18A

N-[5-(Hydroxymethyl)pyridin-2-yl]acetamide

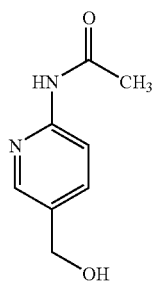

A solution of 219 mg (1.22 mmol) of 6-(acetylamino)nicotinic acid [preparable from 6-aminonicotinic acid according to A. Zafar et al., *Tetrahedron* 56, 8419-8428 (2000)] in 25.4 ml of dry THF is cooled to −10° C., and 123 mg (1.22 mmol) of 4-methylmorpholine and 132 mg (1.22 mmol) of ethyl chloroformate are added dropwise with stirring. The reaction solution is stirred at −10° C. for 30 min 2.44 ml (2.44 mmol) of a 1 M solution of lithium aluminium hydride and THF are then added dropwise. The reaction mixture is stirred for 8 h and slowly warmed to RT during this time. The reaction solution is then cooled to 0° C., 0.4 ml of water and 0.8 ml of 1 N aqueous sodium hydroxide solution are added carefully and, after warming to RT, the mixture is stirred at this temperature for 8 h. The mixture is filtered and the filtrate is concentrated on a rotary evaporator. The crude product that remains is used for the subsequent reaction without further purification.

LC-MS (Method 9): $R_t$=1.06 min; MS (ESIpos): m/z=167 [M+H]$^+$.

Example 19A

N-(5-Formylpyridin-2-yl)acetamide

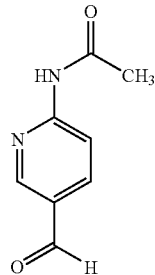

500 mg of powdered molecular sieve (4 Å) and 113 mg (0.96 mmol) of N-methylmorpholine N-oxide are added to a solution of the crude product from example 18A in 2 ml of dry dichloromethane. 11 mg (0.03 mmol) of tetrapropylammonium perruthenate are then added to the reaction mixture, which is then stirred at RT for 1 h. The mixture is purified directly by chromatography on a silica gel fritte (mobile phase: gradient dichloromethane/ethanol 100:1→10:1). All product-containing fractions are combined, the solvent is removed on a rotary evaporator and the residue is purified further by another silica gel chromatography (mobile phase: gradient dichloromethane/ethanol 200:1→5:1).

Yield: 31 mg (17% of theory, 58% pure)

LC-MS (Method 9): $R_t$=2.14 min; MS (ESIpos): m/z=165 [M+H]$^+$.

Example 20A

N-(2'-Amino-3',5'-dicyano-6'-mercapto-3,4'-bipyridin-6-yl)acetamide

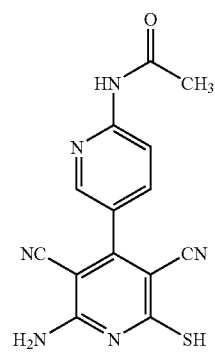

30 mg (0.18 mmol) of the compound from example 19A are dissolved in 0.4 ml of ethanol, 37 mg (0.37 mmol) of cyanothioacetamide and 37 mg (0.37 mmol) of 4-methylmorpholine are added and the mixture is stirred at +78° C. for 4 h. The mixture is then cooled to RT and stirred at this temperature for a further 8 h. A yellow precipitate is formed and filtered off with suction over a fritte. The filtrate is purified directly by preparative HPLC (column: YMC GEL ODS-AQ S-5/15 μm; mobile phase gradient: acetonitrile/water 10:90→95:5).

Yield: 14 mg (13% of theory, 52% pure)

LC-MS (Method 8): $R_t$=1.38 min; MS (ESIpos): m/z=311 [M+H]$^+$.

Example 21A 4-(Chloromethyl)-2-(4-chlorophenyl)-1,3-oxazole

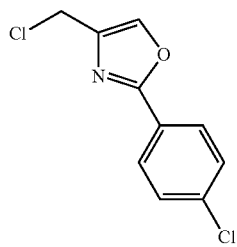 [SMILES: ClCc1coc(-c2ccc(Cl)cc2)n1]

With stirring, 816 mg (6.43 mmol) of 1,3-dichloroacetone and 1000 mg (6.43 mmol) of p-chlorobenzamide are heated at +135° C. for 1 h. After cooling to RT, 1.6 ml of conc. sulphuric acid are added, and the mixture is stirred at RT for a further 5 min. The entire mixture is then poured onto 50 ml of ice. A precipitate is formed which is filtered off with suction, dried under high vacuum and then purified chromatographically on silica gel 60 (mobile phase: gradient cyclohexane/ethyl acetate 20:1→5:1).

Yield: 532 mg (36% of theory)

$^1$H-NMR (400 MHz, DMSO-$d_6$): δ=8.30 (s, 1H), 7.99 (d, 2H), 7.62 (d, 2H), 4.75 (s, 2H).

LC-MS (Method 3): $R_t$=2.36 min; MS (ESIpos): m/z=228 [M]$^+$.

Example 22A 4-(Chloromethyl)-2-(3,4-difluorophenyl)-1,3-oxazole

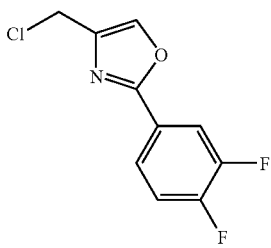 [SMILES: Fc1ccc(-c2nc(CCl)co2)cc1F]

With stirring, 500 mg (3.94 mmol) of 1,3-dichloroacetone and 619 mg (3.94 mmol) of 3,4-difluorobenzamide are heated at +135° C. for 1 h. After cooling to RT, the mixture is allowed to stand at this temperature for 90 min 1.0 ml of conc. sulphuric acid is then added, and the mixture is stirred at RT for a further 15 min. The entire mixture is then poured onto 50 ml of ice. Initially, a viscous oil is formed. The mixture is stirred for 60 min, during which time a precipitate is formed which is filtered off with suction, dried under high vacuum and then purified chromatographically on silica gel 60 (mobile phase: isohexane/ethyl acetate 10:1).

Yield: 429 mg (47% of theory)

$^1$H-NMR (400 MHz, DMSO-$d_6$): δ=8.31 (s, 1H), 8.02-7.93 (m, 1H), 7.88-7.81 (m, 1H), 7.68-7.59 (m, 1H), 4.75 (s, 2H).

LC-MS (Method 2): $R_t$=2.40 min; MS (ESIpos): m/z=230 [M+H]$^+$.

Example 23A

2-[(6-Methylpyridin-3-yl)oxy]ethanol

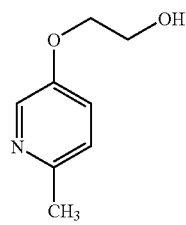

5.00 g (45.82 mmol) of 3-hydroxy-6-methylpyridine are dissolved in 65 ml of dry DMF, 6.87 g (54.98 mmol) of 2-bromoethanol and 25.33 g (183.27 mmol) of potassium carbonate are added and the mixture is stirred at +150° C. for 8 h. The mixture is then filtered, and the filtrate is concentrated on a rotary evaporator. After addition of 100 ml of ethyl acetate and 30 ml of saturated aqueous sodium bicarbonate solution, the phases are separated and the aqueous phase is extracted two more times with in each case 30 ml of ethyl acetate. The combined organic phases are dried over magnesium sulphate, and the solvent is removed on a rotary evaporator. Without further purification, the residue is used for the subsequent reaction.

Yield: 7.26 g (crude product)

LC-MS (Method 9): $R_t$=0.76 min; MS (ESIpos): m/z=154 [M+H]$^+$.

Example 24A

2-[(6-Methyl-1-oxidopyridin-3-yl)oxy]ethanol

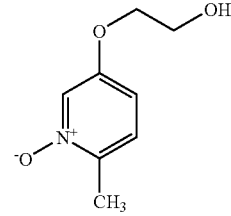

6.00 g of the crude product from example 23A are dissolved in 45.6 ml of dichloromethane, and 9.91 g (43.09 mmol) of meta-chloroperbenzoic acid are added a little at a time. The reaction mixture is stirred at RT for 8 h. The solvent is then removed on a rotary evaporator, and the residue is purified chromatographically on silica gel 60 (mobile phase: gradient cyclohexane/ethyl acetate 20:1→5:1). The product obtained in this manner is used without further purification for the subsequent reaction.

Yield: 2.73 g (34% of theory, 82% pure)

LC-MS (Method 9): $R_t$=1.68 min; MS (ESIpos): m/z=170 [M+H]$^+$.

Example 25A

[5-(2-Acetoxyethoxy)pyridin-2-yl]methyl acetate

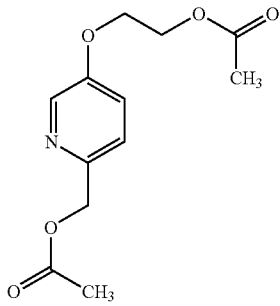 [SMILES: CC(=O)OCCOc1ccc(COC(C)=O)nc1]

20 ml (211.97 mmol) of acetic anhydride are added to 2.73 g of the crude product from example 24A, and the mixture is stirred without further solvent at +120° C. for 3 h. At 0° C., 20 ml of saturated aqueous sodium bicarbonate solution are then added, and the reaction mixture is extracted twice with in each case 40 ml of dichloromethane. The combined organic phases are dried over magnesium sulphate, and the solvent is removed on a rotary evaporator. Without further purification, the crude product is used for the subsequent reaction.

Yield: 4.08 g (68% of theory, 68% pure)

LC-MS (Method 10): $R_t$=1.75 min; MS (ESIpos): m/z=254 [M+H]$^+$.

Example 26A

[5-(2-Acetoxyethoxy)-1-oxidopyridin-2-yl]methyl acetate

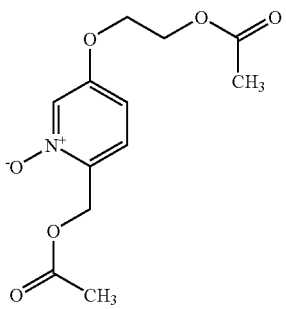

0.74 g of the crude product from example 25A is dissolved in 3.4 ml of dry dichloromethane, and 0.74 g (3.21 mmol) of meta-chloroperbenzoic acid is added a little at a time. The reaction mixture is stirred at RT for 8 h, and 2 ml of saturated aqueous sodium bicarbonate solution are then added. With stirring, more sodium bicarbonate powder (about 0.4 g) is added until the evolution of gas has ceased. The aqueous phase is extracted twice with in each case 5 ml of dichloromethane, and the combined organic phases are dried over magnesium sulphate. After removal of the solvent on a rotary evaporator, the crude product that remains is used directly for the subsequent reaction.

Yield: 0.83 g (84% of theory, 79% pure)

LC-MS (Method 9): $R_t$=2.39 min; MS (ESIpos): m/z=270 [M+H]$^+$.

Example 27A

[5-(2-Acetoxyethoxy)pyridin-2-yl]methylene diacetate

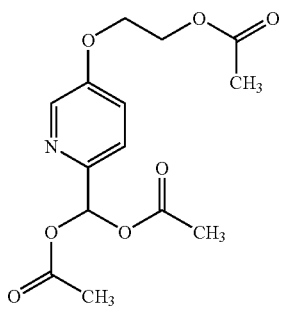 [SMILES: CC(=O)OCCOc1ccc(C(OC(C)=O)OC(C)=O)nc1]

5 ml (53.00 mmol) of acetic anhydride are added to 0.83 g of the crude product from example 26A, and without further solvent the mixture is stirred at +120° C. for 3 h. The reaction mixture is then cooled to 0° C., and 2 ml of saturated aqueous sodium bicarbonate solution are added. The aqueous phase is extracted twice with in each case 5 ml of dichloromethane, and the combined organic phases are dried over magnesium sulphate. After removal of the solvent, the crude product is used without further purification for the subsequent reaction.

Yield: 0.80 g (44% of theory, 44% pure)

LC-MS (Method 11): $R_t$=1.62 min; MS (ESIpos): m/z=312 [M+H]$^+$.

Example 28A 5-(2-Hydroxyethoxy)pyridine-2-carbaldehyde

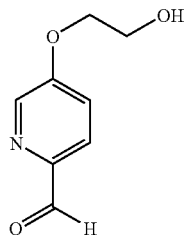 [SMILES: O=Cc1ccc(OCCO)cn1]

100 mg of the crude product from example 27A are dissolved in 2 ml of dioxane, and 0.48 ml (1.93 mmol) of a 4 M solution of hydrogen chloride gas in dioxane is added. The mixture is stirred at +100° C. for 1 h. The reaction mixture is then concentrated on a rotary evaporator, and the residue is taken up in 2 ml of water. The mixture is neutralized using 0.7 ml of 1 N aqueous sodium hydroxide solution and extracted three times in total with in each case 4 ml of diethyl ether. The combined organic phases are dried over magnesium sulphate. After removal of the solvent, the crude product is used without further purification for the subsequent reaction.

Yield: 42 mg (64% of theory, 82% pure)

LC-MS (Method 9): $R_t$=1.96 min; MS (ESIpos): m/z=168 [M+H]$^+$.

Example 29A

2'-Amino-5-(2-hydroxyethoxy)-6'-mercapto-2,4'-bipyridine-3',5'-dicarbonitrile

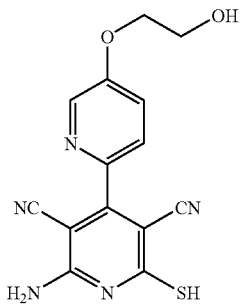

40 mg of the crude product from example 28A and 48 mg (0.48 mmol) of cyanothioacetamide are dissolved in 0.5 ml of dry ethanol, and 48 mg (0.48 mmol) of 4-methylmorpholine are added. The reaction mixture is stirred for a total of 4 h, initially at 0° C. and then with slow warming to RT. The solvent is removed on a rotary evaporator and the residue is applied to diatomaceous earth and purified chromatographically on silica gel 60 (mobile phase: gradient cyclohexane/ethyl acetate 20:1→5:1). Without further purification, the product obtained in this manner is used for the subsequent reaction.

Yield: 23 mg (15% of theory, 50% pure)

LC-MS (Method 8): $R_t$=1.22 min; MS (ESIpos): m/z=314 [M+H]$^+$.

Example 30A

6-{[(4R)-2,2-Dimethyl-1,3-dioxolan-4-yl]methoxy}nicotinaldehyde

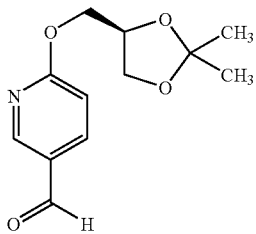 [SMILES: CC1(C)OC[C@@H](COc2ccc(C=O)cn2)O1]

7.47 g (56.51 mmol) of R-(−)-2,3-dimethyl-1,3-dioxolane-4-methanol are initially charged in 80 ml of dry DMF, and 4.76 g (42.39 mmol) of potassium tert-butoxide are added. The mixture is stirred at RT for 15 min 4.00 g (28.26 mmol) of 6-chloronicotinaldehyde are then added. The reaction mixture is stirred at RT for 12 h. The mixture is then poured into a mixture of 100 ml of ethyl acetate and 100 ml of aq. sodium bicarbonate solution. The phases are separated, and the organic phase is washed twice with in each case 30 ml of water. The organic phase is dried over magnesium sulphate, and the solvent is removed on a rotary evaporator. The residue is purified by column chromatography on silica gel 60 (mobile phase gradient: cyclohexane/ethyl acetate 50:1→2:1). Without further purification, the product obtained in this manner is used for the subsequent step.

Yield: 1.91 g (23% of theory, 82% pure)

LC-MS (Method 14): $R_t$=1.33 min; MS (ESIpos): m/z=238 [M+H]$^+$.

Example 31A

2'-Amino-6-{[(4R)-2,2-dimethyl-1,3-dioxolan-4-yl]methoxy}-6'-mercapto-3,4'-bipyridine-3',5'-dicarbonitrile

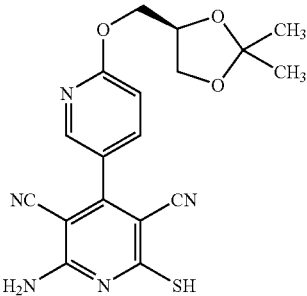

1.91 g (8.06 mmol) of the compound from example 30A and 1.61 g (16.12 mmol) of cyanothioacetamide are initially charged in 18 ml of ethanol, and 1.63 g (16.12 mmol) of 4-methylmorpholine are added. The reaction mixture is stirred at 78° C. for 4 h and then at RT for a further 8 h. After removal of the solvent on a rotary evaporator, the residue is purified by column chromatography on silica gel 60 (mobile phase gradient: dichloromethane/ethanol 50:1→5:1). Without further purification, the product obtained in this manner is used for the subsequent step.

Yield: 1.54 g (31% of theory, 63% pure)

LC-MS (Method 14): $R_t$=1.43 min; MS (ESIpos): m/z=384 [M+H]$^+$.

Example 32A

2'-Amino-6'-({[2-(4-chlorophenyl)-1,3-oxazol-4-yl]methyl}thio)-6-{[(4R)-2,2-dimethyl-1,3-dioxolan-4-yl]methoxy}-3,4'-bipyridine-3',5'-dicarbonitrile

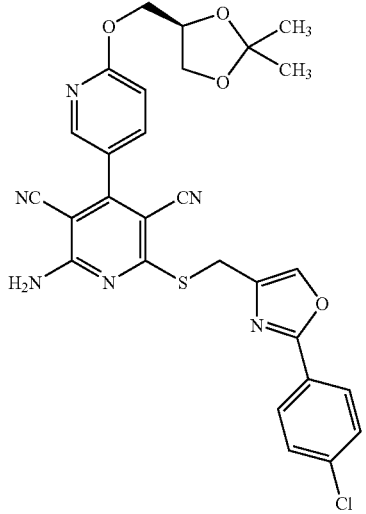

200 mg (0.32 mmol) of the crude product from example 31A, 90 mg (0.36 mmol) of 4-(chloromethyl)-2-(4-chlorophenyl)-1,3-oxazole and 82 mg (0.97 mmol) of sodium bicarbonate are added to 3.4 ml of dry DMF, and the mixture is stirred at RT for 20 h. The mixture is then purified directly by preparative HPLC (column: YMC GEL ODS-AQ S-5/15 μm; mobile phase gradient: acetonitrile/water 10:90→95:5).

Yield: 95 mg (51% of theory)

LC-MS (Method 14): $R_t$=2.41 min; MS (ESIpos): m/z=575 [M+H]$^+$.

Example 33A

2'-Amino-6'-({[2-(4-chlorophenyl)-1,3-oxazol-4-yl]methyl}thio)-6-{[(4S)-2,2-dimethyl-1,3-dioxolan-4-yl]methoxy}-3,4'-bipyridine-3',5'-dicarbonitrile

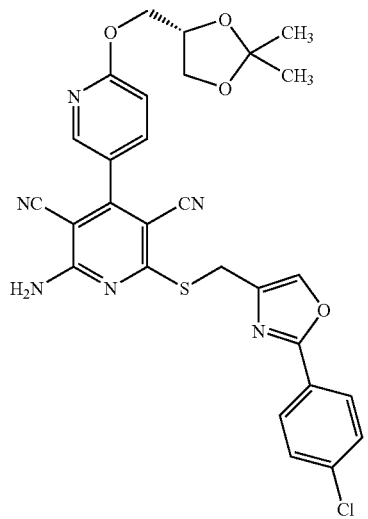

The title compound is prepared analogously to example 32A from S-(−)-2,3-dimethyl-1,3-dioxolane-4-methanol.

Yield: 82 mg (57% of theory)

LC-MS (Method 8): $R_t$=3.03 min; MS (ESIpos): m/z=575 [M+H]$^+$.

Example 34A 2-(4-Chlorophenyl)-4,5-dimethyl-1,3-oxazole 3-oxide

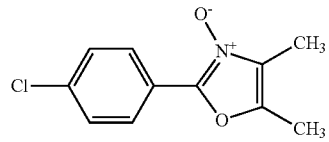

1.00 g (9.89 mmol) of diacetyl monoxime and 1.53 g (10.88 mmol) of 4-chlorobenzaldehyde are initially charged in 2 ml (34.94 mmol) of glacial acetic acid. With ice-cooling, hydrogen chloride gas is then introduced into the reaction mixture for 30 min 10 ml of diethyl ether are then added to the reaction mixture. A precipitate is formed, which is filtered off with suction and washed twice with in each case 2 ml of diethyl ether. The precipitate is suspended in about 5 ml of water, and the suspension is made basic using aqueous ammonia. The suspension is then extracted four times with in each case 10 ml of dichloromethane. The combined organic phases are dried over magnesium sulphate, and the solvent is removed on a rotary evaporator. Without further purification, the product obtained in this manner is used for the subsequent step.

Yield: 1.85 g (84% of theory)

LC-MS (Method 12): $R_t$=2.29 min; MS (ESIpos): m/z=224 [M+H]$^+$.

Example 35A 4-(Chloromethyl)-2-(4-chlorophenyl)-5-methyl-1,3-oxazole

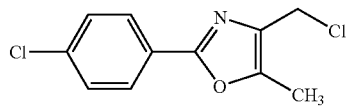

1.00 g (4.47 mmol) of the compound from example 34A is initially charged in 15 ml of chloroform, and 1.5 ml (16.10 mmol) of phosphoryl chloride are added carefully. With stirring, the reaction mixture is heated at reflux for 30 min. The mixture is then cooled to 0° C. and made weakly basic by addition of aqueous ammonia. The mixture is extracted three times with in each case 20 ml of ethyl acetate. The combined organic phases are washed twice with in each case 5 ml of water and then dried over magnesium sulphate. The solvent is removed on a rotary evaporator. Without further purification, the product obtained in this manner is used for the subsequent reactions.

Yield: 1.33 g (96% of theory, 78% pure)

$^1$H-NMR (400 MHz, DMSO-d$_6$): δ=7.95 (d, 2H), 7.60 (d, 2H), 4.77 (s, 2H), 2.44 (s, 3H).

LC-MS (Method 8): $R_t$=2.80 min; MS (ESIpos): m/z=242 [M+H]$^+$.

Example 36A 2-(4-Chlorophenyl)-5-ethyl-4-methyl-1,3-oxazole 3-oxide

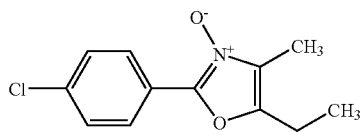 [SMILES: CCc1oc(-c2ccc(Cl)cc2)[n+]([O-])c1C]

1.00 g (8.69 mmol) of 2,3-pentanedione 2-oxime and 1.34 g (9.55 mmol) of 4-chlorobenzaldehyde are initially charged in 2 ml (34.94 mmol) of glacial acetic acid. With ice-cooling, hydrogen chloride gas is then introduced into the reaction mixture for 30 min. 10 ml of diethyl ether are then added to the reaction mixture. A precipitate is formed, which is filtered off with suction and washed twice with in each case 2 ml of diethyl ether. The precipitate is suspended in about 5 ml of water, and the suspension is made basic using aqueous ammonia. The suspension is then extracted four times with in each case 10 ml of dichloromethane. The combined organic phases are dried over magnesium sulphate, and the solvent is removed on a rotary evaporator. Without further purification, the product obtained in this manner is used for the subsequent step.

Yield: 1.6 g (76% of theory)

$^1$H-NMR (400 MHz, DMSO-$d_6$): δ=8.42 (d, 2H), 7.63 (d, 2H), 2.76 (q, 2H), 2.10 (s, 3H), 1.24 (t, 3H).

LC-MS (Method 15): $R_t$=1.67 min; MS (ESIpos): m/z=238 [M+H]$^+$.

Example 37A 4-(Chloromethyl)-2-(4-chlorophenyl)-5-ethyl-1,3-oxazole

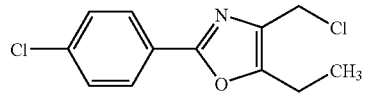

1.00 g (4.21 mmol) of the compound from example 36A is dissolved in 15 ml of chloroform, and 1.4 ml (15.15 mmol) of phosphoryl chloride is added carefully. The mixture is heated at reflux and stirred at this temperature for 30 min. The mixture is then cooled to 0° C. and made weakly basic using aqueous ammonia. The reaction mixture is extracted three times with in each case 20 ml of ethyl acetate. The combined organic phases are washed once with 10 ml of water and then dried over magnesium sulphate. The solvent is removed on a rotary evaporator, and the residue is dried under reduced pressure in a drying cabinet. Without further purification, the product obtained in this manner is used for the subsequent reactions.

Yield: 1.2 g (84% of theory, 74% pure)

$^1$H-NMR (400 MHz, DMSO-$d_6$): δ=7.96 (d, 2H), 7.60 (d, 2H), 4.77 (s, 2H), 2.85 (q, 2H), 1.23 (t, 3H).

LC-MS (Method 15): $R_t$=2.56 min; MS (ESIpos): m/z=256 [M+H]$^+$.

Example 38A

2'-Chloro-6'-({[2-(4-chlorophenyl)-1,3-thiazol-4-yl]methyl}thio)-6-(2-hydroxyethoxy)-3,4'-bipyridine-3',5'-dicarbonitrile

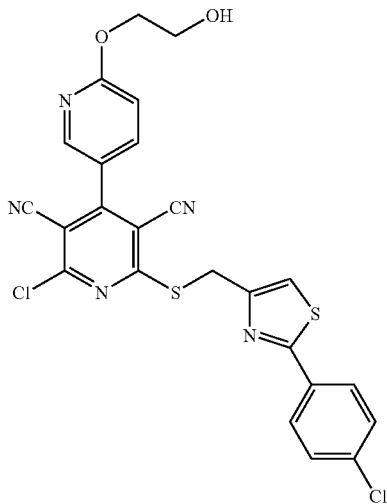

225 mg (1.92 mmol) of isopentyl nitrite and 258 mg (1.92 mmol) of copper(II) chloride are initially charged in 18 ml of acetonitrile, and 500 mg (0.96 mmol) of the compound from example 19 are added. The reaction mixture is stirred at 60° C. for 2 h. After cooling, 19 ml of 1 N hydrochloric acid are added. The aqueous phase is extracted twice with in each case 30 ml of ethyl acetate. The combined organic phases are dried over magnesium sulphate, and the solvent is removed on a rotary evaporator. The residue is purified by column chromatography on silica gel 60 (mobile phase:cyclohexane/ethyl acetate 10:1). Without further purification, the product obtained in this manner is used for the subsequent reactions.

Yield: 535 mg (84% of theory, 81% pure)

LC-MS (Method 13): $R_t$=1.48 min; MS (ESIpos): m/z=541 [M+H]$^+$.

Working Examples

Example 1

2'-Amino-6'-[({2-[(3-chloro-4-fluorophenyl)amino]-1,3-thiazol-4-yl}methyl)thio]-6-(2-hydroxyethoxy)-3,4'-bipyridine-3',5'-dicarbonitrile

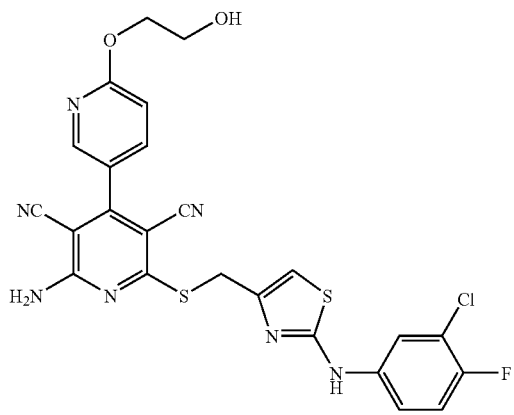

209 mg (0.67 mmol) of 4-fluoro-3-chlorophenylthiourea and 89 mg (0.70 mmol) of 1,3-dichloroacetone are dissolved in 5 ml of DMF, and the reaction solution is stirred at 80° C. for 3 h. After cooling, 209 mg (0.67 mmol) of the compound from example 2A and 224 mg (2.67 mmol) of sodium bicarbonate are added, and the mixture is stirred at RT for a further 20 h. The mixture is then filtered through a paper filter, and sat. sodium bicarbonate solution (5 ml) is added to the filtrate. The aqueous phase is extracted with ethyl acetate (three times, 5 ml each). The combined organic phases are dried over sodium sulphate, and the solvent is removed on a rotary evaporator.

Yield: 107 mg (29% of theory)

$^1$H-NMR (400 MHz, DMSO-$d_6$): δ=10.43 (s, 1H), 8.40-7.90 (br. s, 2H), 8.34 (s, 1H), 7.88-7.97 (m, 2H), 7.51-7.43 (m, 1H), 7.33 (t, 1H), 7.06-6.98 (m, 2H), 4.88 (t, 1H), 4.49 (s, 2H), 4.39-4.30 (m, 2H), 3.78-3.68 (m, 2H).

LC-MS (Method 2): $R_t$=2.42 min; MS (ESIpos): m/z=554 [M+H]$^+$.

Example 2

2'-Amino-6'-[({2-[(4-fluorophenyl)amino]-1,3-thia-zol-4-yl}methyl)thio]-6-[(2-hydroxyethyl)amino]-3,4'-bipyridine-3',5'-dicarbonitrile

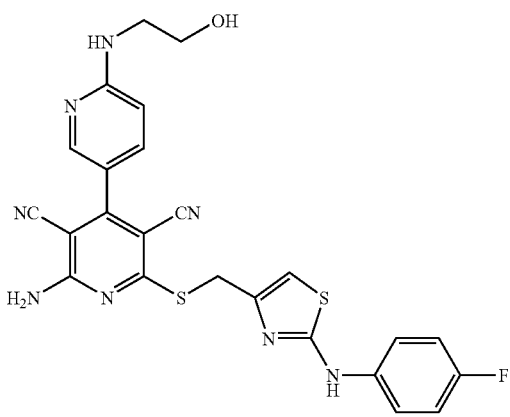

18 mg (0.10 mmol) of 4-fluorophenylthiourea and 13 mg (0.10 mmol) of 1,3-dichloroacetone are dissolved in 2 ml of DMF, and the reaction solution is stirred at 80° C. for 3 h. After cooling, 89 mg (0.09 mmol, 33% pure) of the compound from example 4A and 32 mg (0.38 mmol) of sodium bicarbonate are added, and the mixture is stirred at RT for a further 20 h. The mixture is then filtered through a paper filter, and the filtrate is purified directly by preparative HPLC (column: YMC GEL ODS-AQ S-5/15 µm; mobile phase gradient: acetonitrile/water 10:90→95:5). Sat. sodium bicarbonate solution (5 ml) is added to the product fraction obtained, and the mixture is extracted with ethyl acetate (three times, 5 ml each). The combined organic phases are dried over magnesium sulphate, and the solvent is removed on a rotary evaporator.

Yield: 18 mg (35% of theory)

$^1$H-NMR (300 MHz, DMSO-$d_6$): δ=10.24 (s, 1H), 8.13 (d, 1H), 7.67-7.59 (m, 2H), 7.56 (dd, 1H), 7.27-7.19 (m, 1H), 7.19-7.09 (m, 2H), 6.96 (s, 1H), 6.61 (d, 1H), 4.77 (t, 1H), 4.44 (s, 2H), 3.59-3.51 (m, 2H), 3.49-3.35 (m, 2H).

LC-MS (Method 3): $R_t$=1.83 min; MS (ESIpos): m/z=519 [M+H]$^+$.

The examples listed in Table 1 below are prepared from the appropriate starting materials analogously to example 1:

TABLE 1

| Example No. | Structure (Yield) | LC-MS: $R_t$ [min] (Method); MS (ESI): m/z [M + H]$^+$ | $^1$H-NMR (DMSO-$d_6$): |
|---|---|---|---|
| 3 | (60% of theory) | 2.10 min (2); m/z = 520 | δ (300 MHz) = 10.25 (s, 1H), 8.19 (br. s, 2H), 8.35 (d, 1H), 7.92 (dd, 1H), 7.68-7.58 (m, 2H), 7.19-7.08 (m, 2H), 7.11-7.07 (m, 2H), 4.89 (t, 1H), 4.45 (s, 2H), 4.38-4.30 (m, 2H), 3.78-3.68 (m, 2H). |
| 4 | (48% of theory) | 1.52 min (4); m/z = 426 | δ (300 MHz) = 8.38 (d, 1H), 8.30 (br. s, 2H), 7.92 (dd, 1H), 7.02 (d, 1H), 6.92 (s, 1H), 4.36 (s, 2H), 4.36-4.30 (m, 2H), 3.78-3.51 (m, 2H). |

TABLE 1-continued
| Example No. | Structure (Yield) | LC-MS: R_t [min] (Method); MS (ESI): m/z [M + H]+ | 1H-NMR (DMSO-d_6): |
|---|---|---|---|
| 5 | 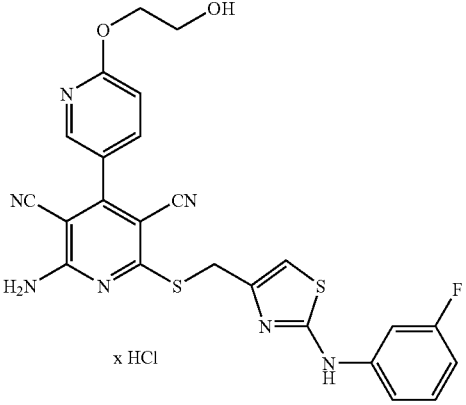 (9% of theory) | 2.16 min (2); m/z = 520 | |
| 6 | 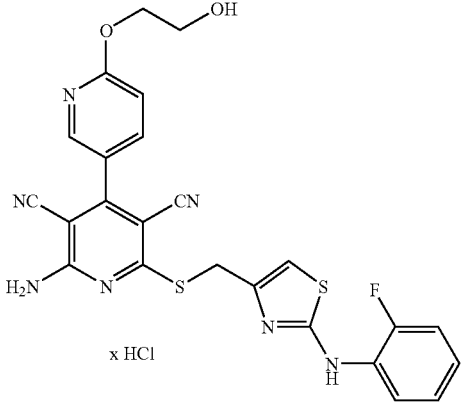 (43% of theory) | 2.14 min (2); m/z = 520 | δ (400 MHz) = 10.00 (s, 1H), 8.40-8.31 (m, 2H), 8.15 (br. s, 2H), 7.91 (d, 1H), 7.28-7.19 (m, 1H), 7.14 (t, 1H), 7.04-6.95 (m, 2H), 4.47 (s, 2H), 4.40-4.30 (m, 2H), 3.79-3.71 (m, 2H). |
| 7 | 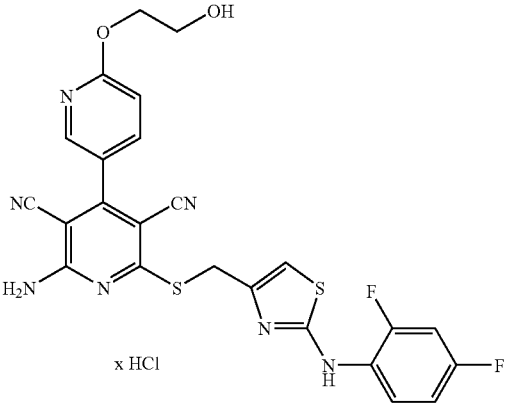 (39% of theory) | 2.38 min (4); m/z = 538 | δ (400 MHz) = 9.97 (s, 1H), 8.40-8.29 (m, 2H), 8.15 (br. s, 2H), 7.97-7.87 (m, 1H), 7.35-7.25 (m, 1H), 7.10-6.98 (m, 3H), 4.45 (s, 2H), 4.39-4.31 (m, 2H), 3.79-3.69 (m, 2H). |

TABLE 1-continued
| Example No. | Structure (Yield) | LC-MS: $R_t$ [min] (Method); MS (ESI): m/z [M + H]⁺ | ¹H-NMR (DMSO-d₆): |
|---|---|---|---|
| 8 | 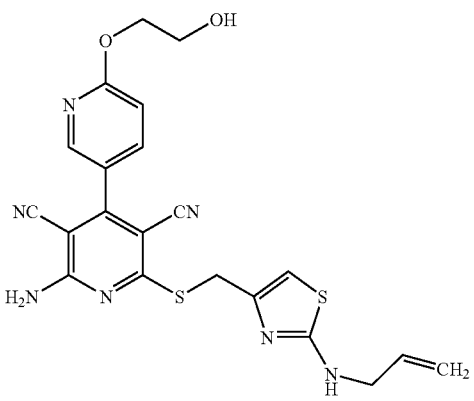 (3% of theory) | 1.81 min (2); m/z = 466 | δ (400 MHz) = 8.34 (s, 1H), 8.12 (br. s, 2H), 7.92 (d, 1H), 7.83-7.74 (m, 1H), 7.01 (d, 1H), 6.72 (s, 1H), 5.44-5.32 (m, 1H), 5.23 (d, 1H), 5.12 (d, 1H), 4.40-4.29 (m, 3H), 3.83 (s, 2H), 3.78-3.70 (m, 2H). |
| 9 | 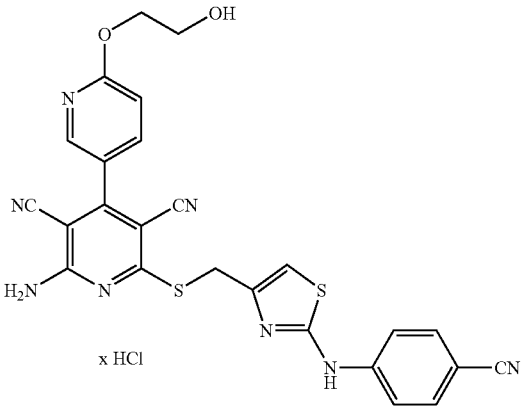 x HCl (7% of theory) | 3.54 min (9); m/z = 527 | |
| 10 | 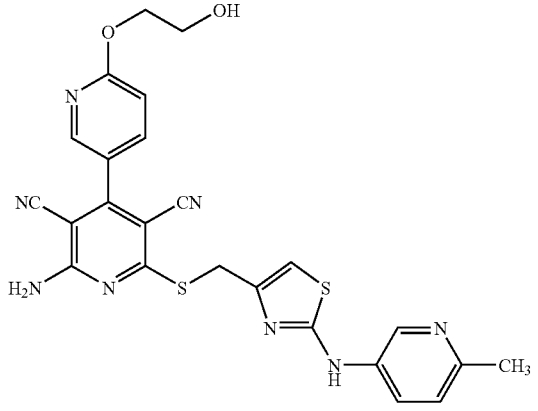 (33% of theory) | 1.33 min (3); m/z = 517 | δ (400 MHz) = 10.40 (s, 1H), 8.71 (s, 1H), 8.36 (s, 1H), 8.13 (br. s, 2H), 8.03 (d, 1H), 7.91 (d, 1H), 7.27 (d, 1H), 7.04 (s, 1H), 7.01 (d, 1H), 4.47 (s, 2H), 4.35 (t, 2H), 3.77-3.71 (m, 2H), 2.42 (s, 3H). |

TABLE 1-continued
| Example No. | Structure (Yield) | LC-MS: R$_t$ [min] (Method); MS (ESI): m/z [M + H]$^+$ | $^1$H-NMR (DMSO-d$_6$): |
|---|---|---|---|
| 11 | 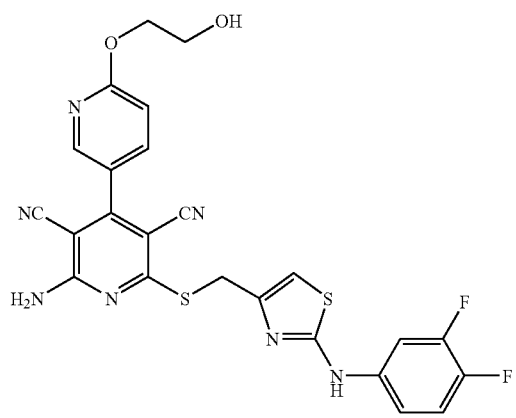 (29% of theory) | 2.18 min (3); m/z = 538 | δ (400 MHz) = 10.42 (s, 1H), 8.33 (d, 1H), 8.12 (br. s, 2H), 7.93-7.81 (m, 3H), 7.36 (q, 1H), 7.28-7.21 (m, 1H), 7.06-6.98 (m, 2H), 4.87 (t, 1H), 4.49 (s, 2H), 4.37 (t, 2H), 3.78-3.70 (m, 2H). |
| 12 | 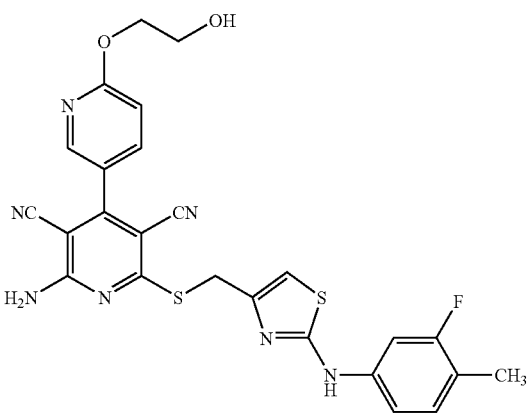 (25% of theory) | 2.24 min (3); m/z = 534 | δ (400 MHz) = 10.31 (s, 1H), 8.33 (d, 1H), 8.13 (br. s, 2H), 7.92 (dd, 1H), 7.59 (d, 1H), 7.21-7.11 (m, 2H), 7.04-6.97 (m, 2H), 4.49 (s, 2H), 4.35 (t, 1H), 3.73 (t, 2H), 2.17 (s, 3H). |
| 13 | 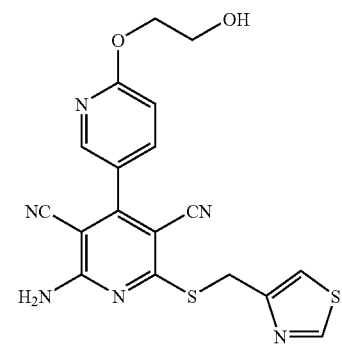 (29% of theory) | 1.77 min (2); m/z = 411 | δ (400 MHz) = 9.08 (s, 1H), 8.37 (d, 1H), 8.16 (br. s, 2H), 7.92 (dd, 1H), 7.88 (s, 1H), 7.00 (d, 1H), 4.88 (t, 1H), 4.63 (s, 2H), 4.36 (t, 1H), 3.74-3.70 (m, 2H). |

TABLE 1-continued
| Example No. | Structure (Yield) | LC-MS: R_t [min] (Method); MS (ESI): m/z [M + H]+ | 1H-NMR (DMSO-d_6): |
|---|---|---|---|
| 14 | 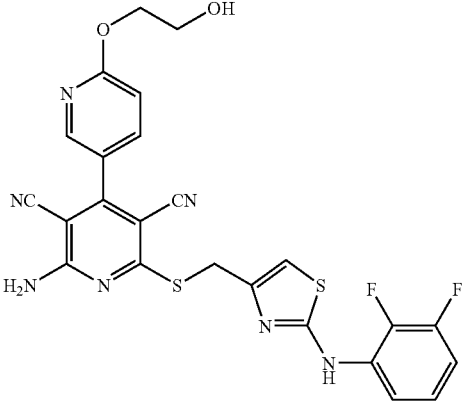 (29% of theory) | 2.44 min (4); m/z = 538 | δ (400 MHz) = 10.23 (s, 1H), 8.36 (s, 1H), 8.22 (t, 1H), 8.17 (br. s, 2H), 7.91 (dd, 1H), 7.19-6.94 (m, 4H), 4.88 (t, 1H), 4.49 (s, 2H), 4.36 (t, 1H), 3.78-3.69 (m, 2H). |
| 15 | 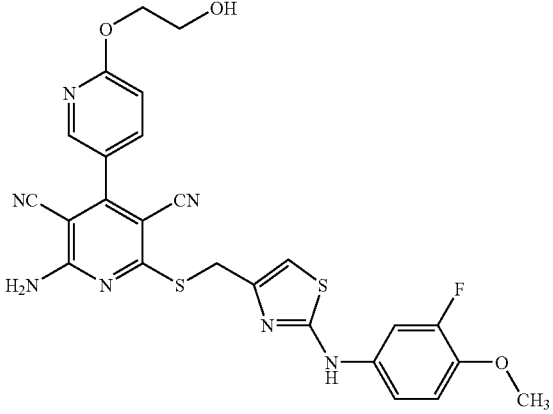 (24% of theory) | 2.23 min (2); m/z = 550 | |
| 16 | 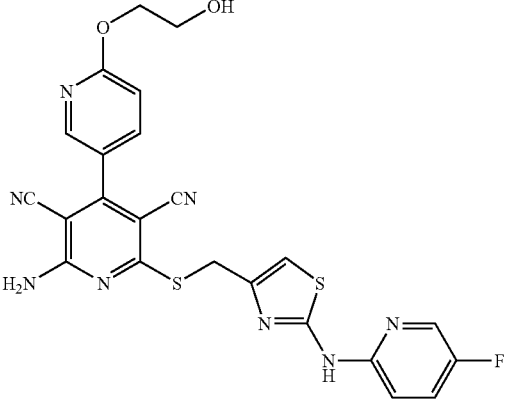 (34% of theory) | 2.20 min (2); m/z = 521 | δ (400 MHz) = 11.44 (s, 1H), 8.37 (d, 1H), 8.28 (d, 1H), 8.17 (br. s, 2H), 7.91 (dd, 1H), 7.73-7.64 (m, 1H), 7.11-7.04 (m, 2H), 7.01 (d, 1H), 4.50 (s, 2H), 4.34 (t, 1H), 3.73 (t, 2H). |

TABLE 1-continued
| Example No. | Structure (Yield) | LC-MS: R$_t$ [min] (Method); MS (ESI): m/z [M + H]$^+$ | $^1$H-NMR (DMSO-d$_6$): |
|---|---|---|---|
| 17 | 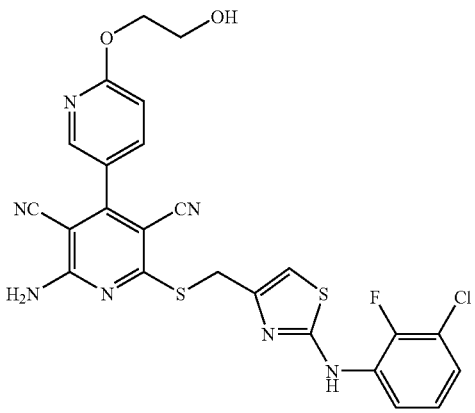<br>(28% of theory) | 2.45 min (2);<br>m/z = 554 | δ (400 MHz) = 10.21 (s, 1H), 8.46-8.37 (m, 1H), 8.34 (d, 1H), 8.18 (br. s, 2H), 7.91 (dd, 1H), 7.19-7.10 (m, 2H), 7.07 (s, 1H), 7.00 (d, 1H), 4.87 (t, 1H), 4.48 (s, 2H), 4.34 (t, 1H), 3.77-3.69 (m, 2H). |
| 18 | 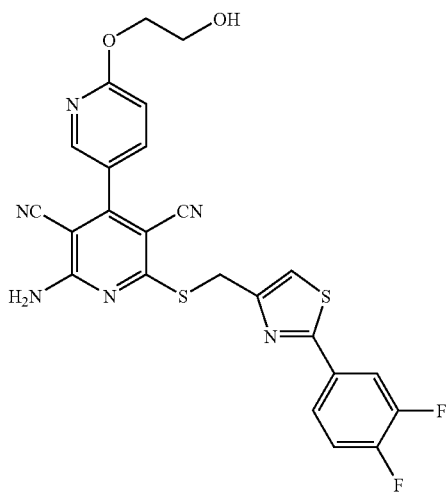<br>(53% of theory) | 2.67 min (8);<br>m/z = 523 | δ (400 MHz) = 8.40-8.04 (br. s, 2H), 8.34 (d, 1H), 8.05-7.88 (m, 3H), 7.83-7.76 (m, 1H), 7.58 (q, 1H), 7.00 (d, 1H), 4.88 (t, 1H), 4.63 (s, 2H), 4.39-4.31 (m, 2H), 3.77-3.69 (m, 2H). |

Example 19

2'-Amino-6'-({[2-(4-chlorophenyl)-1,3-thiazol-4-yl]methyl}thio)-6-(2-hydroxyethoxy)-3,4'-bipyridine-3',5'-dicarbonitrile

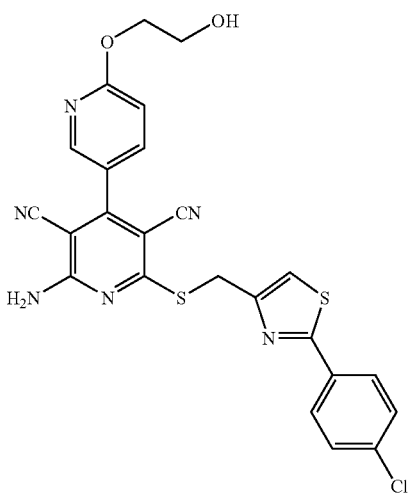

63 mg (0.26 mmol) of 4-chloromethyl-2-(4-chlorphenyl)thiazole, 100 mg (0.23 mmol) of the compound from example 2A and 78 mg (0.93 mmol) of sodium bicarbonate are dissolved in 1.5 ml of DMF, and the reaction solution is stirred at RT for 20 h. The mixture is then filtered through a paper filter, and the filtrate is directly purified chromatographically by preparative HPLC (column: YMC GEL ODS-AQ S-5/15 µm; mobile phase gradient: acetonitrile/water 10:90→95:5). This gives the title compound as a beige solid.

Yield: 67 mg (55% of theory)

$^1$H-NMR (400 MHz, DMSO-$d_6$): δ=8.40-8.01 (br. s, 2H), 8.35 (d, 1H), 7.98-7.88 (m, 3H), 7.58 (d, 2H), 7.00 (d, 1H), 4.88 (t, 1H), 4.63 (s, 2H), 4.37-4.31 (m, 2H), 3.77-3.70 (m, 2H).

LC-MS (Method 8): $R_t$=2.76 min; MS (ESIpos): m/z=521 [M+H]$^+$.

The examples listed in Table 2 below are prepared from the appropriate starting materials analogously to example 19:

TABLE 2

| Example No. | Structure (yield) | LC-MS: $R_t$ [min] (Method); MS (ESI): m/z [M + H]$^+$ | $^1$H-NMR (DMSO-$d_6$): |
|---|---|---|---|
| 20 | 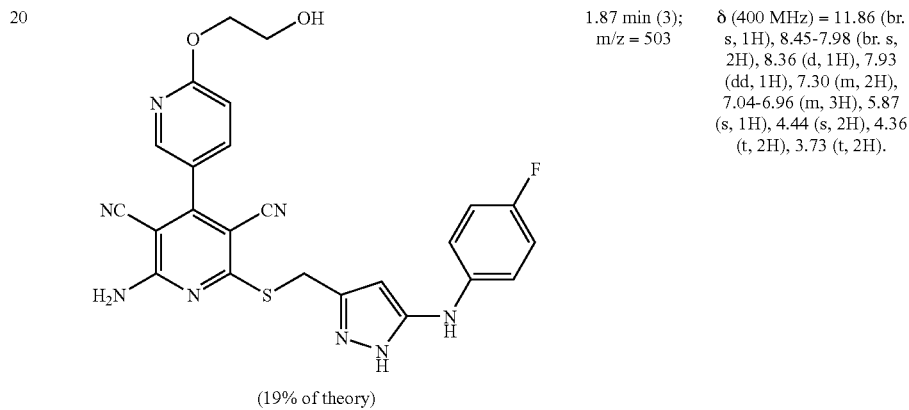 (19% of theory) | 1.87 min (3); m/z = 503 | δ (400 MHz) = 11.86 (br. s, 1H), 8.45-7.98 (br. s, 2H), 8.36 (d, 1H), 7.93 (dd, 1H), 7.30 (m, 2H), 7.04-6.96 (m, 3H), 5.87 (s, 1H), 4.44 (s, 2H), 4.36 (t, 2H), 3.73 (t, 2H). |

TABLE 2-continued
| Example No. | Structure (yield) | LC-MS: R$_t$ [min] (Method); MS (ESI): m/z [M + H]$^+$ | $^1$H-NMR (DMSO-d$_6$): |
|---|---|---|---|
| 21 | 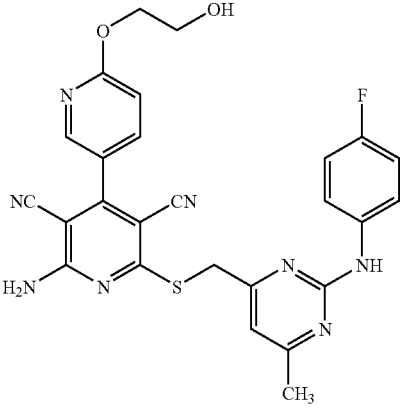 (36% of theory) | 2.13 min (3); m/z = 529 | δ (400 MHz) = 9.62 (s, 1H), 8.49-7.97 (br. s, 2H), 8.34 (d, 1H), 7.92 (dd, 1H), 7.84-7.76 (m, 2H), 7.08 (t, 2H), 7.02 (d, 1H), 6.97 (s, 1H), 4.87 (t, 1H), 4.48 (s, 2H), 4.39-4.31 (m, 2H), 3.78-3.69 (m, 2H), 2.37 (s, 3H). |
| 22 | 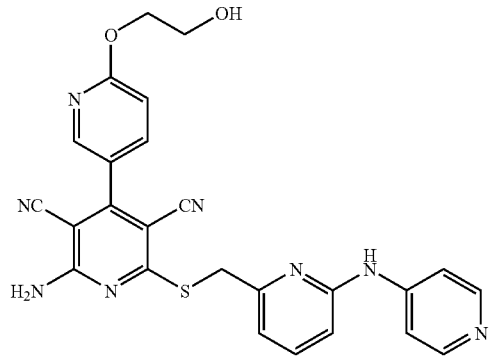 (46% of theory) | 1.39 min (2); m/z = 497 | δ (400 MHz) = 8.84 (d, 2H), 8.72 (s, 2H), 8.50-8.02 (br. s, 2H), 8.34 (d, 1H), 8.12 (t, 1H), 7.95-7.89 (m, 2H), 7.83 (d, 1H), 7.06-6.97 (m, 3H), 4.99-4.72 (br. s, 1H), 4.66 (s, 2H), 4.45 (t, 2H), 3.73 (t, 2H). |
| 23 | 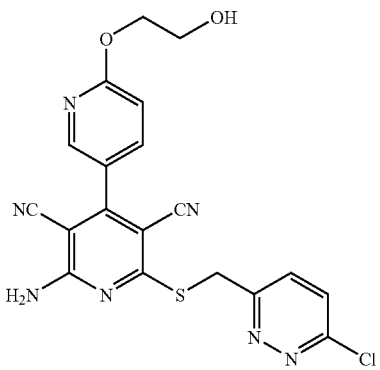 (39% of theory) | 1.85 min (4); m/z = 440 | δ (400 MHz) = 8.43-7.99 (br. s, 2H), 8.34 (d, 1H), 8.11-8.04 (m, 1H), 7.97-7.86 (m, 2H), 7.01 (d, 1H), 4.92-4.83 (m, 1H), 4.77 (s, 2H), 4.40-4.29 (m, 2H), 3.79-3.69 (m, 2H). |

TABLE 2-continued
| Example No. | Structure (yield) | LC-MS: R$_t$ [min] (Method); MS (ESI): m/z [M + H]$^+$ | $^1$H-NMR (DMSO-d$_6$): |
|---|---|---|---|
| 24 | 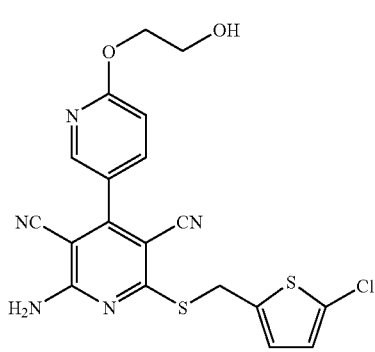 (32% of theory) | 2.43 min (8); m/z = 443.9 [M]$^+$ | δ (400 MHz) = 8.43-8.00 (br. s, 2H), 8.36 (d, 1H), 7.94 (d, 1H), 7.09 (d, 1H), 7.01 (d, 1H), 6.95 (d, 1H), 4.87 (t, 2H), 4.69 (s, 2H), 4.36 (t, 2H), 3.78-3.70 (m, 2H). |
| 25 | 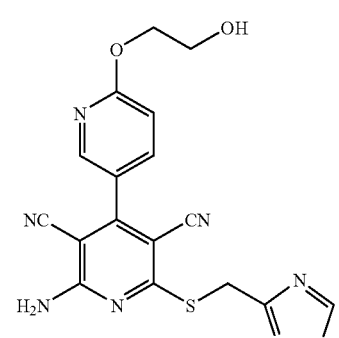 (31% of theory) | 1.82 min (8); m/z = 396 | δ (400 MHz) = 9.61 (s, 1H), 8.38 (d, 1H), 8.27-7.99 (br. s, 2H), 7.94 (dd, 1H), 7.02 (d, 1H), 4.91-4.83 (m, 2H), 4.77 (s, 2H), 4.40-4.31 (m, 2H), 3.78-3.70 (m, 2H). |
| 26 | 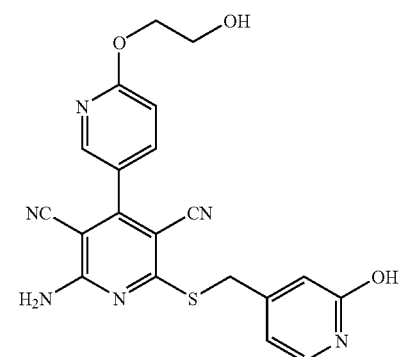 (27% of theory) | 1.35 min (3); m/z = 421 | δ (400 MHz) = 11.45 (s, 1H), 8.61-7.99 (br. s, 2H), 8.36 (d, 1H), 7.92 (dd, 1H), 7.31 (d, 1H), 7.00 (d, 1H), 6.52 (s, 1H), 6.23 (d, 1H), 4.87 (t, 2H), 4.36 (t, 2H), 4.32 (s, 2H), 3.77-3.69 (m, 2H). |

TABLE 2-continued
| Example No. | Structure (yield) | LC-MS: R$_t$ [min] (Method); MS (ESI): m/z [M + H]$^+$ | $^1$H-NMR (DMSO-d$_6$): |
|---|---|---|---|
| 27 | 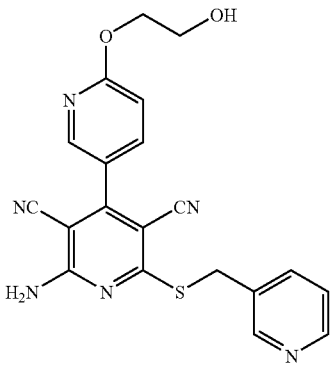 (37% of theory) | 1.49 min (3); m/z = 405 | δ (400 MHz) = 8.53 (d, 1H), 8.33 (s, 1H), 8.32-7.97 (br. s, 2H), 7.92 (dd, 1H), 7.75 (dt, 1H), 7.63 (d, 1H), 7.31-7.27 (m, 1H), 7.00 (d, 1H), 4.88 (t, 1H), 4.61 (s, 2H), 4.38-4.32 (m, 2H), 3.77-3.70 (m, 2H). |
| 28 | 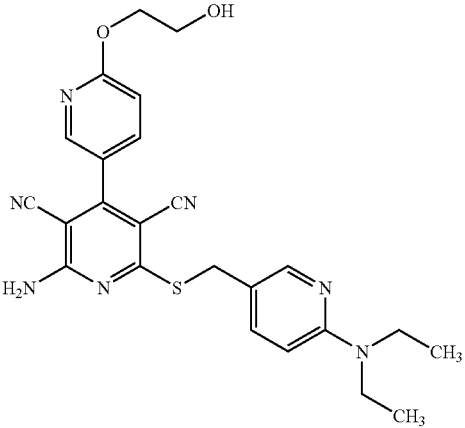 (38% of theory) | 1.91 min (10); m/z = 476 | δ (400 MHz) = 8.38-7.96 (br. s, 2H), 8.34 (d, 1H), 8.23 (d, 1H), 7.91 (dd, 1H), 7.57 (dd, 1H), 6.99 (d, 1H), 6.53 (d, 1H), 4.88 (t, 1H), 4.37-4.32 (m, 2H), 4.36 (s, 2H), 3.73 (q, 2H), 3.47 (q, 4H), 1.08 (t, 6H). |
| 29 | 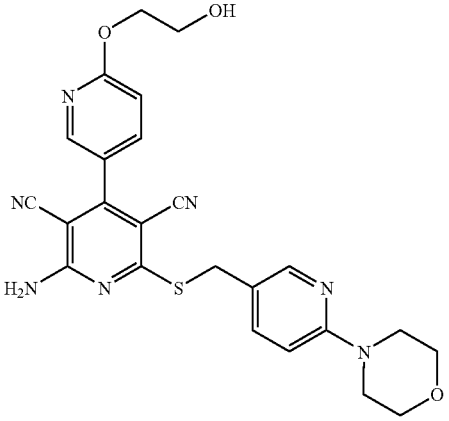 (45% of theory) | 2.11 min (10); m/z = 490 | δ (400 MHz) = 8.49-7.95 (br. s, 2H), 8.35-8.30 (m, 2H), 7.91 (dd, 1H), 7.69 (dd, 1H), 7.00 (d, 1H), 6.79 (d, 1H), 4.88 (t, 1H), 4.38 (s, 2H), 4.34 (t, 2H), 3.74 (q, 2H), 3.70-3.63 (m, 4H), 3.45-3.38 (m, 4H). |

TABLE 2-continued
| Example No. | Structure (yield) | LC-MS: R_t [min] (Method); MS (ESI): m/z [M + H]+ | 1H-NMR (DMSO-d6): |
|---|---|---|---|
| 30 | 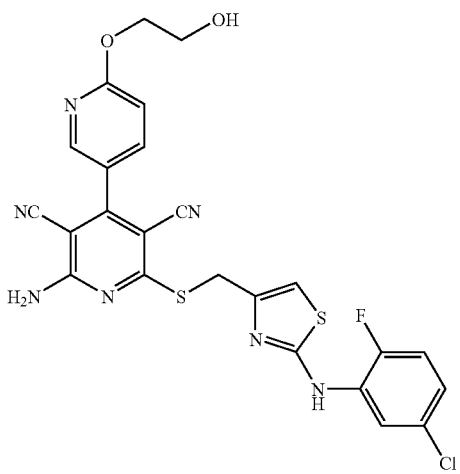<br>(42% of theory) | 2.41 min (2);<br>m/z = 554 | δ (400 MHz) = 10.27 (s, 1H), 8.60 (dd, 1H), 8.43-7.97 (br. s, 2H), 8.35 (d, 1H), 7.92 (dd, 1H), 7.30 (d, 1H), 7.28 (d, 1H), 7.08 (s, 1H), 7.05-6.97 (m, 2H), 4.89 (t, 1H), 4.53 (s, 2H), 4.36 (t, 2H), 3.73 (dq, 2H). |
| 31 | 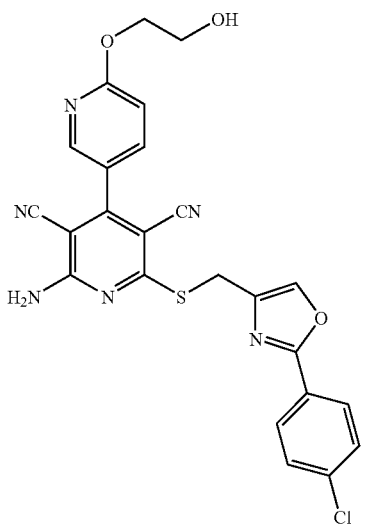<br>(49% of theory) | 3.45 min (12);<br>m/z = 505 | δ (400 MHz) = 8.44-7.87 (br. s, 2H), 8.39-8.32 (m, 2H), 7.98 (d, 2H), 7.91 (dd, 1H), 7.60 (d, 2H), 7.00 (d, 1H), 4.89 (t, 1H), 4.42 (s, 2H), 4.34 (t, 2H), 3.76-3.60 (m, 2H). |

TABLE 2-continued

| Example No. | Structure (yield) | LC-MS: $R_t$ [min] (Method); MS (ESI): m/z [M + H]$^+$ | $^1$H-NMR (DMSO-d$_6$): |
|---|---|---|---|
| 32 | 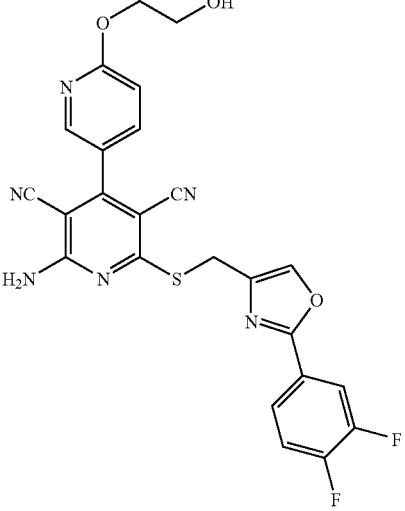<br>(52% of theory) | 3.33 min (10); m/z = 507 | δ (400 MHz) = 8.42-7.88 (br. s, 2H), 8.39 (s, 1H), 8.34 (d, 1H), 7.97 (dd, 1H), 7.92 (dd, 1H), 7.86-7.79 (m, 1H), 7.61 (q, 1H), 7.00 (d, 1H), 4.88 (t, 1H), 4.41 (s, 2H), 4.35 (t, 2H), 3.77-3.70 (m, 2H). |

Example 33

N-[2'-Amino-6'-({[2-(4-chlorophenyl)-1,3-thiazol-4-yl]methyl}thio)-3',5'-dicyano-3,4'-bipyridin-6-yl]acetamide

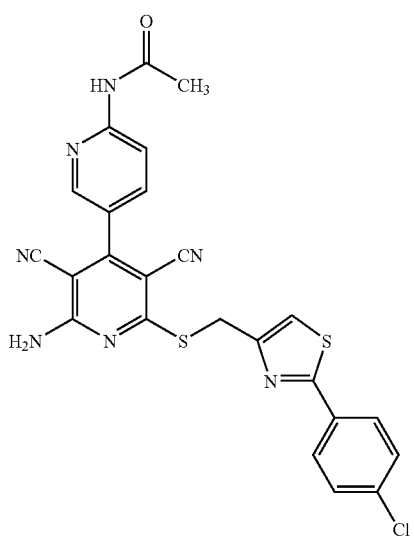

15 mg (0.03 mmol) of the compound from example 20A are dissolved in 0.7 ml of dry DMF, and 10 mg (0.04 mmol) of 4-(chloromethyl)-2-(4-chlorophenyl)-1,3-thiazole and 11 mg (0.14 mmol) of sodium bicarbonate are added. The reaction mixture is stirred at RT for 8 h. The mixture is then poured into 2 ml of saturated aqueous sodium bicarbonate solution, and the aqueous phase is extracted three times with in each case 5 ml of ethyl acetate. The combined organic phases are dried over magnesium sulphate, and the solvent is removed on a rotary evaporator.

Yield: 3 mg (17% of theory)

$^1$H-NMR (400 MHz, DMSO-d$_6$): δ=10.79 (s, 1H), 8.48 (d, 1H), 8.44-8.02 (br. s, 2H), 8.20 (d, 1H), 7.99 (dd, 1H), 7.97-7.90 (m, 3H), 7.57 (d, 2H), 4.64 (s, 2H), 2.14 (s, 3H).

LC-MS (Method 8): $R_t$=2.64 min; MS (ESIpos): m/z=518 [M+H]$^+$.

Example 34

2'-Amino-6'-({[2-(4-chlorophenyl)-1,3-thiazol-4-yl]methyl}thio)-5-(2-hydroxyethoxy)-2,4'-bipyridine-3',5'-dicarbonitrile

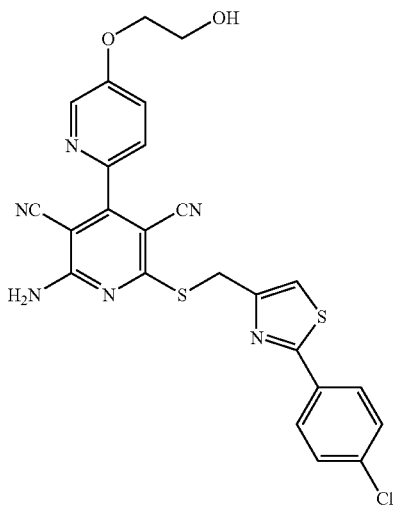

23 mg of the crude product from example 29A are dissolved in 0.7 ml of dry DMF, and 11 mg (0.04 mmol) of 4-(chloromethyl)-2-(4-chlorophenyl)-1,3-thiazole and 12 mg (0.14 mmol) of sodium bicarbonate are added. The reaction mixture is stirred at RT for 8 h. The mixture is then poured into 2 ml of saturated aqueous sodium bicarbonate solution, and the aqueous phase is extracted three times with in each case 4 ml of ethyl acetate. The combined organic phases are dried over magnesium sulphate, and the solvent is removed on a rotary evaporator. The residue is purified by preparative HPLC (column: YMC GEL ODS-AQ S-5/15 μm; mobile phase gradient: acetonitrile/water 10:90→95:5).

Yield: 4 mg (21% of theory)

$^1$H-NMR (400 MHz, DMSO-$d_6$): δ=8.47 (d, 1H), 8.40-7.87 (br. s, 2H), 7.98-7.90 (m, 3H), 7.74 (d, 1H), 7.64-7.58 (m, 1H), 7.58-7.53 (m, 2H), 4.97 (t, 1H), 4.64 (s, 2H), 4.19 (t, 2H), 3.79-3.71 (m, 2H).

LC-MS (Method 8): $R_t$=2.58 min; MS (ESIpos): m/z=521 [M+H]$^+$.

The examples listed in Table 3 below are prepared from the appropriate starting materials analogously to example 34:

TABLE 3

| Example No. | Structure (yield) | LC-MS: $R_t$ [min] (Method); MS (ESI): m/z [M + H]$^+$ | $^1$H-NMR (400 MHz, DMSO-$d_6$): |
|---|---|---|---|
| 35 | 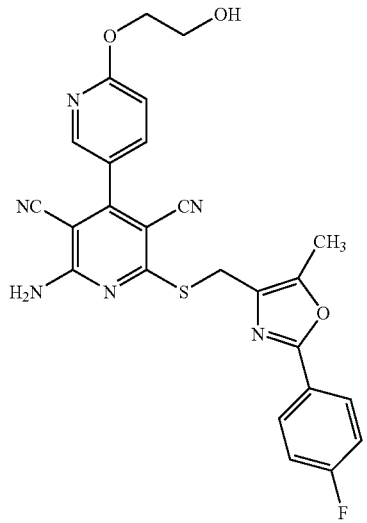 (39% of theory) | 1.92 min (5); m/z = 503 | δ = 8.37 (d, 1H), 8.28-8.05 (br. s, 2H), 8.00-7.91 (m, 3H), 7.36 (pseudo-t, 2H), 7.01 (d, 1H), 4.87 (t, 1H), 4.52 (s, 2H), 4.34 (t, 2H), 3.78-3.71 (m, 2H), 2.47 (s, 3H). |
| 36 | 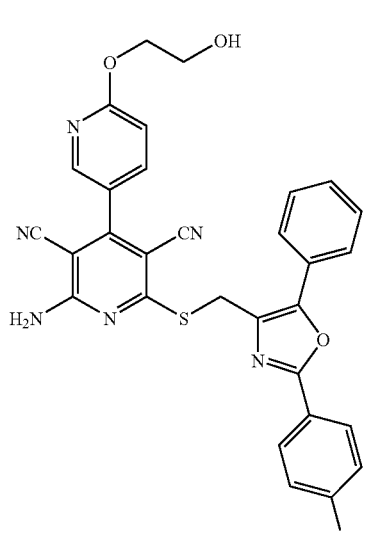 (71% of theory) | 2.37 min (5); m/z = 581 | δ = 8.38 (d, 1H), 8.10 (d, 2H), 8.07-7.98 (br. s, 2H), 7.94 (dd, 1H), 7.84 (d, 2H), 7.65 (d, 2H), 7.59 (t, 2H), 7.48 (t, 1H), 7.02 (d, 1H), 4.89 (t, 1H), 4.83 (s, 2H), 4.37 (t, 2H), 3.78-3.71 (m, 2H). |

TABLE 3-continued
| Example No. | Structure (yield) | LC-MS: R$_t$ [min] (Method); MS (ESI): m/z [M + H]$^+$ | $^1$H-NMR (400 MHz, DMSO-d$_6$): |
|---|---|---|---|
| 37 | 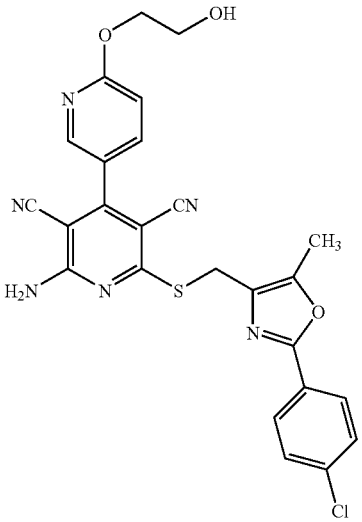 (34% of theory) | 2.67 min (8); m/z = 519 | δ = 8.35 (d, 1H), 8.27-8.03 (br. s, 2H), 7.96-7.89 (m, 3H), 7.62-7.54 (m, 2H), 7.01 (d, 1H), 4.89 (t, 1H), 4.52 (s, 2H), 4.35 (t, 2H), 3.77-3.70 (m, 2H), 2.48 (s, 3H). |
| 38 | 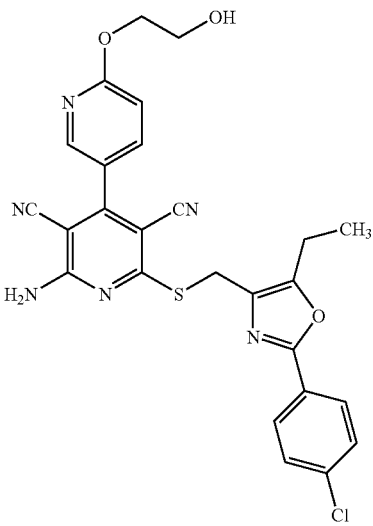 (43% of theory) | 2.19 min (14); m/z = 533 | δ = 8.37 (d, 1H), 8.32-8.02 (br. s, 2H), 7.98-7.90 (m, 3H), 7.49 (pseudo-t, 2H), 7.00 (d, 1H), 4.88 (t, 1H), 4.52 (s, 2H), 4.36 (t, 2H), 3.77-3.70 (m, 2H), 2.89 (q, 2H), 1.21 (t, 3H). |
| 39 | 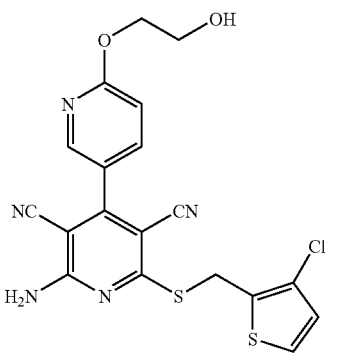 (36% of theory) | 2.13 min (3); m/z = 444 | δ = 8.38 (d, 1H), 8.32-8.05 (br. s, 2H), 7.94 (dd, 1H), 7.59 (d, 1H), 7.06 (d, 1H), 7.01 (d, 1H), 4.88 (t, 1H), 4.71 (s, 2H), 4.37 (t, 2H), 3.74 (q, 2H). |

TABLE 3-continued
| Example No. | Structure (yield) | LC-MS: R_t [min] (Method); MS (ESI): m/z [M + H]+ | 1H-NMR (400 MHz, DMSO-d_6): |
|---|---|---|---|
| 40 | 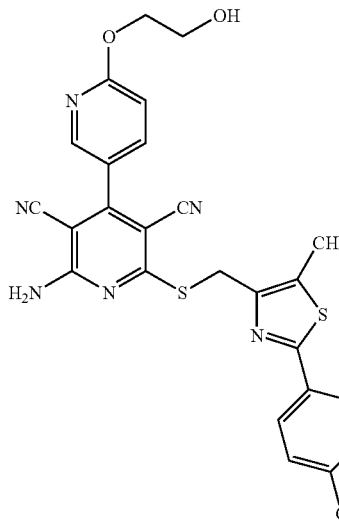<br>(58% of theory) | 1.37 min (13); m/z = 535 | δ = 8.37 (d, 1H), 8.28-8.03 (br. s, 2H), 7.93 (dd, 1H), 7.88 (d, 2H), 7.54 (d, 2H), 7.01 (d, 1H), 4.87 (t, 1H), 4.69 (s, 2H), 4.37 (t, 2H), 3.73 (q, 2H), 2.50 (s, 3H). |
| 41 | 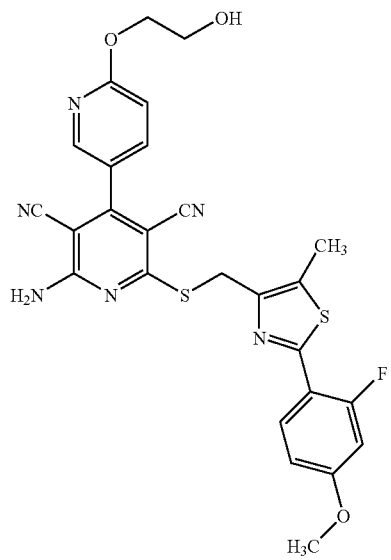<br>(51% of theory) | 1.17 min (13); m/z = 533 | 8.37 (d, 1H), 8.28-8.00 (br. s, 2H), 7.94 (dd, 1H), 7.87 (t, 1H), 7.01 (2d, 2H), 6.92 (dd, 1H), 4.88 (t, 1H), 4.51 (s, 2H), 4.34 (t, 2H), 3.84 (s, 3H), 3.73 (q, 2H), 2.43 (s, 3H). |

Example 42

2'-Amino-6'-({[2-(4-chlorophenyl)-1,3-oxazol-4-yl]methyl}thio)-6-{[(2S)-2,3-dihydroxypropyl]-oxy}-3,4'-bipyridine-3',5'-dicarbonitrile

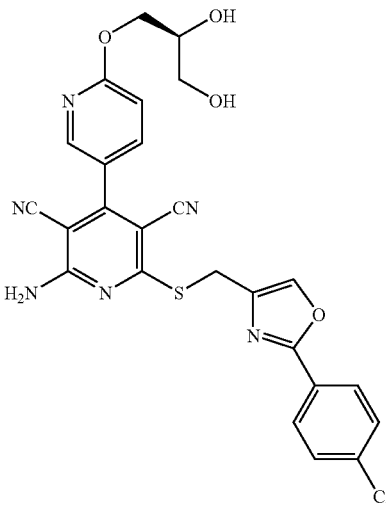

95 mg (0.17 mmol) of the compound from example 32A are dissolved in 4 ml of acetic acid. 2 ml of water are then added. The reaction solution is stirred at RT for 12 h. The solvent is then removed on a rotary evaporator, and the residue is purified directly by preparative HPLC (column: YMC GEL ODS-AQ S-5/15 μm; mobile phase gradient: acetonitrile/water 10:90→95:5). If required, the product may be purified further by HPLC chromatography on a chiral phase [column: Daicel Chiralpak AS 10 μm, 250 mm×20 mm; mobile phase: isohexane/ethanol 60:40 (v/v); flow rate: 15 ml/min; temperature: 40° C.; detection: 220 nm].

Yield: 70 mg (79% of theory)

$^1$H-NMR (400 MHz, DMSO-$d_6$): δ=8.40-8.02 (br. s, 2H), 8.37 (s, 1H), 8.34 (d, 1H), 7.98 (d, 2H), 7.91 (dd, 1H), 7.61 (d, 2H), 7.01 (d, 1H), 4.96 (d, 1H), 4.67 (t, 1H), 4.43 (s, 2H), 4.38 (dd, 1H), 4.21 (dd, 1H), 3.87-3.79 (m, 1H), 3.36 (t, 2H).

LC-MS (Method 14): $R_t$=1.85 min; MS (ESIpos): m/z=535 [M+H]$^+$.

Example 43

2'-Amino-6'-({[2-(4-chlorophenyl)-1,3-oxazol-4-yl]methyl}thio)-6-{[(2R)-2,3-dihydroxypropyl]-oxy}-3,4'-bipyridine-3',5'-dicarbonitrile

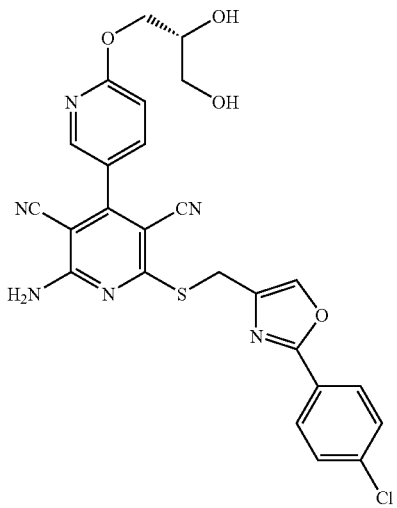

The title compound is prepared analogously to example 42 from 81 mg (0.14 mmol) of the compound from example 33A. Purification of the crude product is likewise carried out as described in example 42.

Yield: 66 mg (87% of theory)

$^1$H-NMR (400 MHz, DMSO-$d_6$): δ=8.41-8.02 (br. s, 2H), 8.38 (s, 1H), 8.33 (d, 1H), 7.98 (d, 2H), 7.90 (dd, 1H), 7.61 (d, 2H), 7.01 (d, 1H), 4.97 (d, 1H), 4.68 (t, 1H), 4.43 (s, 2H), 4.38 (dd, 1H), 4.21 (dd, 1H), 3.88-3.79 (m, 1H), 3.44 (t, 2H).

LC-MS (Method 14): $R_t$=1.84 min; MS (ESIpos): m/z=535 [M+H]$^+$.

Example 44

2'-({[2-(4-Chlorophenyl)-1,3-thiazol-4-yl]methyl}thio)-6-(2-hydroxyethoxy)-6'-pyrrolidin-1-yl-3,4'-bipyridine-3',5'-dicarbonitrile

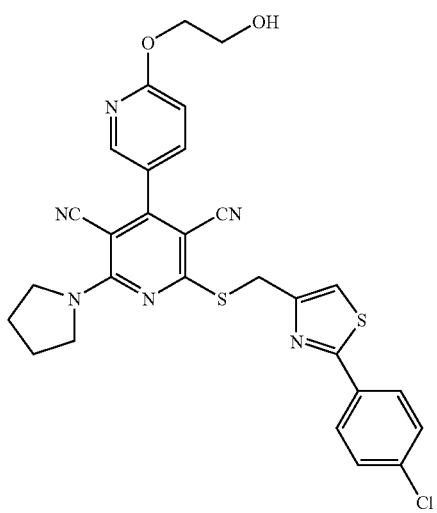

150 mg (0.28 mmol) of the compound from example 38A are initially charged in 3 ml of dry THF, and 39 mg (0.56 mmol) of pyrrolidine are added. The reaction mixture is stirred at RT for 10 h. 2 ml of water are then added to the mixture, which is purified directly by preparative HPLC (column: YMC GEL ODS-AQ S-5/15 μm; mobile phase gradient: acetonitrile/water 10:90→95:5).

Yield: 135 mg (85% of theory)

$^1$H-NMR (400 MHz, DMSO-$d_6$): δ=8.35 (d, 1H), 7.98-7.90 (m, 3H), 7.69 (s, 1H), 7.58 (d, 2H), 7.01 (d, 1H), 4.89 (t, 1H), 4.71 (s, 2H), 4.37 (t, 2H), 3.90-3.79 (br. s, 4H), 3.74 (q, 2H), 2.00-1.88 (br. s, 4H).

LC-MS (Method 13): $R_t$=1.52 min; MS (ESIpos): m/z=575 [M+H]$^+$.

The examples listed in Table 4 below are prepared from the appropriate starting materials analogously to example 44:

TABLE 4
| Example No. | Structure (yield) | LC-MS: R$_t$ [min] (Method); MS (ESI): m/z [M + H]$^+$ | $^1$H-NMR (400 MHz, DMSO-d$_6$): |
|---|---|---|---|
| 45 | 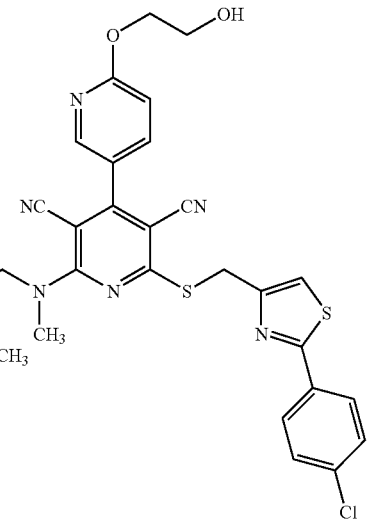 (47% of theory) | 1.04 min (13); m/z = 606 | δ = 8.39 (d, 1H), 7.99-7.92 (m, 3H), 7.70 (s, 1H), 7.58 (d, 2H), 7.02 (d, 1H), 4.89 (t, 1H), 4.71 (s, 2H), 4.37 (s, 2H), 3.89 (t, 2H), 3.75 (q, 2H), 3.41 (s, 3H), 2.13 (s, 6H). |
| 46 | 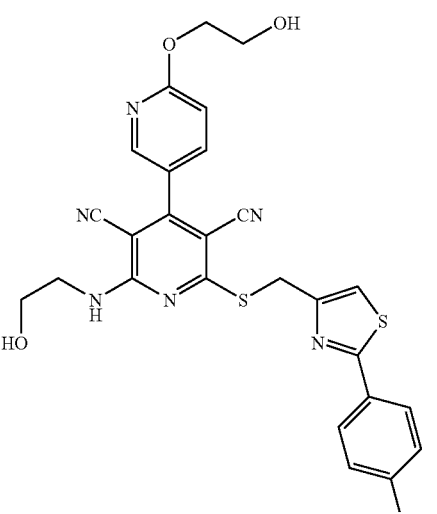 (88% of theory) | 1.27 min (13); m/z = 565 | δ = 8.36 (d, 1H), 8.13 (t, 1H), 7.98-7.90 (m, 3H), 7.71 (s, 1H), 7.58 (d, 2H), 7.02 (d, 1H), 4.88 (t, 1H), 4.82 (t, 1H), 4.71 (s, 2H), 4.37 (t, 2H), 3.74 (q, 2H), 3.66-3.58 (m, 2H), 3.58-3.51 (m, 2H). |

The examples listed in Table 5 below are prepared from the appropriate starting materials analogously to example 34:

TABLE 5

| Example No. | Structure (yield) | LC-MS: R$_t$ [min] (Method); MS (ESI): m/z [M + H]$^+$ | $^1$H-NMR (400 MHz, DMSO-d$_6$): |
|---|---|---|---|
| 47 | 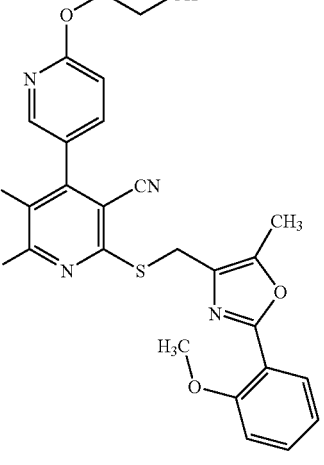<br>(66% of theory) | 1.12 min (13); m/z = 515 | δ = 8.37 (d, 1H), 8.26-8.03 (br. s, 2H), 7.93 (dd, 1H), 7.76 (dd, 1H), 7.52-7.46 (m, 1H), 7.18 (d, 1H), 7.08-6.99 (m, 2H), 4.87 (t, 1H), 4.52 (s, 2H), 4.37 (t, 2H), 3.86 (s, 3H), 3.73 (q, 2H), 2.43 (s, 3H). |
| 48 | 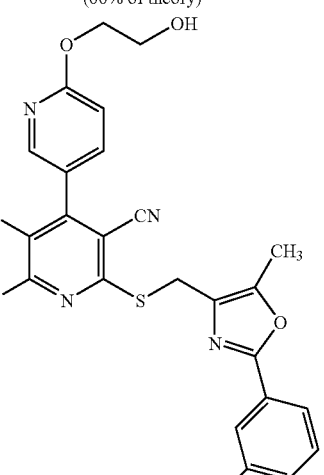<br>(36% of theory) | 2.08 min (16); m/z = 545 | δ = 8.36 (d, 1H), 8.29-8.03 (br. s, 2H), 7.92 (dd, 1H), 7.48 (dd, 1H), 7.41 (d, 1H), 7.08 (d, 1H), 7.00 (d, 1H), 4.88 (t, 1H), 4.50 (s, 2H), 4.36 (t, 2H), 3.74 (s, 3H), 3.73 (s, 3H), 3.77-3.71 (m, 2H), 2.47 (s, 3H). |
| 49 | 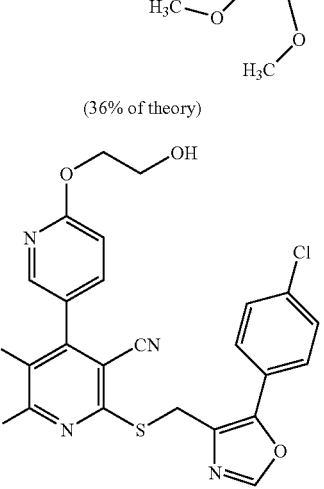<br>(64% of theory) | 1.18 min (13); m/z = 505 | δ = 8.51 (s, 1H), 8.38 (d, 1H), 8.16-8.01 (br. s, 2H), 7.95 (dd, 1H), 7.74 (d, 2H), 7.61 (d, 2H), 7.02 (d, 1H), 4.89 (t, 1H), 4.76 (s, 2H), 4.37 (t, 2H), 3.74 (q, 2H). |

B. ASSESSING THE PHARMACOLOGICAL AND PHYSIOLOGICAL ACTIVITY

The pharmacological and physiological activity of the compounds according to the invention can be demonstrated in the following assays:

B-1. Indirect Determination of the Adenosine Agonism by Way of Gene Expression

Cells of the CHO (Chinese Hamster Ovary) permanent cell line are transfected stably with the cDNA for the adenosine receptor subtypes A1, A2a and A2b. The adenosine A1 receptors are coupled to the adenylate cyclase by way of $G_i$ proteins, while the adenosine A2a and A2b receptors are coupled by way of $G_s$ proteins. In correspondence with this, the formation of cAMP in the cell is inhibited or stimulated, respectively. After that, expression of the luciferase is modulated by way of a cAMP-dependent promoter. The luciferase test is optimized, with the aim of high sensitivity and reproducibility, low variance and good suitability for implementation on a robot system, by varying several test parameters, such as cell density, duration of the growth phase and the test incubation, forskolin concentration and medium composition. The following test protocol is used for pharmacologically characterizing cells and for the robot-assisted substance screening:

The stock cultures are grown, at 37° C. and under 5% $CO_2$, in DMEM/F12 medium containing 10% FCS (foetal calf serum) and in each case split 1:10 after 2-3 days. The test cultures are seeded in 384-well plates with 2000 cells per well and grown at 37° C. for approx. 48 hours. The medium is then replaced with a physiological sodium chloride solution (130 mM sodium chloride, 5 mM potassium chloride, 2 mM calcium chloride, 20 mM HEPES, 1 mM magnesium chloride hexahydrate, 5 mM sodium bicarbonate, pH 7.4). The substances to be tested, which are dissolved in DMSO, are pipetted into the test cultures (maximum final concentration of DMSO in the test mixture: 0.5%) in a dilution series of from $5 \times 10^{-11}$ M to $3 \times 10^{-6}$ M (final concentration). 10 minutes later, forskolin is added to the A1 cells and all the cultures are subsequently incubated at 37° C. for four hours. After that, 35 µl of a solution which is composed of 50% lysis reagent (30 mM disodium hydrogenphosphate, 10% glycerol, 3% TritonX100, 25 mM TrisHCl, 2 mM dithiotreitol (DTT), pH 7.8) and 50% luciferase substrate solution (2.5 mM ATP, 0.5 mM luciferin, 0.1 mM coenzyme A, 10 mM tricine, 1.35 mM magnesium sulphate, 15 mM DTT, pH 7.8) are added to the test cultures, which are shaken for approx. 1 minute and the luciferase activity is measured using a camera system. The $EC_{50}$ values are determined, i.e., the concentrations at which 50% of the luciferase answer is inhibited in the case of the A1 cell, and, respectively, 50% of the maximum stimulation with the corresponding substance is achieved in the case of the A2b and A2a cells. The adenosine-analogous compound NECA (5-N-ethylcarboxamidoadenosine), which binds to all adenosine receptor subtypes with high affinity and possesses an agonistic effect, is used in these experiments as the reference compound [Klotz, K. N., Hessling, J., Hegler, J., Owman, C., Kull, B., Fredholm, B. B., Lohse, M. J., "Comparative pharmacology of human adenosine receptor subtypes—characterization of stably transfected receptors in CHO cells", Naunyn Schmiedebergs Arch. Pharmacol., 357 (1998), 1-9).

Table 1 below lists the $EC_{50}$ values of representative working examples for the receptor stimulation on adenosine A1, A2a and A2b receptor subtypes:

TABLE 1

| Example No. | $EC_{50}$ A1 [nM] (1 µM forskolin) | $EC_{50}$ A2a [nM] | $EC_{50}$ A2b [nM] |
|---|---|---|---|
| 1 | 0.8 | 2180 | 5.8 |
| 3 | 0.2 | 123 | 3.7 |
| 5 | 0.6 | 190 | 8.5 |
| 11 | 0.4 | 150 | 5.7 |
| 13 | 0.09 | 21 | 5.5 |
| 19 | 0.04 | 663 | 234 |
| 21 | 3.6 | >3000 | >3000 |
| 22 | 0.6 | 120 | 117 |
| 25 | 4.1 | >3000 | >3000 |
| 31 | 0.09 | 101 | 235 |
| 37 | 0.3 | 1750 | 1260 |
| 42 | 0.09 | 355 | 516 |
| 43 | 0.04 | 72 | 185 |
| 44 | 0.08 | 547 | 95 |
| 46 | 0.04 | 266 | 166 |

B-2. Studies on Isolated Blood Vessels

The caudal artery of anaesthetized rats is excised and mounted in a conventional apparatus for measuring isolated blood vessels. The vessels are perfused in a heated bath and contracted using phenylephrine. The extent of the contraction is determined using a contraction meter. Test substances are added to the precontracted blood vessels, and the reduction of the contraction of the vessels is measured. A reduction of contraction corresponds to a dilation of the vessels. The concentration at which the contraction of the blood vessels is reduced by 50% is given as the $EC_{50}$ value of a test substance with respect to its relaxing properties.

B-3. Measurement of Blood Pressure and Heart Rate on Awake Rats

Various dosages of test substances are administered orally to awake SHR (spontaneously hypertensive rats) rats carrying an internal transmitter capable of measuring permanently both blood pressure and heart rate (telemetric monitoring of haemodynamic parameters). Blood pressure, heart rate and their changes are then recorded over a period of 24 hours.

B-4. Measurement of Blood Pressure and Heart Rate on Awake Marmosets

Various concentrations of the test substances are administered orally to awake marmosets which carry an internal transmitter capable of measuring both blood pressure and heart rate (telemetric monitoring of haemodynamic parameters). Blood pressure, heart rate and their changes are then recorded for a period of 6-24 hours.

B-5. Determination of the Solubility

Reagents Required:

PBS buffer pH 7.4: 90.00 g of NaCl p.a. (for example from Merck, Art No. 1.06404.1000), 13.61 g of $KH_2PO_4$ p.a. (for example from Merck, Art. No. 1.04873.1000) and 83.35 g of 1 N NaOH (for example from Bernd Kraft GmbH, Art. No. 01030.4000) are weighed into a 1 liter volumetric flask, which is then filled with water, and the mixture is stirred for about 1 hour;

acetate buffer pH 4.6: 5.4 g of sodium acetate×3 $H_2O$ p.a. (for example from Merck, Art. No. 1.06267.0500) are weighed into a 100 ml volumetric flask and dissolved in 50 ml of water, 2.4 g of glacial acetic acid are added, the mixture is made up to 100 ml with water, the pH is checked and, if required, adjusted to pH 4.6;

dimethyl sulphoxide (for example from Baker, Art. No. 7157.2500);

distilled water.

Preparation of the Solutions for Calibration:

Preparation of the initial solution for solutions of calibration (stock solution): about 0.5 mg of the test substance are accurately weighed into a 2 ml Eppendorf safe-lock tube (from Eppendorf, Art. No. 0030 120.094), DMSO is added to a concentration of 600 µg/ml (for example 0.5 mg of substance+833 µl of DMSO) and the mixture is vortexed until complete dissolution.

Solution for calibration 1 (20 µg/ml): 1000 µl of DMSO are added to 34.4 µl of the stock solution, and the mixture is homogenized.

Solution for calibration 2 (2.5 µg/ml): 700 µl of DMSO are added to 100 µl of the solution for calibration 1, and the mixture is homogenized.

Preparation of the Sample Solutions:

Sample solution for solubilities of up to 10 g/l in PBS buffer pH 7.4: About 5 mg of the test substance are weighed accurately into a 2 ml Eppendorf safe-lock tube (from Eppendorf, Art. No. 0030 120.094), and PBS buffer pH 7.4 is added to a concentration of 5 g/l (for example 5 mg of substance+500 µl of PBS buffer pH 7.4).

Sample solution for solubilities of up to 10 g/l in acetate buffer pH 4.6: About 5 mg of the test substance are weighed accurately into a 2 ml Eppendorf safe-lock tube (from Eppendorf, Art. No. 0030 120.094), and acetate buffer pH 4.6 is added to a concentration of 5 g/l (for example 5 mg of substance+500 µl of acetate buffer pH 4.6).

Sample solution for solubilities of up to 10 g/l in water: About 5 mg of the test substance are weighed accurately into a 2 ml Eppendorf safe-lock tube (from Eppendorf, Art. No. 0030 120.094), and water is added to a concentration of 5 g/l (for example 5 mg of substance+500 µl of water).

Practice:

The sample solutions prepared in this manner are shaken at 20° C. and 1400 rpm for 24 hours using a controlled temperature shaker (for example Eppendorf Thermomixer comfort Art. No. 5355 000.011 with exchangeable thermoblock Art. No. 5362.000.019). From these solutions, in each case 180 µl are removed and transferred into Beckman polyallomer centrifuge tubes (Art. No. 343621). These solutions are centrifuged at about 223 000×g for one hour (for example Beckman Optima L-90K ultracentrifuge with type 42.2 Ti rotor at 42 000 rpm). From each sample solution, 100 µl of supernatent are removed and diluted 1:5, 1:100 and 1:1000 with the respective solvent used (water, PBS buffer 7.4 or acetate buffer pH 4.6). Each dilution is filled into a vessel suitable for HPLC analysis.

Analysis:

The samples are analysed by RP-HPLC. Quantification is via a two-point calibration curve of the test compound in DMSO. The solubility is expressed in mg/l. Analysis sequence: 1) solution for calibration 2.5 mg/ml; 2) solution for calibration 20 µg/ml; 3) sample solution 1:5; 4) sample solution 1:100; 5) sample solution 1:1000.

HPLC Methods for Acids:

Agilent 1100 with DAD (G1315A), quat. pump (G1311A), autosampler CTC HTS PAL, degasser (G1322A) and column thermostat (G1316A); column: Phenomenex Gemini C18, 50 mm×2 mm, 5µ; temperature: 40° C.; mobile phase A: water/phosphoric acid pH 2; mobile phase B: acetonitrile; flow rate: 0.7 ml/min; gradient: 0-0.5 min 85% A, 15% B; ramp: 0.5-3 min 10% A, 90% B; 3-3.5 min 10% A, 90% B; ramp: 3.5-4 min 85% A, 15% B; 4-5 min 85% A, 15% B.

HPLC Method for Bases:

Agilent 1100 with DAD (G1315A), quat. pump (G1311A), autosampler CTC HTS PAL, degasser (G1322A) and column thermostat (G1316A); column: VDSoptilab Kromasil 100 C18, 60 mm×2.1 mm, 3.5µ; temperature: 30° C.; mobile phase A: water+5 ml of perchloric acid/l; mobile phase B: acetonitrile; flow rate: 0.75 ml/min; gradient: 0-0.5 min 98% A, 2% B; ramp: 0.5-4.5 min 10% A, 90% B; 4.5-6 min 10% A, 90% B; ramp: 6.5-6.7 min 98% A, 2% B; 6.7-7.5 min 98% A, 2% B.

C. WORKING EXAMPLES OF PHARMACEUTICAL COMPOSITIONS

The compounds of the invention can be converted into pharmaceutical preparations in the following ways:

Tablet:

Composition:

100 mg of the compound of the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:

The mixture of compound of the invention, lactose and starch is granulated with a 5% strength solution (m/m) of the PVP in water. The granules are dried and mixed with the magnesium stearate for 5 minutes. This mixture is compressed in a conventional tablet press (see above for format of the tablet). A guideline compressive force for the compression is 15 kN.

Suspension which can be Administered Orally:

Composition:

1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.

Production:

The Rhodigel is suspended in ethanol, and the compound of the invention is added to the suspension. The water is added while stirring. The mixture is stirred for about 6 h until the swelling of the Rhodigel is complete.

Solution which can be Administered Orally:

Composition:

500 mg of the compound of the invention, 2.5 g of polysorbate and 97 g of polyethylene glycol 400. 20 g of oral solution correspond to a single dose of 100 mg of the compound of the invention.

Production:

The compound of the invention is suspended in the mixture of polyethylene glycol and polysorbate with stirring. The stirring process is continued until the compound of the invention has completely dissolved.

i.v. Solution:

The compound of the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:
1. Compound of the formula (I)

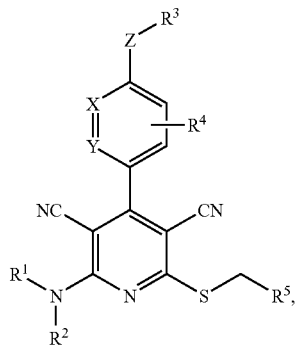

in which
X represents N and Y represents C—R⁶, where
  R⁶ represents hydrogen or (C₁-C₄)-alkyl,
Z represents N—R⁷ or O, where
  R⁷ represents hydrogen or (C₁-C₄)-alkyl which may be substituted by hydroxyl or (C₁-C₄)-alkoxy,
R¹ and R² are identical or different and independently of one another represent hydrogen or (C₁-C₆)-alkyl which may be mono- or disubstituted by identical or different substituents from a group consisting of hydroxyl, (C₁-C₄)-alkoxy, amino, mono-(C₁-C₄)-alkylamino, di-(C₁-C₄)-alkylamino, carboxyl, and (C₁-C₄)-alkoxycarbonyl,
R³ represents hydrogen or (C₁-C₆)-alkyl which may be mono- or disubstituted by identical or different substituents from the group consisting of (C₃-C₆)-cycloalkyl, oxo, hydroxyl, (C₁-C₄)-alkoxy, carboxyl, amino, mono-(C₁-C₄)-alkylamino and di-(C₁-C₄)-alkylamino, or represents (C₄-C₆)-cycloalkyl,
where the cycloalkyl radicals mentioned for their part may be substituted up to two times by identical or different substituents from the group consisting of (C₁-C₄)-alkyl, hydroxyl, oxo and (C₁-C₄)-alkoxy,
R⁴ represents hydrogen, halogen, (C₁-C₄)-alkyl or (C₁-C₄)-alkoxy, where alkyl and alkoxy may each be substituted up to three times by fluorine,
and
R⁵ represents (C₆-C₁₀)-aryl, which may
  (i) be mono- or disubstituted by identical or different substituents from the group consisting of halogen, nitro, cyano, (C₁-C₆)-alkyl, phenyl, hydroxyl, (C₁-C₆)-alkoxy, amino, mono-(C₁-C₆)-alkylamino, mono-(C₂-C₆)-alkenylamino and di-(C₁-C₆)-alkylamino
  and/or
  (ii) be substituted by a group of the formula -L-R⁸, where
    L represents a bond, NH or O
    and
    R⁸ represents phenyl, which may be mono- to trisubstituted by identical or different substituents from the group consisting of halogen, nitro, cyano, (C₁-C₆)-alkyl, trifluoromethyl, hydroxyl, (C₁-C₆)-alkoxy, difluoromethoxy, trifluoromethoxy, amino, mono-(C₁-C₆)-alkylamino, di-(C₁-C₆)-alkylamino, (C₁-C₆)-alkoxycarbonyl and carboxyl,
or a salt thereof.

2. The compound of claim 1 in which
X represents N and Y represents CH,
Z represents N—R⁷ or O, where
  R⁷ represents hydrogen or methyl,
R¹ represents hydrogen or (C₁-C₄)-alkyl which may be substituted by hydroxyl, (C₁-C₄)-alkoxy, amino, mono-(C₁-C₄)-alkylamino, di-(C₁-C₄)-alkylamino, carboxyl, or (C₁-C₄)-alkoxycarbonyl,
R² represents hydrogen or methyl,
R³ represents (C₁-C₄)-alkyl which may be mono- or disubstituted by identical or different substituents from the group consisting of (C₃-C₅)-cycloalkyl, oxo, hydroxyl, (C₁-C₃)-alkoxy, amino, mono-(C₁-C₃)-alkylamino and di-(C₁-C₃)-alkylamino, or represents cyclopentyl or cyclohexyl,
where the (C₃-C₅)-cycloalkyl, cyclopentyl and cyclohexyl radicals mentioned for their part may be substituted up to two times by identical or different substituents from the group consisting of hydroxyl and methoxy,
R⁴ represents hydrogen, fluorine or chlorine,
and
R⁵ represents phenyl which may
  (i) be mono- or disubstituted by identical or different substituents from the group consisting of fluorine, chlorine, cyano, (C₁-C₄)-alkyl, amino, mono-(C₁-C₄)-alkylamino and di-(C₁-C₄)-alkylamino
  and/or
  (ii) be substituted by a group of the formula -L-R⁸, where
    L represents a bond or NH
    and
    R⁸ represents phenyl which may be mono- to trisubstituted by identical or different substituents from the group consisting of fluorine, chlorine, cyano, (C₁-C₄)-alkyl, trifluoromethyl, (C₁-C₄)-alkoxy, trifluoromethoxy and carboxyl,
or a salt thereof.

3. The compound of claim 1 in which
X represents N and Y represents CH,
Z represents NH or O,
R¹ represents hydrogen or (C₁-C₄)-alkyl which may be substituted by hydroxyl, (C₁-C₄)-alkoxy, amino, mono-(C₁-C₄)-alkylamino or di-(C₁-C₄)-alkylamino,
R² represents hydrogen or methyl,
R³ represents (C₁-C₄)-alkyl which may be mono- or disubstituted by identical or different substituents from the group consisting of oxo, hydroxyl, methoxy, ethoxy and amino,
R⁴ represents hydrogen,
and
R⁵ represents phenyl which may
  (i) be mono- or disubstituted by identical or different substituents from the group consisting of fluorine, chlorine, cyano, (C₁-C₄)-alkyl and amino
  and/or
  (ii) be substituted by a group of the formula -L-R⁸, where
    L represents a bond or NH
    and
    R⁸ represents phenyl which may be mono- or disubstituted by identical or different substituents from the group consisting of fluorine, chlorine, cyano, methyl, trifluoromethyl and methoxy,
or a salt thereof.

4. A process for preparing a compound of formula (I) as defined in claim 1, comprising reacting a compound of the formula (II)

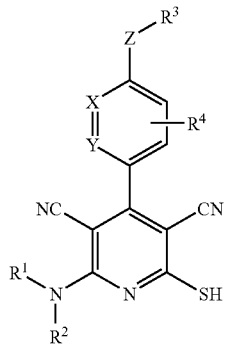

in an inert solvent in the presence of a base with a compound of the formula (III)

in which $R^5$ is as defined in claim 1 and

Q represents a suitable leaving group, and optionally reacting the resulting compounds of formula (I) with a base or acid thereby producing a salt thereof.

in which $R^1$, $R^2$, $R^3$, $R^4$, X, Y and Z are each as defined in claim 1

5. A pharmaceutical composition comprising a compound of claim 1 and an inert non-toxic pharmaceutically suitable auxiliary.

* * * * *